US006977144B2

United States Patent
Legrain et al.

(10) Patent No.: US 6,977,144 B2
(45) Date of Patent: Dec. 20, 2005

(54) SID NUCLEIC ACIDS AND POLYPEPTIDES SELECTED FROM A PATHOGENIC STRAIN OF HEPATITIS C VIRUS AND APPLICATIONS THEREOF

(75) Inventors: Pierre Legrain, Paris (FR); Simon Whiteside, Cambridge (GB); Jerome Wojcik, Paris (FR)

(73) Assignee: Hybrigenics (FR)

( * ) Notice: Subject to any disclaimer, the term of this patent is extended or adjusted under 35 U.S.C. 154(b) by 225 days.

(21) Appl. No.: 09/921,397

(22) Filed: Aug. 2, 2001

(65) Prior Publication Data

US 2002/0151484 A1 Oct. 17, 2002

(30) Foreign Application Priority Data

Aug. 3, 2000 (EP) ............................................ 00402225

(51) Int. Cl.[7] .......................... C12Q 1/70; C12N 15/51; C12N 5/10; C07K 14/18
(52) U.S. Cl. ..................... 435/5; 536/23.72; 536/24.32; 536/23.4; 435/32; 435/320.1; 435/325; 435/252.3; 435/254.1; 530/324
(58) Field of Search .......................... 536/23.72, 24.32, 536/23.4; 435/5, 320.1, 325, 252.3, 254.11, 32; 530/324; 514/44

(56) References Cited

FOREIGN PATENT DOCUMENTS

EP    1 018 558 A1    7/2000
WO    IB-96/05315 A1    2/1996

OTHER PUBLICATIONS

Yanagi et al (PNAS 94:8738–8743, 1997).*
Lesburg et al (Nature Structure Biology 6:937–943, 1999).*
Flajolet M, et al., "A genomic approach of the hepatitis C virus generates a protein interaction map", Gene, vol. 242, No. 1–2, Jan. 25, 2001, pp. 369–379.

* cited by examiner

*Primary Examiner*—Mary E. Mosher
(74) *Attorney, Agent, or Firm*—Lerner, David, Littenberg, Krumholz & Mentlik, LLP

(57) ABSTRACT

The present invention relates to nucleic acids encoding SID® polypeptides which bind selectively to a polypeptide encoded by a pathogenic strain of the hepatitis C virus, as well as to the SID® polypeptides which are encoded by said nucleic acids.

The invention also concerns vectors comprising a nucleic acid encoding a SID® polypeptide as well as host cells transformed with such vectors.

The invention is also directed to two-hybrid methods which make use of the nucleic acids encoding a SID® polypeptide selected from a pathogenic strain of the hepatitis C virus as well as to methods for selecting molecules which inhibit the binding between a SID® polypeptide and a polypeptide which specifically binds thereto.

36 Claims, 11 Drawing Sheets

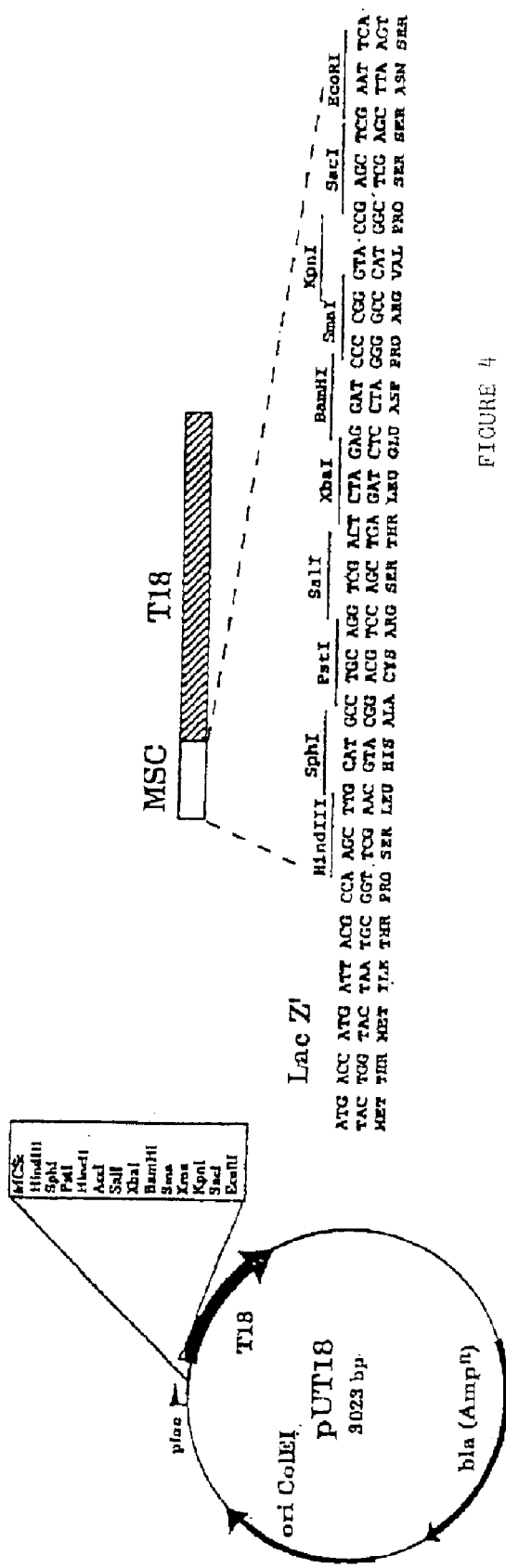
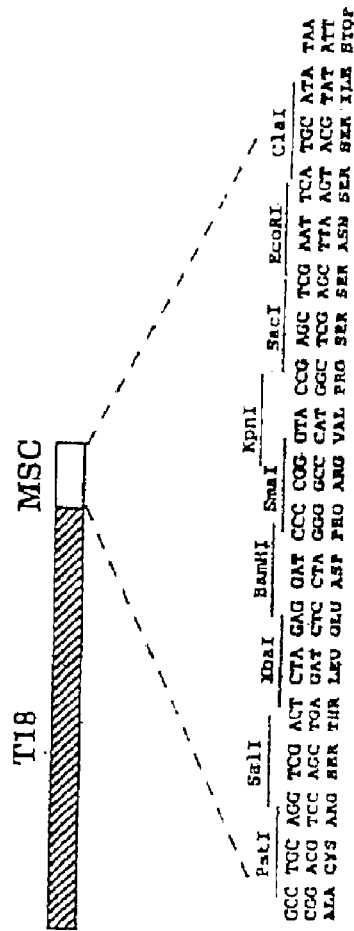
FIGURE 4
FIGURE 5

SEQUENCE LISTING

<160> NUMBER OF SEQ ID NOS: 156

<210> SEQ ID NO 1
<211> LENGTH: 50
<212> TYPE: PRT
<213> ORGANISM: Hepatitis C virus

<400> SEQUENCE: 1

Leu Leu Pro Arg Arg Gly Pro Arg Leu Gly Val Arg Ala Thr Arg Lys
 1               5                  10                  15

Thr Ser Glu Arg Ser Gln Pro Arg Gly Arg Arg Gln Pro Ile Pro Lys
            20                  25                  30

Ala Arg Arg Pro Glu Gly Arg Thr Trp Ala Gln Pro Gly Tyr Pro Trp
        35                  40                  45

Pro Leu
    50

<210> SEQ ID NO 2
<211> LENGTH: 35
<212> TYPE: PRT
<213> ORGANISM: Hepatitis C virus

<400> SEQUENCE: 2

Gly Arg Gly Lys Pro Gly Ile Tyr Arg Phe Val Ala Pro Gly Glu Arg
 1               5                  10                  15

Pro Ser Gly Met Phe Asp Ser Ser Val Leu Cys Glu Cys Tyr Asp Ala
            20                  25                  30

Gly Cys Ala
        35

<210> SEQ ID NO 3
<211> LENGTH: 77
<212> TYPE: PRT
<213> ORGANISM: Hepatitis C virus

<400> SEQUENCE: 3

Asn Thr Asn Arg Arg Pro Gln Asp Val Lys Phe Pro Gly Gly Gly Gln
 1               5                  10                  15

Ile Val Gly Gly Val Tyr Leu Leu Pro Arg Arg Gly Pro Arg Leu Gly
            20                  25                  30

Val Arg Ala Thr Arg Lys Thr Ser Glu Arg Ser Gln Pro Arg Gly Arg
        35                  40                  45

Arg Gln Pro Ile Pro Lys Ala Arg Arg Pro Glu Gly Arg Thr Trp Ala
    50                  55                  60

Gln Pro Gly Tyr Pro Trp Pro Leu Tyr Gly Asn Glu Gly
65                  70                  75

<210> SEQ ID NO 4
<211> LENGTH: 37
<212> TYPE: PRT
<213> ORGANISM: Hepatitis C virus

<400> SEQUENCE: 4

Pro Ser Pro Val Val Gly Thr Thr Asp Arg Ser Gly Ala Pro Thr
 1               5                  10                  15

Tyr Ser Trp Gly Ala Asn Asp Thr Asp Val Phe Val Leu Asn Asn Thr
            20                  25                  30

Arg Pro Pro Leu Gly
        35

<210> SEQ ID NO 5
<211> LENGTH: 150
<212> TYPE: PRT
<213> ORGANISM: Hepatitis C virus

<400> SEQUENCE: 5

Ser Arg Thr Gln Arg Arg Gly Arg Thr Gly Arg Gly Lys Pro Gly Ile
 1               5                  10                  15

Tyr Arg Phe Val Ala Pro Gly Glu Arg Pro Ser Gly Met Phe Asp Ser
            20                  25                  30

Ser Val Leu Cys Glu Cys Tyr Asp Ala Gly Cys Ala Trp Tyr Glu Leu
        35                  40                  45

Thr Pro Ala Glu Thr Thr Val Arg Leu Arg Ala Tyr Met Asn Thr Pro

```
                50                  55                  60
Gly Leu Pro Val Cys Gln Asp His Leu Glu Phe Trp Glu Gly Val Phe
 65                  70                  75                  80

Thr Gly Leu Thr His Ile Asp Ala His Phe Leu Ser Gln Thr Lys Gln
                 85                  90                  95

Ser Gly Glu Asn Phe Pro Tyr Leu Val Ala Tyr Gln Ala Thr Val Cys
            100                 105                 110

Ala Arg Ala Gln Ala Pro Pro Ser Trp Asp Gln Met Trp Lys Cys
        115                 120                 125

Leu Ile Arg Leu Lys Pro Thr Leu His Gly Pro Thr Pro Leu Leu Tyr
130                 135                 140

Arg Leu Gly Ala Val Gln
145                 150

<210> SEQ ID NO 6
<211> LENGTH: 28
<212> TYPE: PRT
<213> ORGANISM: Hepatitis C virus

<400> SEQUENCE: 6

Pro Ser Pro Val Val Val Gly Thr Thr Asp Arg Ser Gly Ala Pro Thr
  1               5                  10                  15

Tyr Ser Trp Gly Ala Asn Asp Thr Asp Val Phe Val
             20                  25

<210> SEQ ID NO 7
<211> LENGTH: 26
<212> TYPE: PRT
<213> ORGANISM: Hepatitis C virus

<400> SEQUENCE: 7

Pro Pro Arg Pro Cys Gly Ile Val Pro Ala Lys Ser Val Cys Gly Pro
  1               5                  10                  15

Val Tyr Cys Phe Thr Pro Ser Pro Val Val
             20                  25

<210> SEQ ID NO 8
<211> LENGTH: 54
<212> TYPE: PRT
<213> ORGANISM: Hepatitis C virus

<400> SEQUENCE: 8

Cys Val Val Ile Val Gly Arg Ile Val Leu Ser Gly Lys Pro Ala Ile
  1               5                  10                  15

Ile Pro Asp Arg Glu Val Leu Tyr Gln Glu Phe Asp Glu Met Glu Glu
             20                  25                  30

Cys Ser Gln His Leu Pro Tyr Ile Glu Gln Gly Met Met Leu Ala Glu
         35                  40                  45

Gln Phe Lys Gln Lys Ala
     50

<210> SEQ ID NO 9
<211> LENGTH: 40
<212> TYPE: PRT
<213> ORGANISM: Hepatitis C virus

<400> SEQUENCE: 9

Gly Asp Phe Asp Ser Val Ile Asp Cys Asn Thr Cys Val Thr Gln Thr
  1               5                  10                  15
```

-continued

```
Val Asp Phe Ser Leu Asp Pro Thr Phe Thr Ile Glu Thr Thr Thr Leu
            20                  25                  30
Pro Gln Asp Ala Val Ser Arg Thr
            35                  40

<210> SEQ ID NO 10
<211> LENGTH: 28
<212> TYPE: PRT
<213> ORGANISM: Hepatitis C virus

<400> SEQUENCE: 10

Glu Arg Pro Ser Gly Met Phe Asp Ser Ser Val Leu Cys Glu Cys Tyr
  1               5                  10                  15
Asp Ala Gly Cys Ala Trp Tyr Glu Leu Thr Pro Ala
            20                  25

<210> SEQ ID NO 11
<211> LENGTH: 27
<212> TYPE: PRT
<213> ORGANISM: Hepatitis C virus

<400> SEQUENCE: 11

Arg Gly Lys Pro Gly Ile Tyr Arg Phe Val Ala Pro Gly Glu Arg Pro
  1               5                  10                  15
Ser Gly Met Phe Asp Ser Ser Val Leu Cys Glu
            20                  25

<210> SEQ ID NO 12
<211> LENGTH: 42
<212> TYPE: PRT
<213> ORGANISM: Hepatitis C virus

<400> SEQUENCE: 12

Leu Glu Asp Ser Val Thr Pro Ile Asp Thr Thr Ile Met Ala Lys Asn
  1               5                  10                  15
Glu Val Phe Cys Val Gln Pro Glu Lys Gly Gly Arg Lys Pro Ala Arg
            20                  25                  30
Leu Ile Val Phe Pro Asp Leu Gly Val Arg
            35                  40

<210> SEQ ID NO 13
<211> LENGTH: 28
<212> TYPE: PRT
<213> ORGANISM: Hepatitis C virus

<400> SEQUENCE: 13

Pro Thr Gly Ser Gly Lys Ser Thr Lys Val Pro Ala Ala Tyr Ala Ala
  1               5                  10                  15
Gln Gly Tyr Lys Val Leu Val Leu Asn Pro Ser Val
            20                  25

<210> SEQ ID NO 14
<211> LENGTH: 33
<212> TYPE: PRT
<213> ORGANISM: Hepatitis C virus

<400> SEQUENCE: 14

Glu Arg Pro Tyr Cys Trp His Tyr Pro Pro Arg Pro Cys Gly Ile Val
  1               5                  10                  15
Pro Ala Lys Ser Val Cys Gly Pro Val Tyr Cys Phe Thr Pro Ser Pro
            20                  25                  30
```

Val

<210> SEQ ID NO 15
<211> LENGTH: 31
<212> TYPE: PRT
<213> ORGANISM: Hepatitis C virus

<400> SEQUENCE: 15

Pro Ser Pro Val Val Gly Thr Thr Asp Arg Ser Gly Ala Pro Thr
1               5                   10                  15

Tyr Ser Trp Gly Ala Asn Asp Thr Asp Val Phe Val Leu Asn Asn
            20                  25                  30

<210> SEQ ID NO 16
<211> LENGTH: 77
<212> TYPE: PRT
<213> ORGANISM: Hepatitis C virus

<400> SEQUENCE: 16

Ala Gly Ala Leu Val Ala Phe Lys Ile Met Ser Gly Glu Val Pro Ser
1               5                   10                  15

Thr Glu Asp Leu Val Asn Leu Leu Pro Ala Ile Leu Ser Pro Gly Ala
            20                  25                  30

Leu Val Val Gly Val Val Cys Ala Ala Ile Leu Arg Arg His Val Gly
        35                  40                  45

Pro Gly Glu Gly Ala Val Gln Trp Met Asn Arg Leu Ile Ala Phe Ala
    50                  55                  60

Ser Arg Gly Asn His Val Ser Pro Thr His Tyr Val Pro
65                  70                  75

<210> SEQ ID NO 17
<211> LENGTH: 147
<212> TYPE: PRT
<213> ORGANISM: Hepatitis C virus

<400> SEQUENCE: 17

Glu Val Gln Ile Val Ser Thr Ala Thr Gln Thr Phe Leu Ala Thr Cys
1               5                   10                  15

Ile Asn Gly Val Cys Trp Thr Val Tyr His Gly Ala Gly Thr Arg Thr
            20                  25                  30

Ile Ala Ser Pro Lys Gly Pro Val Ile Gln Met Tyr Thr Asn Val Asp
        35                  40                  45

Gln Asp Leu Val Gly Trp Pro Ala Pro Gln Gly Ser Arg Ser Leu Thr
    50                  55                  60

Pro Cys Thr Cys Gly Ser Ser Asp Leu Tyr Leu Val Thr Arg His Ala
65                  70                  75                  80

Asp Val Ile Pro Val Arg Arg Gly Asp Ser Arg Gly Ser Leu Leu
                85                  90                  95

Ser Pro Arg Pro Ile Ser Tyr Leu Lys Gly Ser Ser Gly Gly Pro Leu
            100                 105                 110

Leu Cys Pro Ala Gly His Ala Val Gly Leu Phe Arg Ala Ala Val Cys
        115                 120                 125

Thr Arg Gly Val Ala Lys Ala Val Asp Phe Ile Pro Val Glu Asn Leu
    130                 135                 140

Gly Thr Thr
145

<210> SEQ ID NO 18

```
<211> LENGTH: 36
<212> TYPE: PRT
<213> ORGANISM: Hepatitis C virus

<400> SEQUENCE: 18

Val Thr Gln Leu Leu Arg Arg Leu His Gln Trp Ile Ser Ser Glu Cys
 1               5                  10                  15

Thr Thr Pro Cys Ser Gly Ser Trp Leu Arg Asp Ile Trp Asp Trp Ile
             20                  25                  30

Cys Glu Val Leu
         35

<210> SEQ ID NO 19
<211> LENGTH: 28
<212> TYPE: PRT
<213> ORGANISM: Hepatitis C virus

<400> SEQUENCE: 19

Val Cys Gly Pro Val Tyr Cys Phe Thr Pro Ser Pro Val Val Val Gly
 1               5                  10                  15

Thr Thr Asp Arg Ser Gly Ala Pro Thr Tyr Ser Trp
             20                  25

<210> SEQ ID NO 20
<211> LENGTH: 45
<212> TYPE: PRT
<213> ORGANISM: Hepatitis C virus

<400> SEQUENCE: 20

Pro Pro Leu Arg Ala Trp Arg His Arg Ala Arg Ser Val Arg Ala Arg
 1               5                  10                  15

Leu Leu Ser Arg Gly Gly Arg Ala Ala Ile Cys Gly Lys Tyr Leu Phe
             20                  25                  30

Asn Trp Ala Val Arg Thr Lys Leu Lys Leu Thr Pro Ile
         35                  40                  45

<210> SEQ ID NO 21
<211> LENGTH: 86
<212> TYPE: PRT
<213> ORGANISM: Hepatitis C virus

<400> SEQUENCE: 21

Thr Ala Phe Val Gly Ala Gly Leu Ala Gly Ala Ala Ile Gly Ser Val
 1               5                  10                  15

Gly Leu Gly Lys Val Leu Val Asp Ile Leu Ala Gly Tyr Gly Ala Gly
             20                  25                  30

Val Ala Gly Ala Leu Val Ala Phe Lys Ile Met Ser Gly Glu Val Pro
         35                  40                  45

Ser Thr Glu Asp Leu Val Asn Leu Leu Pro Ala Ile Leu Ser Pro Gly
     50                  55                  60

Ala Leu Val Val Gly Val Val Cys Ala Ala Ile Leu Arg Arg His Val
 65                  70                  75                  80

Gly Pro Gly Glu Gly Ala
                 85

<210> SEQ ID NO 22
<211> LENGTH: 43
<212> TYPE: PRT
<213> ORGANISM: Hepatitis C virus

<400> SEQUENCE: 22
```

```
Gly Ile Val Pro Ala Lys Ser Val Cys Gly Pro Val Tyr Cys Phe Thr
  1               5                  10                  15

Pro Ser Pro Val Val Gly Thr Thr Asp Arg Ser Gly Ala Pro Thr
             20                  25                  30

Tyr Ser Trp Gly Ala Asn Asp Thr Asp Val Phe
         35                  40
```

<210> SEQ ID NO 23
<211> LENGTH: 63
<212> TYPE: PRT
<213> ORGANISM: Hepatitis C virus

<400> SEQUENCE: 23

```
Val Leu Val Asp Ile Leu Ala Gly Tyr Gly Ala Gly Val Ala Gly Ala
  1               5                  10                  15

Leu Val Ala Phe Lys Ile Met Ser Gly Glu Val Pro Ser Thr Glu Asp
             20                  25                  30

Leu Val Asn Leu Leu Pro Ala Ile Leu Ser Pro Gly Ala Leu Val Val
         35                  40                  45

Gly Val Val Cys Ala Ala Ile Leu Arg Arg His Val Gly Pro Gly
     50                  55                  60
```

<210> SEQ ID NO 24
<211> LENGTH: 29
<212> TYPE: PRT
<213> ORGANISM: Hepatitis C virus

<400> SEQUENCE: 24

```
Glu Arg Pro Tyr Cys Trp His Tyr Pro Pro Arg Pro Cys Gly Ile Val
  1               5                  10                  15

Pro Ala Lys Ser Val Cys Gly Pro Val Tyr Cys Phe Thr
             20                  25
```

<210> SEQ ID NO 25
<211> LENGTH: 76
<212> TYPE: PRT
<213> ORGANISM: Hepatitis C virus

<400> SEQUENCE: 25

```
Arg Arg His Trp Thr Thr Gln Asp Cys Asn Cys Ser Ile Tyr Pro Gly
  1               5                  10                  15

His Ile Thr Gly His Arg Met Ala Trp Asp Met Met Met Asn Trp Ser
             20                  25                  30

Pro Thr Ala Ala Leu Val Val Ala Gln Leu Leu Arg Ile Pro Gln Ala
         35                  40                  45

Ile Met Asp Met Ile Ala Gly Ala His Trp Gly Val Leu Ala Gly Ile
     50                  55                  60

Ala Tyr Phe Ser Met Val Gly Asn Trp Ala Lys Val
 65                  70                  75
```

<210> SEQ ID NO 26
<211> LENGTH: 37
<212> TYPE: PRT
<213> ORGANISM: Hepatitis C virus

<400> SEQUENCE: 26

```
Ala Ile Leu Ser Ser Leu Thr Val Thr Gln Leu Leu Arg Arg Leu His
  1               5                  10                  15

Gln Trp Ile Ser Ser Glu Cys Thr Thr Pro Cys Ser Gly Ser Trp Leu
```

Arg Asp Ile Trp Asp
        35

<210> SEQ ID NO 27
<211> LENGTH: 47
<212> TYPE: PRT
<213> ORGANISM: Hepatitis C virus

<400> SEQUENCE: 27

Val Ser Arg Thr Gln Arg Arg Gly Arg Thr Gly Arg Gly Lys Pro Gly
 1               5                  10                  15

Ile Tyr Arg Phe Val Ala Pro Gly Glu Arg Pro Ser Gly Met Phe Asp
            20                  25                  30

Ser Ser Val Leu Cys Glu Cys Tyr Asp Ala Gly Cys Ala Trp Tyr
        35                  40                  45

<210> SEQ ID NO 28
<211> LENGTH: 53
<212> TYPE: PRT
<213> ORGANISM: Hepatitis C virus

<400> SEQUENCE: 28

Leu Pro Ala Pro Asn Tyr Lys Phe Ala Leu Trp Arg Val Ser Ala Glu
 1               5                  10                  15

Glu Tyr Val Glu Ile Arg Arg Val Gly Asp Phe His Tyr Val Ser Gly
            20                  25                  30

Met Thr Thr Asp Asn Leu Lys Cys Pro Cys Gln Ile Pro Ser Pro Glu
        35                  40                  45

Phe Phe Thr Glu Leu
        50

<210> SEQ ID NO 29
<211> LENGTH: 112
<212> TYPE: PRT
<213> ORGANISM: Hepatitis C virus

<400> SEQUENCE: 29

Gly Glu Ile Pro Phe Tyr Gly Lys Ala Ile Pro Leu Glu Val Ile Lys
 1               5                  10                  15

Gly Gly Arg His Leu Ile Phe Cys His Ser Lys Lys Cys Asp Glu
            20                  25                  30

Leu Ala Ala Lys Leu Val Ala Leu Gly Ile Asn Ala Val Ala Tyr Tyr
        35                  40                  45

Arg Gly Leu Asp Val Ser Val Ile Pro Thr Ser Gly Asp Val Val Val
    50                  55                  60

Val Ser Thr Asp Ala Leu Met Thr Gly Phe Thr Gly Asp Phe Asp Ser
65                  70                  75                  80

Val Ile Asp Cys Asn Thr Cys Val Thr Gln Thr Val Asp Phe Ser Leu
                85                  90                  95

Asp Pro Thr Phe Thr Ile Glu Thr Thr Thr Leu Pro Gln Asp Ala Val
            100                 105                 110

<210> SEQ ID NO 30
<211> LENGTH: 54
<212> TYPE: PRT
<213> ORGANISM: Hepatitis C virus

<400> SEQUENCE: 30

```
Val Cys Ala Ala Ile Leu Arg Arg His Val Gly Pro Gly Glu Gly Ala
 1               5                  10                  15

Val Gln Trp Met Asn Arg Leu Ile Ala Phe Ala Ser Arg Gly Asn His
                20                  25                  30

Val Ser Pro Thr His Tyr Val Pro Glu Ser Asp Ala Ala Arg Val
            35                  40                  45

Thr Ala Ile Leu Ser Ser
        50
```

<210> SEQ ID NO 31
<211> LENGTH: 102
<212> TYPE: PRT
<213> ORGANISM: Hepatitis C virus

<400> SEQUENCE: 31

```
Ala Ile Lys Ser Leu Thr Glu Arg Leu Tyr Val Gly Gly Pro Leu Thr
 1               5                  10                  15

Asn Ser Arg Gly Glu Asn Cys Gly Tyr Arg Arg Cys Arg Ala Ser Gly
                20                  25                  30

Val Leu Thr Thr Ser Cys Gly Asn Thr Leu Thr Cys Tyr Ile Lys Ala
            35                  40                  45

Arg Ala Ala Cys Arg Ala Ala Gly Leu Gln Asp Cys Thr Met Leu Val
        50                  55                  60

Cys Gly Asp Asp Leu Val Val Ile Cys Glu Ser Ala Gly Val Gln Glu
 65                  70                  75                  80

Asp Ala Ala Ser Leu Arg Ala Phe Thr Glu Ala Met Thr Arg Tyr Ser
                85                  90                  95

Ala Pro Pro Gly Asp Pro
                100
```

<210> SEQ ID NO 32
<211> LENGTH: 79
<212> TYPE: PRT
<213> ORGANISM: Hepatitis C virus

<400> SEQUENCE: 32

```
Leu Gln Val Leu Asp Ser His Tyr Gln Asp Val Leu Lys Glu Val Lys
 1               5                  10                  15

Ala Ala Ala Ser Lys Val Lys Ala Asn Leu Leu Ser Val Glu Glu Ala
                20                  25                  30

Cys Ser Leu Thr Pro Pro His Ser Ala Lys Ser Lys Phe Gly Tyr Gly
            35                  40                  45

Ala Lys Asp Val Arg Cys His Ala Arg Lys Ala Val Ala His Ile Asn
        50                  55                  60

Ser Val Trp Lys Asp Leu Leu Glu Asp Ser Val Thr Pro Ile Asp
 65                  70                  75
```

<210> SEQ ID NO 33
<211> LENGTH: 61
<212> TYPE: PRT
<213> ORGANISM: Hepatitis C virus

<400> SEQUENCE: 33

```
Thr Gln Thr Val Asp Phe Ser Leu Asp Pro Thr Phe Thr Ile Glu Thr
 1               5                  10                  15

Thr Thr Leu Pro Gln Asp Ala Val Ser Arg Thr Gln Arg Arg Gly Arg
                20                  25                  30

Thr Gly Arg Gly Lys Pro Gly Ile Tyr Arg Phe Val Ala Pro Gly Glu
```

```
                       35                  40                  45

Arg Pro Ser Gly Met Phe Asp Ser Ser Val Leu Cys Glu
      50                  55                  60

<210> SEQ ID NO 34
<211> LENGTH: 77
<212> TYPE: PRT
<213> ORGANISM: Hepatitis C virus

<400> SEQUENCE: 34

Val Leu Asp Ser His Tyr Gln Asp Val Leu Lys Glu Val Lys Ala Ala
 1               5                  10                  15

Ala Ser Lys Val Lys Ala Asn Leu Leu Ser Val Glu Glu Ala Cys Ser
            20                  25                  30

Leu Thr Pro Pro His Ser Ala Lys Ser Lys Phe Gly Tyr Gly Ala Lys
        35                  40                  45

Asp Val Arg Cys His Ala Arg Lys Ala Val Ala His Ile Asn Ser Val
    50                  55                  60

Trp Lys Asp Leu Leu Glu Asp Ser Val Thr Pro Ile Asp
 65                  70                  75

<210> SEQ ID NO 35
<211> LENGTH: 26
<212> TYPE: PRT
<213> ORGANISM: Hepatitis C virus

<400> SEQUENCE: 35

Tyr Pro Pro Arg Pro Cys Gly Ile Val Pro Ala Lys Ser Val Cys Gly
 1               5                  10                  15

Pro Val Tyr Cys Phe Thr Pro Ser Pro Val
            20                  25

<210> SEQ ID NO 36
<211> LENGTH: 37
<212> TYPE: PRT
<213> ORGANISM: Hepatitis C virus

<400> SEQUENCE: 36

Pro Ile Ser Tyr Ala Asn Gly Ser Gly Leu Asp Glu Arg Pro Tyr Cys
 1               5                  10                  15

Trp His Tyr Pro Pro Arg Pro Cys Gly Ile Val Pro Ala Lys Ser Val
            20                  25                  30

Cys Gly Pro Val Tyr
        35

<210> SEQ ID NO 37
<211> LENGTH: 35
<212> TYPE: PRT
<213> ORGANISM: Hepatitis C virus

<400> SEQUENCE: 37

Thr Val Thr Gln Leu Leu Arg Arg Leu His Gln Trp Ile Ser Ser Glu
 1               5                  10                  15

Cys Thr Thr Pro Cys Ser Gly Ser Trp Leu Arg Asp Ile Trp Asp Trp
            20                  25                  30

Ile Cys Glu
        35

<210> SEQ ID NO 38
<211> LENGTH: 25
```

<212> TYPE: PRT
<213> ORGANISM: Hepatitis C virus

<400> SEQUENCE: 38

Leu Leu Arg Arg Leu His Gln Trp Ile Ser Ser Glu Cys Thr Thr Pro
 1               5                  10                  15

Cys Ser Gly Ser Trp Leu Arg Asp Ile
            20                  25

<210> SEQ ID NO 39
<211> LENGTH: 152
<212> TYPE: DNA
<213> ORGANISM: Hepatitis C virus

<400> SEQUENCE: 39
cttgttgccg cgcaggggcc ctagattggg tgtgcgcgcg acgaggaaga cttccgagcg     60
gtcgcaacct cgaggtagac gtcagcctat ccccaaggca cgtcggcccg agggcaggac    120
ctgggctcag cccgggtacc cttggcccct ct                                  152

<210> SEQ ID NO 40
<211> LENGTH: 106
<212> TYPE: DNA
<213> ORGANISM: Hepatitis C virus

<400> SEQUENCE: 40
tggcaggggg aagccaggca tctatagatt tgtggcaccg ggggagcgcc cctccggcat     60
gttcgactcg tccgtcctct gtgagtgcta tgacgcgggc tgtgct                   106

<210> SEQ ID NO 41
<211> LENGTH: 234
<212> TYPE: DNA
<213> ORGANISM: Hepatitis C virus

<400> SEQUENCE: 41
taacaccaac cgtcgcccac aggacgtcaa gttcccgggt ggcggtcaga tcgttggtgg     60
agtttacttg ttgccgcgca ggggccctag attgggtgtg cgcgacgcga ggaagacttc    120
cgagcggtcg caacctcgag gtagacgtca gcctatcccc aaggcacgtc ggcccgaggg    180
caggacctgg gctcagcccg ggtacccttg gcccctctat ggcaatgagg gttg          234

<210> SEQ ID NO 42
<211> LENGTH: 114
<212> TYPE: DNA
<213> ORGANISM: Hepatitis C virus

<400> SEQUENCE: 42
tcccagcccc gtggtggtgg gaacgaccga caggtcgggc gcgcctacct acagctgggg     60
tgcaaatgat acgatgtct tcgtccttaa caacaccagg ccaccgctgg gcaa           114

<210> SEQ ID NO 43
<211> LENGTH: 453
<212> TYPE: DNA
<213> ORGANISM: Hepatitis C virus

<400> SEQUENCE: 43
ctccaggact caacgccggg gcaggactgg caggggaag ccaggcatct atagatttgt     60
ggcaccgggg gagcgcccct ccggcatgtt cgactcgtcc gtcctctgtg agtgctatga    120
cgcgggctgt gcttggtatg agctcacgcc cgccgagact acagttaggc tacgagcgta    180

```
catgaacacc ccggggcttc ccgtgtgcca ggaccatctt gaattttggg agggcgtctt    240
tacgggcctc actcatatag atgcccactt tttatcccag acaaagcaga gtggggagaa    300
ctttccttac ctggtagcgt accaagccac cgtgtgcgct agggctcaag cccctcccccc  360 atcgtgggac cagatgtgga agtgtttgat ccgccttaaa cccaccctcc atgggccaac    420 accccctgcta tacagactgg gcgctgttca gaa                                453
```

<210> SEQ ID NO 44
<211> LENGTH: 85
<212> TYPE: DNA
<213> ORGANISM: Hepatitis C virus

<400> SEQUENCE: 44

```
tcccagcccc gtggtggtgg gaacgaccga caggtcgggc gcgcctacct acagctgggg    60
tgcaaatgat acggatgtct cgtc                                            85
```

<210> SEQ ID NO 45
<211> LENGTH: 80
<212> TYPE: DNA
<213> ORGANISM: Hepatitis C virus

<400> SEQUENCE: 45

```
ccctccaaga ccttgtggca ttgtgcccgc aaagagcgtg tgtggcccgg tatattgctt    60
cactcccagc cccgtggtgg                                                 80
```

<210> SEQ ID NO 46
<211> LENGTH: 165
<212> TYPE: DNA
<213> ORGANISM: Hepatitis C virus

<400> SEQUENCE: 46

```
ctgcgtggtc atagtgggca ggatcgtctt gtccgggaag ccggcaatta tacctgacag    60
ggaggttctc taccaggagt tcgatgagat ggaagagtgc tctcagcact taccgtacat    120
cgagcaaggg atgatgctcg ctgagcagtt caagcagaag gccct                    165
```

<210> SEQ ID NO 47
<211> LENGTH: 123
<212> TYPE: DNA
<213> ORGANISM: Hepatitis C virus

<400> SEQUENCE: 47

```
cggcgacttc gactctgtga tagactgcaa cacgtgtgtc actcagacag tcgatttcag    60 ccttgacccta cctttaccatt gagacaacac cacgctcccc caggatgctg tctccaggac  120
tca                                                                  123
```

<210> SEQ ID NO 48
<211> LENGTH: 87
<212> TYPE: DNA
<213> ORGANISM: Hepatitis C virus

<400> SEQUENCE: 48

```
ggagcgcccc tccggcatgt tcgactcgtc cgtcctctgt gagtgctatg acgcgggctg    60
tgcttggtat gagctcacgc ccgccga                                         87
```

<210> SEQ ID NO 49
<211> LENGTH: 84
<212> TYPE: DNA
<213> ORGANISM: Hepatitis C virus -continued

```
<400> SEQUENCE: 49 caggggggaag ccaggcatct atagatttgt ggcaccgggg gagcgcccct ccggcatgtt        60
cgactcgtcc gtcctctgtg agtg                                                84

<210> SEQ ID NO 50
<211> LENGTH: 128
<212> TYPE: DNA
<213> ORGANISM: Hepatitis C virus

<400> SEQUENCE: 50
tctggaagac agtgtaacac caatagacac taccatcatg ccaagaacg aggttttctg         60 cgttcagcct gagaaggggg gtcgtaagcc agctcgtctc atcgtgttcc ccgacctggg       120
cgtgcgcg                                                                128

<210> SEQ ID NO 51
<211> LENGTH: 85
<212> TYPE: DNA
<213> ORGANISM: Hepatitis C virus

<400> SEQUENCE: 51
tcccaccggc agcggtaaga gcaccaaggt cccggctgcg tacgcagccc agggctacaa        60
ggtgttggtg ctcaacccct ctgtt                                              85

<210> SEQ ID NO 52
<211> LENGTH: 102
<212> TYPE: DNA
<213> ORGANISM: Hepatitis C virus

<400> SEQUENCE: 52
cgaacgcccc tactgctggc actaccctcc aagaccttgt ggcattgtgc ccgcaaagag        60
cgtgtgtggc ccggtatatt gcttcactcc cagccccgtg gt                         102

<210> SEQ ID NO 53
<211> LENGTH: 95
<212> TYPE: DNA
<213> ORGANISM: Hepatitis C virus

<400> SEQUENCE: 53
tcccagcccc gtggtggtgg gaacgaccga caggtcgggc gcgcctacct acagctgggg        60
tgcaaatgat acggatgtct tcgtccttaa caaca                                   95

<210> SEQ ID NO 54
<211> LENGTH: 234
<212> TYPE: DNA
<213> ORGANISM: Hepatitis C virus

<400> SEQUENCE: 54
ggcgggagct cttgtagcat tcaagatcat gagcggtgag gtcccctcca cggaggacct        60
ggtcaatctg ctgcccgcca tcctctcgcc tggagccctt gtagtcggtg tggtctgcgc      120
agcaatactg cgccggcacg ttggcccggg cgagggggca gtgcaatgga tgaaccggct      180
aatagccttc gcctcccggg ggaaccatgt tccccccacg cactacgtgc cgga            234

<210> SEQ ID NO 55
<211> LENGTH: 442
<212> TYPE: DNA
<213> ORGANISM: Hepatitis C virus
```

-continued

```
<400> SEQUENCE: 55
tgaggtccag atcgtgtcaa ctgctaccca aaccttcctg gcaacgtgca tcaatggggt      60
atgctggact gtctaccacg gggccggaac gaggaccatc gcatcaccca agggtcctgt     120
catccagatg tataccaatg tggaccaaga ccttgtgggc tggcccgctc ctcaaggttc     180
ccgctcattg acaccctgta cctgcggctc ctcggacctt tacctggtca cgaggcacgc     240
cgatgtcatt cccgtgcgcc ggcgaggtga tagcagggga gcctgctttt cgccccggcc     300
catttcctac ttgaaaggct cctcgggggg tccgctgttg tgccccgcgg gacacgccgt     360
gggcctattc agggccgcgg tgtgcacccg tggagtggct aaagcggtgg actttatccc     420
tgtggagaac ctagggacaa cc                                              442

<210> SEQ ID NO 56
<211> LENGTH: 111
<212> TYPE: DNA
<213> ORGANISM: Hepatitis C virus

<400> SEQUENCE: 56
tgtaacccag ctcctgaggc gactgcatca gtggataagc tcggagtgta ccactccatg      60
ctccggttcc tggctaaggg acatctggga ctggatatgc gaggtgctga g              111

<210> SEQ ID NO 57
<211> LENGTH: 87
<212> TYPE: DNA
<213> ORGANISM: Hepatitis C virus

<400> SEQUENCE: 57
cgtgtgtggc ccggtatatt gcttcactcc cagccccgtg gtggtgggaa cgaccgacag      60 tcgggcgcg cctacctaca gctgggg                                           87

<210> SEQ ID NO 58
<211> LENGTH: 137
<212> TYPE: DNA
<213> ORGANISM: Hepatitis C virus

<400> SEQUENCE: 58
cccgcccttg cgagcttgga gacaccgggc ccggagcgtc cgcgctaggc ttctgtccag      60
aggaggcagg gctgccatat gtggcaagta cctcttcaac tgggcagtaa gaacaaagct     120
caaactcact ccaatag                                                    137

<210> SEQ ID NO 59
<211> LENGTH: 259
<212> TYPE: DNA
<213> ORGANISM: Hepatitis C virus

<400> SEQUENCE: 59
tactgccttt gtgggtgctg gcctagctgg cgccgccatc ggcagcgttg gactggggaa      60
ggtcctcgtg gacattcttg cagggtatgg cgcgggcgtg gcgggagctc ttgtagcatt     120
caagatcatg agcggtgagg tcccctccac ggaggacctg tcaatctgc tgcccgccat      180 cctctcgcct ggagcccttg tagtcggtgt ggtctgcgca gcaatactgc gccggcacgt     240
tggcccgggc gagggggca                                                  259

<210> SEQ ID NO 60
<211> LENGTH: 130
<212> TYPE: DNA
<213> ORGANISM: Hepatitis C virus
```

```
<400> SEQUENCE: 60
tggcattgtg cccgcaaaga gcgtgtgtgg cccggtatat tgcttcactc ccagccccgt    60
ggtggtggga acgaccgaca ggtcgggcgc gcctacctac agctggggtg caaatgatac   120
ggatgtcttc                                                          130

<210> SEQ ID NO 61
<211> LENGTH: 191
<212> TYPE: DNA
<213> ORGANISM: Hepatitis C virus

<400> SEQUENCE: 61
ggtcctcgtg gacattcttg cagggtatgg cgcgggcgtg gcgggagctc ttgtagcatt    60
caagatcatg agcggtgagg tcccctccac ggaggacctg gtcaatctgc tgcccgccat   120
cctctcgcct ggagcccttg tagtcggtgt ggtctgcgca gcaatactgc gccggcacgt   180
tggcccgggc g                                                        191

<210> SEQ ID NO 62
<211> LENGTH: 89
<212> TYPE: DNA
<213> ORGANISM: Hepatitis C virus

<400> SEQUENCE: 62
cgaacgcccc tactgctggc actaccctcc aagaccttgt ggcattgtgc ccgcaaagag    60
cgtgtgtggc ccggtatatt gcttcactc                                     89

<210> SEQ ID NO 63
<211> LENGTH: 230
<212> TYPE: DNA
<213> ORGANISM: Hepatitis C virus

<400> SEQUENCE: 63
caggcgccac tggacgacgc aagactgcaa ttgttctatc tatcccggcc atataacggg    60
tcatcgcatg gcatgggata tgatgatgaa ctggtcccct acggcagcgt tggtggtagc   120
tcagctgctc cggatcccac aagccatcat ggacatgatc gctggtgctc actggggagt   180
cctggcgggc atagcgtatt tctccatggt ggggaactgg gcgaaggtcc               230

<210> SEQ ID NO 64
<211> LENGTH: 113
<212> TYPE: DNA
<213> ORGANISM: Hepatitis C virus

<400> SEQUENCE: 64
tgccatactc agcagcctca ctgtaaccca gctcctgagg cgactgcatc agtggataag    60
ctcggagtgt accactccat gctccggttc ctggctaagg acatctggg act            113

<210> SEQ ID NO 65
<211> LENGTH: 142
<212> TYPE: DNA
<213> ORGANISM: Hepatitis C virus

<400> SEQUENCE: 65
tgtctccagg actcaacgcc ggggcaggac tggcagggg aagccaggca tctatagatt     60
tgtggcaccg ggggagcgcc cctccggcat gttcgactcg tccgtcctct gtgagtgcta   120
tgacgcgggc tgtgcttggt at                                            142
```

<210> SEQ ID NO 66
<211> LENGTH: 162
<212> TYPE: DNA
<213> ORGANISM: Hepatitis C virus

<400> SEQUENCE: 66

| | | | | | |
|---|---|---|---|---|---|
| ccttcctgcg | ccgaactata | agttcgcgct | gtggagggtg | tctgcagagg | aatacgtgga | 60 |
| gataaggcgg | gtgggggact | tccactacgt | atcgggtatg | actactgaca | atcttaaatg | 120 |
| cccgtgccag | atcccatcgc | ccgaattttt | cacagaattg | ga | | 162 |

<210> SEQ ID NO 67
<211> LENGTH: 337
<212> TYPE: DNA
<213> ORGANISM: Hepatitis C virus

<400> SEQUENCE: 67

| | | | | | |
|---|---|---|---|---|---|
| cggagagatc | cccttttacg | gcaaggctat | cccctcgag | gtgatcaagg | ggggaagaca | 60 |
| tctcatcttc | tgccactcaa | agaagaagtg | cgacgagctc | gccgcgaagc | tggtcgcatt | 120 |
| gggcatcaat | gccgtggcct | actaccgcgg | tcttgacgtg | tctgtcatcc | cgaccagcgg | 180 |
| cgatgttgtc | gtcgtgtcga | ccgatgctct | catgactggc | tttaccggcg | acttcgactc | 240 |
| tgtgatagac | tgcaacacgt | gtgtcactca | gacagtcgat | ttcagccttg | accctacctt | 300 |
| taccattgag | acaaccacgc | tcccccagga | tgctgtc | | | 337 |

<210> SEQ ID NO 68
<211> LENGTH: 163
<212> TYPE: DNA
<213> ORGANISM: Hepatitis C virus

<400> SEQUENCE: 68

| | | | | | |
|---|---|---|---|---|---|
| ggtctgcgca | gcaatactgc | gccggcacgt | tggcccgggc | gaggggggcag | tgcaatggat | 60 |
| gaaccggcta | atagccttcg | cctcccgggg | gaaccatgtt | tccccacgc | actacgtgcc | 120 |
| ggagagcgat | gcagccgccc | gcgtcactgc | catactcagc | agc | | 163 |

<210> SEQ ID NO 69
<211> LENGTH: 309
<212> TYPE: DNA
<213> ORGANISM: Hepatitis C virus

<400> SEQUENCE: 69

| | | | | | |
|---|---|---|---|---|---|
| ggccatcaag | tccctcactg | agaggcttta | tgttggggc | cctcttacca | attcaagggg | 60 |
| ggaaaactgc | ggctaccgca | ggtgccgcgc | gagcggcgta | ctgacaacta | gctgtggtaa | 120 |
| caccctcact | tgctacatca | aggcccgggc | agcctgtcga | gccgcagggc | tccaggactg | 180 |
| caccatgctc | gtgtgtggcg | acgacttagt | cgttatctgt | gaaagtgcgg | gggtccagga | 240 |
| ggacgcggcg | agcctgagag | ccttcacgga | ggctatgacc | aggtactccg | ccccccccgg | 300 |
| ggacccccc | | | | | | 309 |

<210> SEQ ID NO 70
<211> LENGTH: 240
<212> TYPE: DNA
<213> ORGANISM: Hepatitis C virus

<400> SEQUENCE: 70

| | | | | | |
|---|---|---|---|---|---|
| actgcaagtt | ctggacagcc | attaccagga | cgtgctcaag | gaggtcaaag | cagcggcgtc | 60 |
| aaaagtgaag | gctaacttgc | tatccgtaga | ggaagcttgc | agcctgacgc | ccccacattc | 120 |

```
agccaaatcc aagtttggct atggggcaaa agacgtccgt tgccatgcca gaaaggccgt      180
agcccacatc aactccgtgt ggaaagacct tctggaagac agtgtaacac caatagacac      240

<210> SEQ ID NO 71
<211> LENGTH: 184
<212> TYPE: DNA
<213> ORGANISM: Hepatitis C virus

<400> SEQUENCE: 71
cactcagaca gtcgatttca gccttgaccc tacctttacc attgagacaa ccacgctccc      60
ccaggatgct gtctccagga ctcaacgccg gggcaggact ggcaggggga agccaggcat     120
ctatagattt gtggcaccgg gggagcgccc ctccggcatg ttcgactcgt ccgtcctctg     180
tgag                                                                  184

<210> SEQ ID NO 72
<211> LENGTH: 234
<212> TYPE: DNA
<213> ORGANISM: Hepatitis C virus

<400> SEQUENCE: 72
agttctggac agccattacc aggacgtgct caaggaggtc aaagcagcgg cgtcaaaagt      60
gaaggctaac ttgctatccg tagaggaagc ttgcagcctg acgccccac attcagccaa      120 atccaagttt ggctatgggg caaaagacgt ccgttgccat gccagaaagg ccgtagccca     180
catcaactcc gtgtggaaag accttctgga agacagtgta acaccaatag acac           234

<210> SEQ ID NO 73
<211> LENGTH: 80
<212> TYPE: DNA
<213> ORGANISM: Hepatitis C virus

<400> SEQUENCE: 73
ctaccctcca agaccttgtg gcattgtgcc cgcaaagagc gtgtgtggcc cggtatattg      60
cttcactccc agccccgtgg                                                  80

<210> SEQ ID NO 74
<211> LENGTH: 112
<212> TYPE: DNA
<213> ORGANISM: Hepatitis C virus

<400> SEQUENCE: 74
tcctatcagt tatgccaacg gaagcggcct cgacgaacgc ccctactgct ggcactaccc      60
tccaagacct tgtggcattg tgcccgcaaa gagcgtgtgt ggcccggtat at             112

<210> SEQ ID NO 75
<211> LENGTH: 107
<212> TYPE: DNA
<213> ORGANISM: Hepatitis C virus

<400> SEQUENCE: 75
cactgtaacc cagctcctga ggcgactgca tcagtggata agctcggagt gtaccactcc      60
atgctccggt tcctggctaa gggacatctg ggactggata tgcgagg                   107

<210> SEQ ID NO 76
<211> LENGTH: 78
<212> TYPE: DNA
<213> ORGANISM: Hepatitis C virus
```

-continued

```
<400> SEQUENCE: 76
gctcctgagg cgactgcatc agtggataag ctcggagtgt accactccat gctccggttc    60
ctggctaagg gacatctg                                                  78

<210> SEQ ID NO 77
<211> LENGTH: 103
<212> TYPE: PRT
<213> ORGANISM: Hepatitis C virus

<400> SEQUENCE: 77
```

Ala Cys Glu Cys Pro Gly Arg Ser Arg Arg Pro Cys Thr Met Ser Thr
 1               5                  10                  15

Asn Pro Lys Pro Gln Arg Lys Thr Lys Arg Asn Thr Asn Arg Arg Pro
            20                  25                  30

Gln Asp Val Lys Phe Pro Gly Gly Gly Gln Ile Val Gly Gly Val Tyr
        35                  40                  45

Leu Leu Pro Arg Arg Gly Pro Arg Leu Gly Val Arg Ala Thr Arg Lys
    50                  55                  60

Thr Ser Glu Arg Ser Gln Pro Arg Gly Arg Arg Gln Pro Ile Pro Lys
65                  70                  75                  80

Ala Arg Arg Pro Glu Gly Arg Thr Trp Ala Gln Pro Gly Tyr Pro Trp
                85                  90                  95

Pro Leu Tyr Gly Asn Glu Gly
            100

```
<210> SEQ ID NO 78
<211> LENGTH: 113
<212> TYPE: PRT
<213> ORGANISM: Hepatitis C virus

<400> SEQUENCE: 78
```

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg

```
<210> SEQ ID NO 79
<211> LENGTH: 114
<212> TYPE: PRT
<213> ORGANISM: Hepatitis C virus

<400> SEQUENCE: 79
```

Ala Ile Leu His Thr Pro Gly Cys Val Pro Cys Val Arg Glu Gly Asn
 1               5                  10                  15

Ala Ser Arg Cys Trp Val Ala Val Thr Pro Thr Val Ala Thr Arg Asp
            20                  25                  30

-continued

Gly Lys Leu Pro Thr Thr Gln Leu Arg Arg His Ile Asp Leu Leu Val
            35                  40                  45

Gly Ser Ala Thr Leu Cys Ser Ala Leu Tyr Val Gly Asp Leu Cys Gly
        50                  55                  60

Ser Val Phe Leu Val Gly Gln Leu Phe Thr Phe Ser Pro Arg Arg His
65                  70                  75                  80

Trp Thr Thr Gln Asp Cys Asn Cys Ser Ile Tyr Pro Gly His Ile Thr
                85                  90                  95

Gly His Arg Met Ala Trp Asp Met Met Met Asn Trp Ser Pro Thr Ala
                100                 105                 110

Ala Leu

<210> SEQ ID NO 80
<211> LENGTH: 91
<212> TYPE: PRT
<213> ORGANISM: Hepatitis C virus

<400> SEQUENCE: 80

Gly Val Asp Ala Glu Thr His Val Thr Gly Gly Asn Ala Gly Arg Thr
1               5                   10                  15

Thr Ala Gly Leu Val Gly Leu Leu Thr Pro Gly Ala Lys Gln Asn Ile
            20                  25                  30

Gln Leu Ile Asn Thr Asn Gly Ser Trp His Ile Asn Ser Thr Ala Leu
        35                  40                  45

Asn Cys Asn Glu Ser Leu Asn Thr Gly Trp Leu Ala Gly Leu Phe Tyr
    50                  55                  60

Gln His Lys Phe Asn Ser Ser Gly Cys Pro Glu Arg Leu Ala Ser Cys
65                  70                  75                  80

Arg Arg Leu Thr Asp Phe Ala Gln Gly Trp Gly
                85                  90

<210> SEQ ID NO 81
<211> LENGTH: 176
<212> TYPE: PRT
<213> ORGANISM: Hepatitis C virus

<400> SEQUENCE: 81

Trp Gly Pro Ile Ser Tyr Ala Asn Gly Ser Gly Leu Asp Glu Arg Pro
1               5                   10                  15

Tyr Cys Trp His Tyr Pro Pro Arg Pro Cys Gly Ile Val Pro Ala Lys
            20                  25                  30

Ser Val Cys Gly Pro Val Tyr Cys Phe Thr Pro Ser Pro Val Val Val
        35                  40                  45

Gly Thr Thr Asp Arg Ser Gly Ala Pro Thr Tyr Ser Trp Gly Ala Asn
    50                  55                  60

Asp Thr Asp Val Phe Val Leu Asn Asn Thr Arg Pro Pro Leu Gly Asn
65                  70                  75                  80

Trp Phe Gly Cys Thr Trp Met Asn Ser Thr Gly Phe Thr Lys Val Cys
                85                  90                  95

Gly Ala Pro Pro Cys Val Ile Gly Gly Val Gly Asn Asn Thr Leu Leu
                100                 105                 110

Cys Pro Thr Asp Cys Phe Arg Lys His Pro Glu Ala Thr Tyr Ser Arg
            115                 120                 125

Cys Gly Ser Gly Pro Trp Ile Thr Pro Arg Cys Met Val Asp Tyr Pro
        130                 135                 140

```
Tyr Arg Leu Trp His Tyr Pro Cys Thr Ile Asn Tyr Thr Ile Phe Lys
145                 150                 155                 160

Val Arg Met Tyr Val Gly Val Glu His Arg Leu Glu Ala Ala Cys
                165                 170                 175

<210> SEQ ID NO 82
<211> LENGTH: 96
<212> TYPE: PRT
<213> ORGANISM: Hepatitis C virus

<400> SEQUENCE: 82

Trp His Tyr Pro Pro Arg Pro Cys Gly Ile Val Pro Ala Lys Ser Val
1               5                   10                  15

Cys Gly Pro Val Tyr Cys Phe Thr Pro Ser Pro Val Val Gly Thr
                20                  25                  30

Thr Asp Arg Ser Gly Ala Pro Thr Tyr Ser Trp Gly Ala Asn Asp Thr
                35                  40                  45

Asp Val Phe Val Leu Asn Asn Thr Arg Pro Pro Leu Gly Asn Trp Phe
            50                  55                  60

Gly Cys Thr Trp Met Asn Ser Thr Gly Phe Thr Lys Val Cys Gly Ala
65                  70                  75                  80

Pro Pro Cys Val Ile Gly Gly Val Gly Asn Asn Thr Leu Leu Cys Pro
                85                  90                  95

<210> SEQ ID NO 83
<211> LENGTH: 278
<212> TYPE: PRT
<213> ORGANISM: Hepatitis C virus

<400> SEQUENCE: 83

Ala Ala Cys Gly Asp Ile Ile Asn Gly Leu Pro Val Ser Ala Arg Arg
1               5                   10                  15

Gly Gln Glu Ile Leu Leu Gly Pro Ala Asp Gly Met Val Ser Lys Gly
                20                  25                  30

Trp Arg Leu Leu Ala Pro Ile Thr Ala Tyr Ala Gln Gln Thr Arg Gly
            35                  40                  45

Leu Leu Gly Cys Ile Ile Thr Ser Leu Thr Gly Arg Asp Lys Asn Gln
50                  55                  60

Val Glu Gly Glu Val Gln Ile Val Ser Thr Ala Thr Gln Thr Phe Leu
65                  70                  75                  80

Ala Thr Cys Ile Asn Gly Val Cys Trp Thr Val Tyr His Gly Ala Gly
                85                  90                  95

Thr Arg Thr Ile Ala Ser Pro Lys Gly Pro Val Ile Gln Met Tyr Thr
                100                 105                 110

Asn Val Asp Gln Asp Leu Val Gly Trp Pro Ala Pro Gln Gly Ser Arg
            115                 120                 125

Ser Leu Thr Pro Cys Thr Cys Gly Ser Ser Asp Leu Tyr Leu Val Thr
            130                 135                 140

Arg His Ala Asp Val Ile Pro Val Arg Arg Arg Gly Asp Ser Arg Gly
145                 150                 155                 160

Ser Leu Leu Ser Pro Arg Pro Ile Ser Tyr Leu Lys Gly Ser Ser Gly
                165                 170                 175

Gly Pro Leu Leu Cys Pro Ala Gly His Ala Val Gly Leu Phe Arg Ala
                180                 185                 190

Ala Val Cys Thr Arg Gly Val Ala Lys Ala Val Asp Phe Ile Pro Val
                195                 200                 205
```

```
Glu Asn Leu Gly Thr Thr Met Arg Ser Pro Val Phe Thr Asp Asn Ser
    210                 215                 220
Ser Pro Pro Ala Val Pro Gln Ser Phe Gln Val Ala His Leu His Ala
225                 230                 235                 240
Pro Thr Gly Ser Gly Lys Ser Thr Lys Val Pro Ala Ala Tyr Ala Ala
                245                 250                 255
Gln Gly Tyr Lys Val Leu Val Leu Asn Pro Ser Val Ala Ala Thr Leu
            260                 265                 270
Gly Phe Gly Ala Tyr Met
        275

<210> SEQ ID NO 84
<211> LENGTH: 158
<212> TYPE: PRT
<213> ORGANISM: Hepatitis C virus

<400> SEQUENCE: 84

Arg Arg Arg Gly Asp Ser Arg Gly Ser Leu Leu Ser Pro Arg Pro Ile
  1               5                  10                  15
Ser Tyr Leu Lys Gly Ser Ser Gly Gly Pro Leu Leu Cys Pro Ala Gly
             20                  25                  30
His Ala Val Gly Leu Phe Arg Ala Ala Val Cys Thr Arg Gly Val Ala
         35                  40                  45
Lys Ala Val Asp Phe Ile Pro Val Glu Asn Leu Gly Thr Thr Met Arg
     50                  55                  60
Ser Pro Val Phe Thr Asp Asn Ser Ser Pro Pro Ala Val Pro Gln Ser
 65                  70                  75                  80
Phe Gln Val Ala His Leu His Ala Pro Thr Gly Ser Gly Lys Ser Thr
                 85                  90                  95
Lys Val Pro Ala Ala Tyr Ala Ala Gln Gly Tyr Lys Val Leu Val Leu
            100                 105                 110
Asn Pro Ser Val Ala Ala Thr Leu Gly Phe Gly Ala Tyr Met Ser Lys
        115                 120                 125
Ala His Gly Val Asp Pro Asn Ile Arg Thr Gly Val Arg Thr Ile Thr
    130                 135                 140
Thr Gly Ser Pro Ile Thr Tyr Ser Thr Tyr Gly Lys Phe Leu
145                 150                 155

<210> SEQ ID NO 85
<211> LENGTH: 263
<212> TYPE: PRT
<213> ORGANISM: Hepatitis C virus

<400> SEQUENCE: 85

Asp Ser Arg Gly Ser Leu Leu Ser Pro Arg Pro Ile Ser Tyr Leu Lys
  1               5                  10                  15
Gly Ser Ser Gly Gly Pro Leu Leu Cys Pro Ala Gly His Ala Val Gly
             20                  25                  30
Leu Phe Arg Ala Ala Val Cys Thr Arg Gly Val Ala Lys Ala Val Asp
         35                  40                  45
Phe Ile Pro Val Glu Asn Leu Gly Thr Thr Met Arg Ser Pro Val Phe
     50                  55                  60
Thr Asp Asn Ser Ser Pro Pro Ala Val Pro Gln Ser Phe Gln Val Ala
 65                  70                  75                  80
His Leu His Ala Pro Thr Gly Ser Gly Lys Ser Thr Lys Val Pro Ala
                 85                  90                  95
```

```
Ala Tyr Ala Ala Gln Gly Tyr Lys Val Leu Val Leu Asn Pro Ser Val
            100                 105                 110

Ala Ala Thr Leu Gly Phe Gly Ala Tyr Met Ser Lys Ala His Gly Val
        115                 120                 125

Asp Pro Asn Ile Arg Thr Gly Val Arg Thr Ile Thr Thr Gly Ser Pro
    130                 135                 140

Ile Thr Tyr Ser Thr Tyr Gly Lys Phe Leu Ala Asp Gly Gly Cys Ser
145                 150                 155                 160

Gly Gly Ala Tyr Asp Ile Ile Ile Cys Asp Glu Cys His Ser Thr Asp
            165                 170                 175

Ala Thr Ser Ile Leu Gly Ile Gly Thr Val Leu Asp Gln Ala Glu Thr
        180                 185                 190

Ala Gly Ala Arg Leu Val Val Leu Ala Thr Ala Thr Pro Pro Gly Ser
    195                 200                 205

Val Thr Val Ser His Pro Asn Ile Glu Glu Val Ala Leu Ser Thr Thr
210                 215                 220

Gly Glu Ile Pro Phe Tyr Gly Lys Ala Ile Pro Leu Glu Val Ile Lys
225                 230                 235                 240

Gly Gly Arg His Leu Ile Phe Cys His Ser Lys Lys Lys Cys Asp Glu
            245                 250                 255

Leu Ala Ala Lys Leu Val Ala
            260

<210> SEQ ID NO 86
<211> LENGTH: 194
<212> TYPE: PRT
<213> ORGANISM: Hepatitis C virus

<400> SEQUENCE: 86

Asp Asn Ser Ser Pro Pro Ala Val Pro Gln Ser Phe Gln Val Ala His
  1               5                  10                  15

Leu His Ala Pro Thr Gly Ser Gly Lys Ser Thr Lys Val Pro Ala Ala
             20                  25                  30

Tyr Ala Ala Gln Gly Tyr Lys Val Leu Val Leu Asn Pro Ser Val Ala
         35                  40                  45

Ala Thr Leu Gly Phe Gly Ala Tyr Met Ser Lys Ala His Gly Val Asp
     50                  55                  60

Pro Asn Ile Arg Thr Gly Val Arg Thr Ile Thr Thr Gly Ser Pro Ile
65                  70                  75                  80

Thr Tyr Ser Thr Tyr Gly Lys Phe Leu Ala Asp Gly Gly Cys Ser Gly
             85                  90                  95

Gly Ala Tyr Asp Ile Ile Ile Cys Asp Glu Cys His Ser Thr Asp Ala
            100                 105                 110

Thr Ser Ile Leu Gly Ile Gly Thr Val Leu Asp Gln Ala Glu Thr Ala
        115                 120                 125

Gly Ala Arg Leu Val Val Leu Ala Thr Ala Thr Pro Pro Gly Ser Val
    130                 135                 140

Thr Val Ser His Pro Asn Ile Glu Glu Val Ala Leu Ser Thr Thr Gly
145                 150                 155                 160

Glu Ile Pro Phe Tyr Gly Lys Ala Ile Pro Leu Glu Val Ile Lys Gly
            165                 170                 175

Gly Arg His Leu Ile Phe Cys His Ser Lys Lys Lys Cys Asp Glu Leu
        180                 185                 190

Ala Ala
```

```
<210> SEQ ID NO 87
<211> LENGTH: 205
<212> TYPE: PRT
<213> ORGANISM: Hepatitis C virus

<400> SEQUENCE: 87

Leu Ala Asp Gly Gly Cys Ser Gly Gly Ala Tyr Asp Ile Ile Ile Cys
 1               5                  10                  15

Asp Glu Cys His Ser Thr Asp Ala Thr Ser Ile Leu Gly Ile Gly Thr
            20                  25                  30

Val Leu Asp Gln Ala Glu Thr Ala Gly Ala Arg Leu Val Val Leu Ala
        35                  40                  45

Thr Ala Thr Pro Pro Gly Ser Val Thr Val Ser His Pro Asn Ile Glu
    50                  55                  60

Glu Val Ala Leu Ser Thr Thr Gly Glu Ile Pro Phe Tyr Gly Lys Ala
65                  70                  75                  80

Ile Pro Leu Glu Val Ile Lys Gly Gly Arg His Leu Ile Phe Cys His
                85                  90                  95

Ser Lys Lys Lys Cys Asp Glu Leu Ala Ala Lys Leu Val Ala Leu Gly
            100                 105                 110

Ile Asn Ala Val Ala Tyr Tyr Arg Gly Leu Asp Val Ser Val Ile Pro
        115                 120                 125

Thr Ser Gly Asp Val Val Val Ser Thr Asp Ala Leu Met Thr Gly
    130                 135                 140

Phe Thr Gly Asp Phe Asp Ser Val Ile Asp Cys Asn Thr Cys Val Thr
145                 150                 155                 160

Gln Thr Val Asp Phe Ser Leu Asp Pro Thr Phe Thr Ile Glu Thr Thr
                165                 170                 175

Thr Leu Pro Gln Asp Ala Val Ser Arg Thr Gln Arg Arg Gly Arg Thr
            180                 185                 190

Gly Arg Gly Lys Pro Gly Ile Tyr Arg Phe Val Ala Pro
        195                 200                 205

<210> SEQ ID NO 88
<211> LENGTH: 186
<212> TYPE: PRT
<213> ORGANISM: Hepatitis C virus

<400> SEQUENCE: 88

Ser Thr Asp Ala Thr Ser Ile Leu Gly Ile Gly Thr Val Leu Asp Gln
 1               5                  10                  15

Ala Glu Thr Ala Gly Ala Arg Leu Val Val Leu Ala Thr Ala Thr Pro
            20                  25                  30

Pro Gly Ser Val Thr Val Ser His Pro Asn Ile Glu Glu Val Ala Leu
        35                  40                  45

Ser Thr Thr Gly Glu Ile Pro Phe Tyr Gly Lys Ala Ile Pro Leu Glu
    50                  55                  60

Val Ile Lys Gly Gly Arg His Leu Ile Phe Cys His Ser Lys Lys Lys
65                  70                  75                  80

Cys Asp Glu Leu Ala Ala Lys Leu Val Ala Leu Gly Ile Asn Ala Val
                85                  90                  95

Ala Tyr Tyr Arg Gly Leu Asp Val Ser Val Ile Pro Thr Ser Gly Asp
            100                 105                 110

Val Val Val Ser Thr Asp Ala Leu Met Thr Gly Phe Thr Gly Asp
        115                 120                 125
```

```
Phe Asp Ser Val Ile Asp Cys Asn Thr Cys Val Thr Gln Thr Val Asp
         130                 135                 140
Phe Ser Leu Asp Pro Thr Phe Thr Ile Glu Thr Thr Thr Leu Pro Gln
145                 150                 155                 160
Asp Ala Val Ser Arg Thr Gln Arg Arg Gly Arg Thr Gly Arg Gly Lys
                165                 170                 175
Pro Gly Ile Tyr Arg Phe Val Ala Pro Gly
            180                 185

<210> SEQ ID NO 89
<211> LENGTH: 158
<212> TYPE: PRT
<213> ORGANISM: Hepatitis C virus

<400> SEQUENCE: 89

Val Ile Asp Cys Asn Thr Cys Val Thr Gln Thr Val Asp Phe Ser Leu
  1               5                  10                  15
Asp Pro Thr Phe Thr Ile Glu Thr Thr Thr Leu Pro Gln Asp Ala Val
                 20                  25                  30
Ser Arg Thr Gln Arg Arg Gly Arg Thr Gly Arg Gly Lys Pro Gly Ile
             35                  40                  45
Tyr Arg Phe Val Ala Pro Gly Glu Arg Pro Ser Gly Met Phe Asp Ser
         50                  55                  60
Ser Val Leu Cys Glu Cys Tyr Asp Ala Gly Cys Ala Trp Tyr Glu Leu
 65                  70                  75                  80
Thr Pro Ala Glu Thr Thr Val Arg Leu Arg Ala Tyr Met Asn Thr Pro
                 85                  90                  95
Gly Leu Pro Val Cys Gln Asp His Leu Glu Phe Trp Glu Gly Val Phe
            100                 105                 110
Thr Gly Leu Thr His Ile Asp Ala His Phe Leu Ser Gln Thr Lys Gln
        115                 120                 125
Ser Gly Glu Asn Phe Pro Tyr Leu Val Ala Tyr Gln Ala Thr Val Cys
    130                 135                 140
Ala Arg Ala Gln Ala Pro Pro Pro Ser Trp Asp Gln Met Trp
145                 150                 155

<210> SEQ ID NO 90
<211> LENGTH: 129
<212> TYPE: PRT
<213> ORGANISM: Hepatitis C virus

<400> SEQUENCE: 90

Arg Phe Val Ala Pro Gly Glu Arg Pro Ser Gly Met Phe Asp Ser Ser
  1               5                  10                  15
Val Leu Cys Glu Cys Tyr Asp Ala Gly Cys Ala Trp Tyr Glu Leu Thr
                 20                  25                  30
Pro Ala Glu Thr Thr Val Arg Leu Arg Ala Tyr Met Asn Thr Pro Gly
             35                  40                  45
Leu Pro Val Cys Gln Asp His Leu Glu Phe Trp Glu Gly Val Phe Thr
         50                  55                  60
Gly Leu Thr His Ile Asp Ala His Phe Leu Ser Gln Thr Lys Gln Ser
 65                  70                  75                  80
Gly Glu Asn Phe Pro Tyr Leu Val Ala Tyr Gln Ala Thr Val Cys Ala
                 85                  90                  95
Arg Ala Gln Ala Pro Pro Pro Ser Trp Asp Gln Met Trp Lys Cys Leu
            100                 105                 110
```

-continued

```
Ile Arg Leu Lys Pro Thr Leu His Gly Pro Thr Pro Leu Leu Tyr Arg
        115                 120                 125
Leu

<210> SEQ ID NO 91
<211> LENGTH: 51
<212> TYPE: PRT
<213> ORGANISM: Hepatitis C virus

<400> SEQUENCE: 91

Thr Ser Thr Trp Val Leu Val Gly Gly Val Leu Ala Ala Leu Ala Ala
  1               5                  10                  15

Tyr Cys Leu Ser Thr Gly Cys Val Val Ile Val Gly Arg Ile Val Leu
             20                  25                  30

Ser Gly Lys Pro Ala Ile Ile Pro Asp Arg Glu Val Leu Tyr Gln Glu
         35                  40                  45

Phe Asp Glu
     50

<210> SEQ ID NO 92
<211> LENGTH: 18
<212> TYPE: PRT
<213> ORGANISM: Hepatitis C virus

<400> SEQUENCE: 92

Ala Ala Leu Ala Ala Tyr Cys Leu Ser Thr Gly Cys Val Val Ile Val
  1               5                  10                  15

Gly Arg

<210> SEQ ID NO 93
<211> LENGTH: 208
<212> TYPE: PRT
<213> ORGANISM: Hepatitis C virus

<400> SEQUENCE: 93

Phe Thr Ala Ala Val Thr Ser Pro Leu Thr Thr Gly Gln Thr Leu Leu
  1               5                  10                  15

Phe Asn Ile Leu Gly Gly Trp Val Ala Ala Gln Leu Ala Ala Pro Gly
             20                  25                  30

Ala Ala Thr Ala Phe Val Gly Ala Gly Leu Ala Gly Ala Ala Ile Gly
         35                  40                  45

Ser Val Gly Leu Gly Lys Val Leu Val Asp Ile Leu Ala Gly Tyr Gly
     50                  55                  60

Ala Gly Val Ala Gly Ala Leu Val Ala Phe Lys Ile Met Ser Gly Glu
 65                  70                  75                  80

Val Pro Ser Thr Glu Asp Leu Val Asn Leu Leu Pro Ala Ile Leu Ser
                 85                  90                  95

Pro Gly Ala Leu Val Val Gly Val Cys Ala Ala Ile Leu Arg Arg
            100                 105                 110

His Val Gly Pro Gly Glu Gly Ala Val Gln Trp Met Asn Arg Leu Ile
        115                 120                 125

Ala Phe Ala Ser Arg Gly Asn His Val Ser Pro Thr His Tyr Val Pro
    130                 135                 140

Glu Ser Asp Ala Ala Ala Arg Val Thr Ala Ile Leu Ser Ser Leu Thr
145                 150                 155                 160

Val Thr Gln Leu Leu Arg Arg Leu His Gln Trp Ile Ser Ser Glu Cys
                165                 170                 175
```

```
Thr Thr Pro Cys Ser Gly Ser Trp Leu Arg Asp Ile Trp Asp Trp Ile
            180                 185                 190

Cys Glu Val Leu Ser Asp Phe Lys Thr Trp Leu Lys Ala Lys Leu Met
        195                 200                 205
```

<210> SEQ ID NO 94
<211> LENGTH: 207
<212> TYPE: PRT
<213> ORGANISM: Hepatitis C virus

<400> SEQUENCE: 94

```
Thr Ala Phe Val Gly Ala Gly Leu Ala Gly Ala Ala Ile Gly Ser Val
 1               5                  10                  15

Gly Leu Gly Lys Val Leu Val Asp Ile Leu Ala Gly Tyr Gly Ala Gly
            20                  25                  30

Val Ala Gly Ala Leu Val Ala Phe Lys Ile Met Ser Gly Glu Val Pro
        35                  40                  45

Ser Thr Glu Asp Leu Val Asn Leu Leu Pro Ala Ile Leu Ser Pro Gly
 50                  55                  60

Ala Leu Val Val Gly Val Val Cys Ala Ala Ile Leu Arg Arg His Val
65                  70                  75                  80

Gly Pro Gly Glu Gly Ala Val Gln Trp Met Asn Arg Leu Ile Ala Phe
            85                  90                  95

Ala Ser Arg Gly Asn His Val Ser Pro Thr His Tyr Val Pro Glu Ser
        100                 105                 110

Asp Ala Ala Ala Arg Val Thr Ala Ile Leu Ser Ser Leu Thr Val Thr
    115                 120                 125

Gln Leu Leu Arg Arg Leu His Gln Trp Ile Ser Ser Glu Cys Thr Thr
130                 135                 140

Pro Cys Ser Gly Ser Trp Leu Arg Asp Ile Trp Asp Trp Ile Cys Glu
145                 150                 155                 160

Val Leu Ser Asp Phe Lys Thr Trp Leu Lys Ala Lys Leu Met Pro Gln
            165                 170                 175

Leu Pro Gly Ile Pro Phe Val Ser Cys Gln Arg Gly Tyr Arg Gly Val
        180                 185                 190

Trp Arg Gly Asp Gly Ile Met His Thr Arg Cys His Cys Gly Ala
    195                 200                 205
```

<210> SEQ ID NO 95
<211> LENGTH: 225
<212> TYPE: PRT
<213> ORGANISM: Hepatitis C virus

<400> SEQUENCE: 95

```
Leu Val Asp Ile Leu Ala Gly Tyr Gly Ala Gly Val Ala Gly Ala Leu
 1               5                  10                  15

Val Ala Phe Lys Ile Met Ser Gly Glu Val Pro Ser Thr Glu Asp Leu
            20                  25                  30

Val Asn Leu Leu Pro Ala Ile Leu Ser Pro Gly Ala Leu Val Val Gly
        35                  40                  45

Val Val Cys Ala Ala Ile Leu Arg Arg His Val Gly Pro Gly Glu Gly
    50                  55                  60

Ala Val Gln Trp Met Asn Arg Leu Ile Ala Phe Ala Ser Arg Gly Asn
65                  70                  75                  80

His Val Ser Pro Thr His Tyr Val Pro Glu Ser Asp Ala Ala Ala Arg
            85                  90                  95
```

```
Val Thr Ala Ile Leu Ser Ser Leu Thr Val Thr Gln Leu Leu Arg Arg
            100                 105                 110
Leu His Gln Trp Ile Ser Ser Glu Cys Thr Thr Pro Cys Ser Gly Ser
            115                 120                 125
Trp Leu Arg Asp Ile Trp Asp Trp Ile Cys Glu Val Leu Ser Asp Phe
        130                 135                 140
Lys Thr Trp Leu Lys Ala Lys Leu Met Pro Gln Leu Pro Gly Ile Pro
145                 150                 155                 160
Phe Val Ser Cys Gln Arg Gly Tyr Arg Gly Val Trp Arg Gly Asp Gly
                165                 170                 175
Ile Met His Thr Arg Cys His Cys Gly Ala Glu Ile Thr Gly His Val
            180                 185                 190
Lys Asn Gly Thr Met Arg Ile Val Gly Pro Arg Thr Cys Arg Asn Met
            195                 200                 205
Trp Ser Gly Thr Phe Pro Ile Asn Ala Tyr Thr Thr Gly Pro Cys Thr
        210                 215                 220
Pro
225

<210> SEQ ID NO 96
<211> LENGTH: 145
<212> TYPE: PRT
<213> ORGANISM: Hepatitis C virus

<400> SEQUENCE: 96

Ala Gly Tyr Gly Ala Gly Val Ala Gly Ala Leu Val Ala Phe Lys Ile
  1               5                  10                  15
Met Ser Gly Glu Val Pro Ser Thr Glu Asp Leu Val Asn Leu Leu Pro
             20                  25                  30
Ala Ile Leu Ser Pro Gly Ala Leu Val Val Gly Val Val Cys Ala Ala
         35                  40                  45
Ile Leu Arg Arg His Val Gly Pro Gly Glu Gly Ala Val Gln Trp Met
     50                  55                  60
Asn Arg Leu Ile Ala Phe Ala Ser Arg Gly Asn His Val Ser Pro Thr
 65                  70                  75                  80
His Tyr Val Pro Glu Ser Asp Ala Ala Ala Arg Val Thr Ala Ile Leu
                 85                  90                  95
Ser Ser Leu Thr Val Thr Gln Leu Leu Arg Arg Leu His Gln Trp Ile
            100                 105                 110
Ser Ser Glu Cys Thr Thr Pro Cys Ser Gly Ser Trp Leu Arg Asp Ile
            115                 120                 125
Trp Asp Trp Ile Cys Glu Val Leu Ser Asp Phe Lys Thr Trp Leu Lys
        130                 135                 140
Ala
145

<210> SEQ ID NO 97
<211> LENGTH: 54
<212> TYPE: PRT
<213> ORGANISM: Hepatitis C virus

<400> SEQUENCE: 97

Ala Leu Val Val Gly Val Val Cys Ala Ala Ile Leu Arg Arg His Val
  1               5                  10                  15
Gly Pro Gly Glu Gly Ala Val Gln Trp Met Asn Arg Leu Ile Ala Phe
             20                  25                  30
```

Ala Ser Arg Gly Asn His Val Ser Pro Thr His Tyr Val Pro Glu Ser
                35                  40                  45

Asp Ala Ala Arg Val
    50

<210> SEQ ID NO 98
<211> LENGTH: 165
<212> TYPE: PRT
<213> ORGANISM: Hepatitis C virus

<400> SEQUENCE: 98

Ala Ser Arg Gly Asn His Val Ser Pro Thr His Tyr Val Pro Glu Ser
  1               5                  10                  15

Asp Ala Ala Arg Val Thr Ala Ile Leu Ser Ser Leu Thr Val Thr
                20                  25                  30

Gln Leu Leu Arg Arg Leu His Gln Trp Ile Ser Ser Glu Cys Thr Thr
                35                  40                  45

Pro Cys Ser Gly Ser Trp Leu Arg Asp Ile Trp Asp Trp Ile Cys Glu
    50                  55                  60

Val Leu Ser Asp Phe Lys Thr Trp Leu Lys Ala Lys Leu Met Pro Gln
 65                  70                  75                  80

Leu Pro Gly Ile Pro Phe Val Ser Cys Gln Arg Gly Tyr Arg Gly Val
                85                  90                  95

Trp Arg Gly Asp Gly Ile Met His Thr Arg Cys His Cys Gly Ala Glu
               100                 105                 110

Ile Thr Gly His Val Lys Asn Gly Thr Met Arg Ile Val Gly Pro Arg
               115                 120                 125

Thr Cys Arg Asn Met Trp Ser Gly Thr Phe Pro Ile Asn Ala Tyr Thr
   130                 135                 140

Thr Gly Pro Cys Thr Pro Leu Pro Ala Pro Asn Tyr Lys Phe Ala Leu
145                 150                 155                 160

Trp Arg Val Ser Ala
                165

<210> SEQ ID NO 99
<211> LENGTH: 308
<212> TYPE: PRT
<213> ORGANISM: Hepatitis C virus

<400> SEQUENCE: 99

Tyr Val Pro Glu Ser Asp Ala Ala Arg Val Thr Ala Ile Leu Ser
  1               5                  10                  15

Ser Leu Thr Val Thr Gln Leu Leu Arg Arg Leu His Gln Trp Ile Ser
                20                  25                  30

Ser Glu Cys Thr Thr Pro Cys Ser Gly Ser Trp Leu Arg Asp Ile Trp
                35                  40                  45

Asp Trp Ile Cys Glu Val Leu Ser Asp Phe Lys Thr Trp Leu Lys Ala
    50                  55                  60

Lys Leu Met Pro Gln Leu Pro Gly Ile Pro Phe Val Ser Cys Gln Arg
 65                  70                  75                  80

Gly Tyr Arg Gly Val Trp Arg Gly Asp Gly Ile Met His Thr Arg Cys
                85                  90                  95

His Cys Gly Ala Glu Ile Thr Gly His Val Lys Asn Gly Thr Met Arg
               100                 105                 110

Ile Val Gly Pro Arg Thr Cys Arg Asn Met Trp Ser Gly Thr Phe Pro
               115                 120                 125

```
Ile Asn Ala Tyr Thr Thr Gly Pro Cys Thr Pro Leu Pro Ala Pro Asn
    130                 135                 140

Tyr Lys Phe Ala Leu Trp Arg Val Ser Ala Glu Glu Tyr Val Glu Ile
145                 150                 155                 160

Arg Arg Val Gly Asp Phe His Tyr Val Ser Gly Met Thr Thr Asp Asn
                165                 170                 175

Leu Lys Cys Pro Cys Gln Ile Pro Ser Pro Glu Phe Phe Thr Glu Leu
            180                 185                 190

Asp Gly Val Arg Leu His Arg Phe Ala Pro Pro Cys Lys Pro Leu Leu
        195                 200                 205

Arg Glu Glu Val Ser Phe Arg Val Gly Leu His Glu Tyr Pro Val Gly
210                 215                 220

Ser Gln Leu Pro Cys Glu Pro Glu Pro Asp Val Ala Val Leu Thr Ser
225                 230                 235                 240

Met Leu Thr Asp Pro Ser His Ile Thr Ala Glu Ala Gly Arg Arg
                245                 250                 255

Leu Ala Arg Gly Ser Pro Pro Ser Met Ala Ser Ser Ser Ala Ser Gln
            260                 265                 270

Leu Ser Ala Pro Ser Leu Lys Ala Thr Cys Thr Ala Asn His Asp Ser
        275                 280                 285

Pro Asp Ala Glu Leu Ile Glu Ala Asn Leu Leu Trp Arg Gln Glu Met
290                 295                 300

Gly Gly Asn Ile
305

<210> SEQ ID NO 100
<211> LENGTH: 283
<212> TYPE: PRT
<213> ORGANISM: Hepatitis C virus

<400> SEQUENCE: 100

Leu Ser Ser Leu Thr Val Thr Gln Leu Leu Arg Arg Leu His Gln Trp
1               5                   10                  15

Ile Ser Ser Glu Cys Thr Thr Pro Cys Ser Gly Ser Trp Leu Arg Asp
            20                  25                  30

Ile Trp Asp Trp Ile Cys Glu Val Leu Ser Asp Phe Lys Thr Trp Leu
        35                  40                  45

Lys Ala Lys Leu Met Pro Gln Leu Pro Gly Ile Pro Phe Val Ser Cys
    50                  55                  60

Gln Arg Gly Tyr Arg Gly Val Trp Arg Gly Asp Gly Ile Met His Thr
65                  70                  75                  80

Arg Cys His Cys Gly Ala Glu Ile Thr Gly His Val Lys Asn Gly Thr
                85                  90                  95

Met Arg Ile Val Gly Pro Arg Thr Cys Arg Asn Met Trp Ser Gly Thr
            100                 105                 110

Phe Pro Ile Asn Ala Tyr Thr Thr Gly Pro Cys Thr Pro Leu Pro Ala
        115                 120                 125

Pro Asn Tyr Lys Phe Ala Leu Trp Arg Val Ser Ala Glu Glu Tyr Val
    130                 135                 140

Glu Ile Arg Arg Val Gly Asp Phe His Tyr Val Ser Gly Met Thr Thr
145                 150                 155                 160

Asp Asn Leu Lys Cys Pro Cys Gln Ile Pro Ser Pro Glu Phe Phe Thr
                165                 170                 175

Glu Leu Asp Gly Val Arg Leu His Arg Phe Ala Pro Pro Cys Lys Pro
            180                 185                 190
```

```
Leu Leu Arg Glu Glu Val Ser Phe Arg Val Gly Leu His Glu Tyr Pro
        195                 200                 205

Val Gly Ser Gln Leu Pro Cys Glu Pro Glu Pro Asp Val Ala Val Leu
    210                 215                 220

Thr Ser Met Leu Thr Asp Pro Ser His Ile Thr Ala Glu Ala Ala Gly
225                 230                 235                 240

Arg Arg Leu Ala Arg Gly Ser Pro Pro Ser Met Ala Ser Ser Ser Ala
            245                 250                 255

Ser Gln Leu Ser Ala Pro Ser Leu Lys Ala Thr Cys Thr Ala Asn His
        260                 265                 270

Asp Ser Pro Asp Ala Glu Leu Ile Glu Ala Asn
        275                 280

<210> SEQ ID NO 101
<211> LENGTH: 249
<212> TYPE: PRT
<213> ORGANISM: Hepatitis C virus

<400> SEQUENCE: 101

Ser Leu Thr Val Thr Gln Leu Leu Arg Arg Leu His Gln Trp Ile Ser
1               5                   10                  15

Ser Glu Cys Thr Thr Pro Cys Ser Gly Ser Trp Leu Arg Asp Ile Trp
            20                  25                  30

Asp Trp Ile Cys Glu Val Leu Ser Asp Phe Lys Thr Trp Leu Lys Ala
        35                  40                  45

Lys Leu Met Pro Gln Leu Pro Gly Ile Pro Phe Val Ser Cys Gln Arg
    50                  55                  60

Gly Tyr Arg Gly Val Trp Arg Gly Asp Gly Ile Met His Thr Arg Cys
65                  70                  75                  80

His Cys Gly Ala Glu Ile Thr Gly His Val Lys Asn Gly Thr Met Arg
                85                  90                  95

Ile Val Gly Pro Arg Thr Cys Arg Asn Met Trp Ser Gly Thr Phe Pro
            100                 105                 110

Ile Asn Ala Tyr Thr Thr Gly Pro Cys Thr Pro Leu Pro Ala Pro Asn
        115                 120                 125

Tyr Lys Phe Ala Leu Trp Arg Val Ser Ala Glu Glu Tyr Val Glu Ile
    130                 135                 140

Arg Arg Val Gly Asp Phe His Tyr Val Ser Gly Met Thr Thr Asp Asn
145                 150                 155                 160

Leu Lys Cys Pro Cys Gln Ile Pro Ser Pro Glu Phe Phe Thr Glu Leu
                165                 170                 175

Asp Gly Val Arg Leu His Arg Phe Ala Pro Pro Cys Lys Pro Leu Leu
            180                 185                 190

Arg Glu Glu Val Ser Phe Arg Val Gly Leu His Glu Tyr Pro Val Gly
        195                 200                 205

Ser Gln Leu Pro Cys Glu Pro Glu Pro Asp Val Ala Val Leu Thr Ser
    210                 215                 220

Met Leu Thr Asp Pro Ser His Ile Thr Ala Glu Ala Ala Gly Arg Arg
225                 230                 235                 240

Leu Ala Arg Gly Ser Pro Pro Ser Met
                245

<210> SEQ ID NO 102
<211> LENGTH: 85
<212> TYPE: PRT
```

```
<213> ORGANISM: Hepatitis C virus

<400> SEQUENCE: 102

Thr Trp Leu Lys Ala Lys Leu Met Pro Gln Leu Pro Gly Ile Pro Phe
 1               5                  10                  15

Val Ser Cys Gln Arg Gly Tyr Arg Gly Val Trp Arg Gly Asp Gly Ile
                20                  25                  30

Met His Thr Arg Cys His Cys Gly Ala Glu Ile Thr Gly His Val Lys
            35                  40                  45

Asn Gly Thr Met Arg Ile Val Gly Pro Arg Thr Cys Arg Asn Met Trp
        50                  55                  60

Ser Gly Thr Phe Pro Ile Asn Ala Tyr Thr Thr Gly Pro Cys Thr Pro
65                  70                  75                  80

Leu Pro Ala Pro Asn
                85

<210> SEQ ID NO 103
<211> LENGTH: 94
<212> TYPE: PRT
<213> ORGANISM: Hepatitis C virus

<400> SEQUENCE: 103

Glu Ile Thr Gly His Val Lys Asn Gly Thr Met Arg Ile Val Gly Pro
 1               5                  10                  15

Arg Thr Cys Arg Asn Met Trp Ser Gly Thr Phe Pro Ile Asn Ala Tyr
                20                  25                  30

Thr Thr Gly Pro Cys Thr Pro Leu Pro Ala Pro Asn Tyr Lys Phe Ala
            35                  40                  45

Leu Trp Arg Val Ser Ala Glu Glu Tyr Val Glu Ile Arg Arg Val Gly
        50                  55                  60

Asp Phe His Tyr Val Ser Gly Met Thr Thr Asp Asn Leu Lys Cys Pro
65                  70                  75                  80

Cys Gln Ile Pro Ser Pro Glu Phe Phe Thr Glu Leu Asp Gly
                85                  90

<210> SEQ ID NO 104
<211> LENGTH: 75
<212> TYPE: PRT
<213> ORGANISM: Hepatitis C virus

<400> SEQUENCE: 104

Ile Glu Ala Asn Leu Leu Trp Arg Gln Glu Met Gly Gly Asn Ile Thr
 1               5                  10                  15

Arg Val Glu Ser Glu Asn Lys Val Val Ile Leu Asp Ser Phe Asp Pro
                20                  25                  30

Leu Val Ala Glu Glu Asp Glu Arg Glu Val Ser Val Pro Ala Glu Ile
            35                  40                  45

Leu Arg Lys Ser Arg Arg Phe Ala Arg Ala Leu Pro Val Trp Ala Arg
        50                  55                  60

Pro Asp Tyr Asn Pro Pro Leu Val Glu Thr Trp
65                  70                  75

<210> SEQ ID NO 105
<211> LENGTH: 90
<212> TYPE: PRT
<213> ORGANISM: Hepatitis C virus

<400> SEQUENCE: 105
```

```
His Gly Cys Pro Leu Pro Pro Arg Ser Pro Pro Val Pro Pro Pro
 1               5                  10                 15

Arg Lys Lys Arg Thr Val Val Leu Thr Glu Ser Thr Leu Ser Thr Ala
             20                  25                  30

Leu Ala Glu Leu Ala Thr Lys Ser Phe Gly Ser Ser Thr Ser Gly
         35                  40                  45

Ile Thr Gly Asp Asn Thr Thr Thr Ser Ser Glu Pro Ala Pro Ser Gly
 50                  55                  60

Cys Pro Pro Asp Ser Asp Val Glu Ser Tyr Ser Ser Met Pro Pro Leu
 65              70                  75                      80

Glu Gly Glu Pro Gly Asp Pro Asp Leu Ser
                 85                  90
```

<210> SEQ ID NO 106
<211> LENGTH: 137
<212> TYPE: PRT
<213> ORGANISM: Hepatitis C virus

<400> SEQUENCE: 106

```
Ser Trp Thr Gly Ala Leu Val Thr Pro Cys Ala Ala Glu Glu Gln Lys
 1               5                  10                  15

Leu Pro Ile Asn Ala Leu Ser Asn Ser Leu Leu Arg His His Asn Leu
             20                  25                  30

Val Tyr Ser Thr Thr Ser Arg Ser Ala Cys Gln Arg Gln Lys Lys Val
         35                  40                  45

Thr Phe Asp Arg Leu Gln Val Leu Asp Ser His Tyr Gln Asp Val Leu
 50                  55                  60

Lys Glu Val Lys Ala Ala Ala Ser Lys Val Lys Ala Asn Leu Leu Ser
 65                  70                  75                  80

Val Glu Glu Ala Cys Ser Leu Thr Pro Pro His Ser Ala Lys Ser Lys
                 85                  90                  95

Phe Gly Tyr Gly Ala Lys Asp Val Arg Cys His Ala Arg Lys Ala Val
             100                 105                 110

Ala His Ile Asn Ser Val Trp Lys Asp Leu Leu Glu Asp Ser Val Thr
         115                 120                 125

Pro Ile Asp Thr Thr Ile Met Ala Lys
     130                 135
```

<210> SEQ ID NO 107
<211> LENGTH: 300
<212> TYPE: PRT
<213> ORGANISM: Hepatitis C virus

<400> SEQUENCE: 107

```
Ala Asn Leu Leu Ser Val Glu Glu Ala Cys Ser Leu Thr Pro Pro His
 1               5                  10                  15

Ser Ala Lys Ser Lys Phe Gly Tyr Gly Ala Lys Asp Val Arg Cys His
             20                  25                  30

Ala Arg Lys Ala Val Ala His Ile Asn Ser Val Trp Lys Asp Leu Leu
         35                  40                  45

Glu Asp Ser Val Thr Pro Ile Asp Thr Thr Ile Met Ala Lys Asn Glu
 50                  55                  60

Val Phe Cys Val Gln Pro Glu Lys Gly Gly Arg Lys Pro Ala Arg Leu
 65                  70                  75                  80

Ile Val Phe Pro Asp Leu Gly Val Arg Val Cys Glu Lys Met Ala Leu
                 85                  90                  95
```

```
Tyr Asp Val Val Ser Lys Leu Pro Leu Ala Val Met Gly Ser Ser Tyr
            100                 105                 110
Gly Phe Gln Tyr Ser Pro Gly Gln Arg Val Glu Phe Leu Val Gln Ala
            115                 120                 125
Trp Lys Ser Lys Thr Pro Met Gly Phe Ser Tyr Asp Thr Arg Cys
130                 135                 140
Phe Asp Ser Thr Val Thr Glu Ser Asp Ile Arg Thr Glu Ala Ile
145                 150                 155                 160
Tyr Gln Cys Cys Asp Leu Asp Pro Gln Ala Arg Val Ala Ile Lys Ser
                165                 170                 175
Leu Thr Glu Arg Leu Tyr Val Gly Gly Pro Leu Thr Asn Ser Arg Gly
            180                 185                 190
Glu Asn Cys Gly Tyr Arg Arg Cys Arg Ala Ser Gly Val Leu Thr Thr
            195                 200                 205
Ser Cys Gly Asn Thr Leu Thr Cys Tyr Ile Lys Ala Arg Ala Ala Cys
        210                 215                 220
Arg Ala Ala Gly Leu Gln Asp Cys Thr Met Leu Val Cys Gly Asp Asp
225                 230                 235                 240
Leu Val Val Ile Cys Glu Ser Ala Gly Val Gln Glu Asp Ala Ala Ser
                245                 250                 255
Leu Arg Ala Phe Thr Glu Ala Met Thr Arg Tyr Ser Ala Pro Pro Gly
            260                 265                 270
Asp Pro Pro Gln Pro Glu Tyr Asp Leu Glu Leu Ile Thr Ser Cys Ser
            275                 280                 285
Ser Asn Val Ser Val Ala His Asp Gly Ala Gly Lys
        290                 295                 300

<210> SEQ ID NO 108
<211> LENGTH: 199
<212> TYPE: PRT
<213> ORGANISM: Hepatitis C virus

<400> SEQUENCE: 108

Glu Glu Ala Cys Ser Leu Thr Pro Pro His Ser Ala Lys Ser Lys Phe
1               5                   10                  15
Gly Tyr Gly Ala Lys Asp Val Arg Cys His Ala Arg Lys Ala Val Ala
            20                  25                  30
His Ile Asn Ser Val Trp Lys Asp Leu Leu Glu Asp Ser Val Thr Pro
        35                  40                  45
Ile Asp Thr Thr Ile Met Ala Lys Asn Glu Val Phe Cys Val Gln Pro
    50                  55                  60
Glu Lys Gly Gly Arg Lys Pro Ala Arg Leu Ile Val Phe Pro Asp Leu
65                  70                  75                  80
Gly Val Arg Val Cys Glu Lys Met Ala Leu Tyr Asp Val Val Ser Lys
                85                  90                  95
Leu Pro Leu Ala Val Met Gly Ser Ser Tyr Gly Phe Gln Tyr Ser Pro
            100                 105                 110
Gly Gln Arg Val Glu Phe Leu Val Gln Ala Trp Lys Ser Lys Lys Thr
            115                 120                 125
Pro Met Gly Phe Ser Tyr Asp Thr Arg Cys Phe Asp Ser Thr Val Thr
        130                 135                 140
Glu Ser Asp Ile Arg Thr Glu Ala Ile Tyr Gln Cys Cys Asp Leu
145                 150                 155                 160
Asp Pro Gln Ala Arg Val Ala Ile Lys Ser Leu Thr Glu Arg Leu Tyr
                165                 170                 175
```

```
Val Gly Gly Pro Leu Thr Asn Ser Arg Gly Glu Asn Cys Gly Tyr Arg
            180                 185                 190

Arg Cys Arg Ala Ser Gly Val
        195

<210> SEQ ID NO 109
<211> LENGTH: 260
<212> TYPE: PRT
<213> ORGANISM: Hepatitis C virus

<400> SEQUENCE: 109

Leu Leu Glu Asp Ser Val Thr Pro Ile Asp Thr Thr Ile Met Ala Lys
  1               5                  10                  15

Asn Glu Val Phe Cys Val Gln Pro Glu Lys Gly Gly Arg Lys Pro Ala
             20                  25                  30

Arg Leu Ile Val Phe Pro Asp Leu Gly Val Arg Val Cys Glu Lys Met
         35                  40                  45

Ala Leu Tyr Asp Val Val Ser Lys Leu Pro Leu Ala Val Met Gly Ser
     50                  55                  60

Ser Tyr Gly Phe Gln Tyr Ser Pro Gly Gln Arg Val Glu Phe Leu Val
 65                  70                  75                  80

Gln Ala Trp Lys Ser Lys Lys Thr Pro Met Gly Phe Ser Tyr Asp Thr
                 85                  90                  95

Arg Cys Phe Asp Ser Thr Val Thr Glu Ser Asp Ile Arg Thr Glu Glu
            100                 105                 110

Ala Ile Tyr Gln Cys Cys Asp Leu Asp Pro Gln Ala Arg Val Ala Ile
        115                 120                 125

Lys Ser Leu Thr Glu Arg Leu Tyr Val Gly Gly Pro Leu Thr Asn Ser
    130                 135                 140

Arg Gly Glu Asn Cys Gly Tyr Arg Arg Cys Arg Ala Ser Gly Val Leu
145                 150                 155                 160

Thr Thr Ser Cys Gly Asn Thr Leu Thr Cys Tyr Ile Lys Ala Arg Ala
                165                 170                 175

Ala Cys Arg Ala Ala Gly Leu Gln Asp Cys Thr Met Leu Val Cys Gly
            180                 185                 190

Asp Asp Leu Val Val Ile Cys Glu Ser Ala Gly Val Gln Glu Asp Ala
        195                 200                 205

Ala Ser Leu Arg Ala Phe Thr Glu Ala Met Thr Arg Tyr Ser Ala Pro
    210                 215                 220

Pro Gly Asp Pro Pro Gln Pro Glu Tyr Asp Leu Glu Leu Ile Thr Ser
225                 230                 235                 240

Cys Ser Ser Asn Val Ser Val Ala His Asp Gly Ala Gly Lys Arg Val
                245                 250                 255

Tyr Tyr Leu Thr
            260

<210> SEQ ID NO 110
<211> LENGTH: 127
<212> TYPE: PRT
<213> ORGANISM: Hepatitis C virus

<400> SEQUENCE: 110

Val Ile Cys Glu Ser Ala Gly Val Gln Glu Asp Ala Ala Ser Leu Arg
  1               5                  10                  15

Ala Phe Thr Glu Ala Met Thr Arg Tyr Ser Ala Pro Pro Gly Asp Pro
             20                  25                  30
```

```
Pro Gln Pro Glu Tyr Asp Leu Glu Leu Ile Thr Ser Cys Ser Ser Asn
        35                  40                  45

Val Ser Val Ala His Asp Gly Ala Gly Lys Arg Val Tyr Tyr Leu Thr
 50                  55                  60

Arg Asp Pro Thr Thr Pro Leu Ala Arg Ala Ala Trp Glu Thr Ala Arg
 65                  70                  75                  80

His Thr Pro Val Asn Ser Trp Leu Gly Asn Ile Ile Met Phe Ala Pro
                 85                  90                  95

Thr Leu Trp Ala Arg Met Ile Leu Met Thr His Phe Phe Ser Val Leu
            100                 105                 110

Ile Ala Arg Asp Gln Leu Glu Gln Ala Leu Asn Cys Glu Ile Tyr
            115                 120                 125

<210> SEQ ID NO 111
<211> LENGTH: 89
<212> TYPE: PRT
<213> ORGANISM: Hepatitis C virus

<400> SEQUENCE: 111

Val Ser Val Ala His Asp Gly Ala Gly Lys Arg Val Tyr Tyr Leu Thr
 1               5                  10                  15

Arg Asp Pro Thr Thr Pro Leu Ala Arg Ala Ala Trp Glu Thr Ala Arg
            20                  25                  30

His Thr Pro Val Asn Ser Trp Leu Gly Asn Ile Ile Met Phe Ala Pro
            35                  40                  45

Thr Leu Trp Ala Arg Met Ile Leu Met Thr His Phe Phe Ser Val Leu
     50                  55                  60

Ile Ala Arg Asp Gln Leu Glu Gln Ala Leu Asn Cys Glu Ile Tyr Gly
 65                  70                  75                  80

Ala Cys Tyr Ser Ile Glu Pro Leu Asp
                 85

<210> SEQ ID NO 112
<211> LENGTH: 73
<212> TYPE: PRT
<213> ORGANISM: Hepatitis C virus

<400> SEQUENCE: 112

Leu His Gly Leu Ser Ala Phe Ser Leu His Ser Tyr Ser Pro Gly Glu
 1               5                  10                  15

Ile Asn Arg Val Ala Ala Cys Leu Arg Lys Leu Gly Val Pro Pro Leu
            20                  25                  30

Arg Ala Trp Arg His Arg Ala Arg Ser Val Arg Ala Arg Leu Leu Ser
            35                  40                  45

Arg Gly Gly Arg Ala Ala Ile Cys Gly Lys Tyr Leu Phe Asn Trp Ala
     50                  55                  60

Val Arg Thr Lys Leu Lys Leu Thr Pro
 65                  70

<210> SEQ ID NO 113
<211> LENGTH: 63
<212> TYPE: PRT
<213> ORGANISM: Hepatitis C virus

<400> SEQUENCE: 113

Ser Pro Gly Glu Ile Asn Arg Val Ala Ala Cys Leu Arg Lys Leu Gly
 1               5                  10                  15
```

```
Val Pro Pro Leu Arg Ala Trp Arg His Arg Ala Arg Ser Val Arg Ala
            20                  25                  30

Arg Leu Leu Ser Arg Gly Gly Arg Ala Ala Ile Cys Gly Lys Tyr Leu
        35                  40                  45

Phe Asn Trp Ala Val Arg Thr Lys Leu Lys Leu Thr Pro Ile Ala
    50                  55                  60

<210> SEQ ID NO 114
<211> LENGTH: 310
<212> TYPE: DNA
<213> ORGANISM: Hepatitis C virus

<400> SEQUENCE: 114
tgcttgcgag tgccccggga ggtctcgtag accgtgcacc atgagcacga atcctaaacc      60
tcaaagaaaa accaaacgta acaccaaccg tcgcccacag gacgtcaagt tcccgggtgg     120
cggtcagatc gttggtggag tttacttgtt gccgcgcagg ggccctagat tgggtgtgcg     180
cgcgacgagg aagacttccg agcggtcgca acctcgaggt agacgtcagc ctatccccaa    240
ggcacgtcgg cccgagggca ggacctgggc tcagcccggg taccttggc ccctctatgg     300 caatgagggt                                                            310

<210> SEQ ID NO 115
<211> LENGTH: 339
<212> TYPE: DNA
<213> ORGANISM: Hepatitis C virus

<400> SEQUENCE: 115
atgagcacga atcctaaacc tcaaagaaaa accaaacgta acaccaaccg tcgcccacag      60
gacgtcaagt tcccgggtgg cggtcagatc gttggtggag tttacttgtt gccgcgcagg    120
ggccctagat tgggtgtgcg cgcgacgagg aagacttccg agcggtcgca acctcgaggt    180
agacgtcagc ctatccccaa ggcacgtcgg cccgagggca ggacctgggc tcagcccggg    240 taccttggc ccctctatgg caatgagggt tgcgggtggg cgggatggct cctgtctccc     300
cgtggctctc ggcctagctg gggccccaca gacccccgg                            339

<210> SEQ ID NO 116
<211> LENGTH: 345
<212> TYPE: DNA
<213> ORGANISM: Hepatitis C virus

<400> SEQUENCE: 116
tgccatcctg cacactccgg ggtgtgtccc ttgcgttcgc gagggtaacg cctcgaggtg      60
ttgggtggcg gtgaccccca cggtggccac cagggacggc aaactcccca caacgcagct    120
tcgacgtcat atcgatctgc ttgtcgggag cgccaccctc tgctcggccc tctacgtggg    180
ggacctgtgc gggtctgtct ttcttgttgg tcaactgttt accttctctc ccaggcgcca    240
ctggacgacg caagactgca attgttctat ctatcccggc catataacgg gtcatcgcat    300
ggcatgggat atgatgatga actggtcccc tacggcagcg ttggt                    345

<210> SEQ ID NO 117
<211> LENGTH: 276
<212> TYPE: DNA
<213> ORGANISM: Hepatitis C virus

<400> SEQUENCE: 117
cggcgtcgac gcggaaaccc acgtcaccgg gggaaatgcc ggccgcacca cggctgggct      60
```

-continued

| | |
|---|---|
| tgttggtctc cttacaccag gcgccaagca gaacatccaa ctgatcaaca ccaacggcag | 120 |
| ttggcacatc aatagcacgg ccttgaattg caatgaaagc cttaacaccg gctggttagc | 180 |
| agggctcttc tatcaacaca aattcaactc ttcaggctgt cctgagaggt tggccagctg | 240 |
| ccgacgcctt accgattttg cccagggctg gggtcc | 276 |

<210> SEQ ID NO 118
<211> LENGTH: 531
<212> TYPE: DNA
<213> ORGANISM: Hepatitis C virus

<400> SEQUENCE: 118

| | |
|---|---|
| ctggggtcct atcagttatg ccaacggaag cggcctcgac gaacgcccct actgctggca | 60 |
| ctaccctcca agaccttgtg gcattgtgcc cgcaaagagc gtgtgtggcc cggtatattg | 120 |
| cttcactccc agcccgtgg tggtgggaac gaccgacagg tcgggcgcgc ctacctacag | 180 |
| ctggggtgca aatgatacgg atgtcttcgt ccttaacaac accaggccac cgctgggcaa | 240 |
| ttggttcggt tgtacctgga tgaactcaac tggattcacc aaagtgtgcg gagcgccccc | 300 |
| ttgtgtcatc ggaggggtgg gcaacaacac cttgctctgc cccactgatt gcttccgcaa | 360 |
| acatccggaa gccacatact ctcggtgcgg ctccggtccc tggattacac ccaggtgcat | 420 |
| ggtcgactac ccgtataggc tttggcacta tccttgtacc atcaattaca ccatattcaa | 480 |
| agtcaggatg tacgtgggag gggtcgagca caggctggaa gcggcctgca a | 531 |

<210> SEQ ID NO 119
<211> LENGTH: 289
<212> TYPE: DNA
<213> ORGANISM: Hepatitis C virus

<400> SEQUENCE: 119

| | |
|---|---|
| ctggcactac cctccaagac cttgtggcat tgtgcccgca aagagcgtgt gtggcccggt | 60 |
| atattgcttc actcccagcc cgtggtggt gggaacgacc gacaggtcgg gcgcgcctac | 120 |
| ctacagctgg ggtgcaaatg atacggatgt cttcgtcctt aacaacacca ggccaccgct | 180 |
| gggcaattgg ttcggttgta cctggatgaa ctcaactgga ttcaccaaag tgtgcggagc | 240 |
| gccccttgt gtcatcggag gggtgggcaa caacaccttg ctctgcccc | 289 |

<210> SEQ ID NO 120
<211> LENGTH: 836
<212> TYPE: DNA
<213> ORGANISM: Hepatitis C virus

<400> SEQUENCE: 120

| | |
|---|---|
| gccgcgtgcg gtgacatcat caacggcttg cccgtctctg cccgtagggg ccaggagata | 60 |
| ctgcttgggc cagccgacgg aatggtctcc aaggggtgga ggttgctggc gcccatcacg | 120 |
| gcgtacgccc agcagacgag aggcctccta gggtgtataa tcaccagcct gactggccgg | 180 |
| gacaaaaacc aagtggaggg tgaggtccag atcgtgtcaa ctgctaccca aaccttcctg | 240 |
| gcaacgtgca tcaatggggt atgctggact gtctaccacg gggccggaac gaggaccatc | 300 |
| gcatcaccca aggtcctgt catccagatg tataccaatg tggaccaaga ccttgtgggc | 360 |
| tggcccgctc ctcaaggttc ccgctcattg acaccctgta cctgcggctc ctcggacctt | 420 |
| tacctggtca cgaggcacgc cgatgtcatt cccgtgcgcc ggcgaggtga tagcagggt | 480 |
| agcctgcttt cgccccggcc catttcctac ttgaaaggct cctcgggggg tccgctgttg | 540 |
| tgccccgcgg gacacgccgt gggcctattc agggccgcgg tgtgcacccg tggagtggct | 600 |

```
aaagcggtgg actttatccc tgtggagaac ctagggacaa ccatgagatc cccggtgttc    660
acggacaact cctctccacc agcagtgccc cagagcttcc aggtggccca cctgcatgct    720
cccaccggca gcggtaagag caccaaggtc ccggctgcgt acgcagccca gggctacaag    780
gtgttggtgc tcaaccccctc tgttgctgca acgctgggct ttggtgctta catgtc      836

<210> SEQ ID NO 121
<211> LENGTH: 475
<212> TYPE: DNA
<213> ORGANISM: Hepatitis C virus

<400> SEQUENCE: 121
gcgccggcga ggtgatagca ggggtagcct gctttcgccc cggcccattt cctacttgaa    60
aggctcctcg gggggtccgc tgttgtgccc cgcgggacac gccgtgggcc tattcagggc   120
cgcggtgtgc acccgtggag tggctaaagc ggtggacttt atccctgtgg agaacctagg   180
gacaaccatg agatccccgg tgttcacgga caactcctct ccaccagcag tgccccagag   240
cttccaggtg gcccacctgc atgctcccac cggcagcgt aagagcacca aggtcccggc   300
tgcgtacgca gcccagggct acaaggtgtt ggtgctcaac ccctctgttg ctgcaacgct   360
gggctttggt gcttacatgt ccaaggccca tgggttgat cctaatatca ggaccggggt   420
gagaacaatt accactggca gccccatcac gtactccacc tacggcaagt tcctt        475

<210> SEQ ID NO 122
<211> LENGTH: 790
<212> TYPE: DNA
<213> ORGANISM: Hepatitis C virus

<400> SEQUENCE: 122
tgatagcagg ggtagcctgc tttcgccccg gcccatttcc tacttgaaag gctcctcggg    60
gggtccgctg ttgtgcccg cgggacacgc cgtgggccta ttcagggccg cggtgtgcac   120
ccgtggagtg gctaaagcgg tggactttat ccctgtggag aacctaggga caaccatgag   180
atccccggtg ttcacggaca actcctctcc accagcagtg ccccagagct tccaggtggc   240
ccacctgcat gctcccaccg gcagcggtaa gagcaccaag gtcccggctg cgtacgcagc   300
ccagggctac aaggtgttgg tgctcaaccc ctctgttgct gcaacgctgg gctttggtgc   360
ttacatgtcc aaggcccatg ggttgatcc taatatcagg accggggtga gaacaattac   420
cactggcagc cccatcacgt actccaccta cggcaagttc cttgccgacg gcgggtgctc   480
aggaggtgct tatgacataa taatttgtga cgagtgccac tccacggatg ccacatccat   540
cttgggcatc ggcactgtcc ttgaccaagc agagactgcg gggcgagac tggttgtgct   600 cgccactgct accctccgg gctccgtcac tgtgtcccat cctaacatcg aggaggttgc   660
tctgtccacc accggagaga tccccttta cggcaaggct atcccctcg aggtgatcaa   720 ggggggaaga catctcatct ctgccactc aaagaagaag tgcgacgagc tcgccgcgaa   780
gctggtcgca                                                          790

<210> SEQ ID NO 123
<211> LENGTH: 583
<212> TYPE: DNA
<213> ORGANISM: Hepatitis C virus

<400> SEQUENCE: 123
ggacaactcc tctccaccag cagtgcccca gagcttccag gtggcccacc tgcatgctcc    60
```

```
caccggcagc ggtaagagca ccaaggtccc ggctgcgtac gcagcccagg gctacaaggt      120
gttggtgctc aaccctctg ttgctgcaac gctgggcttt ggtgcttaca tgtccaaggc       180
ccatggggtt gatcctaata tcaggaccgg ggtgagaaca attaccactg cagccccat       240 cacgtactcc acctacggca agttccttgc cgacggcggg tgctcaggag gtgcttatga      300
cataataatt tgtgacgagt gccactccac ggatgccaca tccatcttgg gcatcggcac      360
tgtccttgac caagcagaga ctgcgggggc gagactggtt gtgctcgcca ctgctacccc      420
tccgggctcc gtcactgtgt cccatcctaa catcgaggag gttgctctgt ccaccaccgg      480
agagatcccc ttttacggca aggctatccc cctcgaggtg atcaaggggg aagacatct       540 catcttctgc cactcaaaga gaagtgcga cgagctcgcc gcg                         583

<210> SEQ ID NO 124
<211> LENGTH: 617
<212> TYPE: DNA
<213> ORGANISM: Hepatitis C virus

<400> SEQUENCE: 124
ccttgccgac ggcgggtgct caggaggtgc ttatgacata ataatttgtg acgagtgcca      60
ctccacggat gccacatcca tcttgggcat cggcactgtc cttgaccaag cagagactgc     120
gggggcgaga ctggttgtgc tcgccactgc taccccctccg ggctccgtca ctgtgtccca    180
tcctaacatc gaggaggttg ctctgtccac caccggagag atccccttt acggcaaggc      240 tatccccctc gaggtgatca agggggaag acatctcatc ttctgccact caaagaagaa      300
gtgcgacgag ctcgccgcga agctggtcgc attgggcatc aatgccgtgg cctactaccg    360
cggtcttgac gtgtctgtca tcccgaccag cggcgatgtt gtcgtcgtgt cgaccgatgc     420
tctcatgact ggctttaccg cgcgacttcga ctctgtgata gactgcaaca cgtgtgtcac     480
tcagacagtc gatttcagcc ttgaccctac ctttaccatt gagacaacca cgctccccca     540
ggatgctgtc tccaggactc aacgccgggg caggactggc aggggaagc caggcatcta     600 tagatttgtg gcaccgg                                                    617

<210> SEQ ID NO 125
<211> LENGTH: 559
<212> TYPE: DNA
<213> ORGANISM: Hepatitis C virus

<400> SEQUENCE: 125
ctccacggat gccacatcca tcttgggcat cggcactgtc cttgaccaag cagagactgc      60
gggggcgaga ctggttgtgc tcgccactgc taccccctccg ggctccgtca ctgtgtccca   120
tcctaacatc gaggaggttg ctctgtccac caccggagag atccccttt acggcaaggc      180 tatccccctc gaggtgatca agggggaag acatctcatc ttctgccact caaagaagaa      240
gtgcgacgag ctcgccgcga agctggtcgc attgggcatc aatgccgtgg cctactaccg    300
cggtcttgac gtgtctgtca tcccgaccag cggcgatgtt gtcgtcgtgt cgaccgatgc     360
tctcatgact ggctttaccg cgcgacttcga ctctgtgata gactgcaaca cgtgtgtcac     420
tcagacagtc gatttcagcc ttgaccctac ctttaccatt gagacaacca cgctccccca     480
ggatgctgtc tccaggactc aacgccgggg caggactggc aggggaagc caggcatcta     540 tagatttgtg gcaccgggg                                                  559

<210> SEQ ID NO 126
<211> LENGTH: 475
```

-continued

```
<212> TYPE: DNA
<213> ORGANISM: Hepatitis C virus

<400> SEQUENCE: 126
tgtgatagac tgcaacacgt gtgtcactca gacagtcgat ttcagccttg accctacctt      60
taccattgag acaaccacgc tcccccagga tgctgtctcc aggactcaac gccggggcag     120
gactggcagg gggaagccag gcatctatag atttgtggca ccgggggagc gcccctccgg     180
catgttcgac tcgtccgtcc tctgtgagtg ctatgacgcg ggctgtgctt ggtatgagct     240
cacgcccgcc gagactacag ttaggctacg agcgtacatg aacacccggg gcttcccgt      300 gtgccaggac catcttgaat tttgggaggg cgtctttacg ggcctcactc atatagatgc     360
ccacttttta tcccagacaa agcagagtgg ggagaacttt ccttacctgg tagcgtacca     420
agccaccgtg tgcgctaggg ctcaagcccc tcccccatcg tgggaccaga tgtgg         475

<210> SEQ ID NO 127
<211> LENGTH: 390
<212> TYPE: DNA
<213> ORGANISM: Hepatitis C virus

<400> SEQUENCE: 127
tagatttgtg gcaccggggg agcgcccctc cggcatgttc gactcgtccg tcctctgtga      60
gtgctatgac gcgggctgtg cttggtatga gctcacgccc gccgagacta cagttaggct     120
acgagcgtac atgaacaccc cggggcttcc cgtgtgccag gaccatcttg aattttggga     180
gggcgtcttt acgggcctca ctcatataga tgcccacttt ttatcccaga caaagcagag     240
tggggagaac tttccttacc tggtagcgta ccaagccacc gtgtgcgcta gggctcaagc     300
ccctccccca tcgtgggacc agatgtggaa gtgtttgatc cgccttaaac ccaccctcca     360
tgggccaaca ccctgctat acagactggg                                        390

<210> SEQ ID NO 128
<211> LENGTH: 155
<212> TYPE: DNA
<213> ORGANISM: Hepatitis C virus

<400> SEQUENCE: 128
acgagcacct gggtgctcgt tggcggcgtc ctggctgctc tggccgcgta ttgcctgtca      60
acaggctgcg tggtcatagt gggcaggatc gtcttgtccg ggaagccggc aattatacct     120
gacagggagg ttctctacca ggagttcgat gagat                                155

<210> SEQ ID NO 129
<211> LENGTH: 56
<212> TYPE: DNA
<213> ORGANISM: Hepatitis C virus

<400> SEQUENCE: 129
ggctgctctg gccgcgtatt gcctgtcaac aggctgcgtg gtcatagtgg gcagga          56

<210> SEQ ID NO 130
<211> LENGTH: 625
<212> TYPE: DNA
<213> ORGANISM: Hepatitis C virus

<400> SEQUENCE: 130
ttttacagct gccgtcacca gcccactaac cactggccaa accctcctct tcaacatatt      60
gggggggtgg gtggctgccc agctcgccgc ccccggtgcc gctactgcct tgtgggtgc      120
```

```
tggcctagct ggcgccgcca tcggcagcgt tggactgggg aaggtcctcg tggacattct    180
tgcagggtat ggcgcgggcg tggcgggagc tcttgtagca ttcaagatca tgagcggtga    240
ggtcccctcc acggaggacc tggtcaatct gctgcccgcc atcctctcgc ctggagccct    300
tgtagtcggt gtggtctgcg cagcaatact gcgccggcac gttggcccgg gcgaggggggc   360 agtgcaatgg atgaaccggc taatagcctt cgcctcccgg gggaaccatg tttcccccac    420
gcactacgtg ccggagagcg atgcagccgc ccgcgtcact gccatactca gcagcctcac    480
tgtaacccag ctcctgaggc gactgcatca gtggataagc tcggagtgta ccactccatg    540
ctccggttcc tggctaaggg acatctggga ctggatatgc gaggtgctga gcgactttaa    600
gacctggctg aaagccaagc tcatg                                          625
```

<210> SEQ ID NO 131
<211> LENGTH: 623
<212> TYPE: DNA
<213> ORGANISM: Hepatitis C virus

<400> SEQUENCE: 131

```
tactgccttt gtgggtgctg gcctagctgg cgccgccatc ggcagcgttg gactggggaa     60
ggtcctcgtg gacattcttg cagggtatgg cgcgggcgtg gcgggagctc ttgtagcatt    120
caagatcatg agcggtgagg tcccctccac ggaggacctg tcaatctgc tgcccgccat     180 cctctcgcct ggagcccttg tagtcggtgt ggtctgcgca gcaatactgc gccggcacgt    240
tggcccgggc gagggggcag tgcaatggat gaaccggcta atagccttcg cctcccgggg    300
gaaccatgtt tcccccacgc actacgtgcc ggagagcgat gcagccgccc gcgtcactgc    360
catactcagc agcctcactg taacccagct cctgaggcga ctgcatcagt ggataagctc    420
ggagtgtacc actccatgct ccggttcctg gctaagggac atctgggact ggatatgcga    480
ggtgctgagc gactttaaga cctggctgaa agccaagctc atgccacaac tgcctgggat    540
tccctttgtg tcctgccagc gcgggtatag ggggtctgg cgaggagacg gcattatgca     600
cactcgctgc cactgtggag ctg                                            623
```

<210> SEQ ID NO 132
<211> LENGTH: 678
<212> TYPE: DNA
<213> ORGANISM: Hepatitis C virus

<400> SEQUENCE: 132

```
cctcgtggac attcttgcag ggtatggcgc gggcgtggcg ggagctcttg tagcattcaa     60
gatcatgagc ggtgaggtcc cctccacgga ggacctggtc aatctgctgc ccgccatcct    120
ctcgcctgga gcccttgtag tcggtgtggt ctgcgcagca atactgcgcc ggcacgttgg    180
cccgggcgag ggggcagtgc aatggatgaa ccggctaata gccttcgcct cccgggggaa    240
ccatgtttcc cccacgcact acgtgccgga gagcgatgca gccgcccgcg tcactgccat    300
actcagcagc tcactgtaa cccagctcct gaggcgactg catcagtgga taagctcgga     360
gtgtaccact ccatgctccg gttcctggct aagggacatc tgggactgga tatgcgaggt    420
gctgagcgac tttaagacct ggctgaaagc caagctcatg ccacaactgc ctgggattcc    480
ctttgtgtcc tgccagcgcg gtataggg gtctggcga ggacgca ttatgcacac           540 tcgctgccac tgtggagctg agatcactgg acatgtcaaa aacgggacga tgaggatcgt    600
cggtcctagg acctgcagga acatgtggag tgggacgttc ccattaacg cctacaccac     660 gggcccctgt actcccct                                                  678
```

<210> SEQ ID NO 133
<211> LENGTH: 436
<212> TYPE: DNA
<213> ORGANISM: Hepatitis C virus

<400> SEQUENCE: 133

| | | | | | |
|---|---|---|---|---|---|
| tgcagggtat | ggcgcgggcg | tggcgggagc | tcttgtagca | ttcaagatca | tgagcggtga | 60 |
| ggtcccctcc | acggaggacc | tggtcaatct | gctgcccgcc | atcctctcgc | ctggagccct | 120 |
| tgtagtcggt | gtggtctgcg | cagcaatact | gcgccggcac | gttggcccgg | gcagggggc | 180 |
| agtgcaatgg | atgaaccggc | taatagcctt | cgcctcccgg | gggaaccatg | tttcccccac | 240 |
| gcactacgtg | ccggagagcg | atgcagccgc | ccgcgtcact | gccatactca | gcagcctcac | 300 |
| tgtaacccag | ctcctgaggc | gactgcatca | gtggataagc | tcggagtgta | ccactccatg | 360 |
| ctccggttcc | tggctaaggg | acatctggga | ctggatatgc | gaggtgctga | gcgactttaa | 420 |
| gacctggctg | aaagcc | | | | | 436 |

<210> SEQ ID NO 134
<211> LENGTH: 164
<212> TYPE: DNA
<213> ORGANISM: Hepatitis C virus

<400> SEQUENCE: 134

| | | | | | |
|---|---|---|---|---|---|
| agcccttgta | gtcggtgtgg | tctgcgcagc | aatactgcgc | cggcacgttg | cccgggcga | 60 |
| ggggcagtg | caatggatga | accggctaat | agccttcgcc | tccgggggga | accatgtttc | 120 |
| ccccacgcac | tacgtgccgg | agagcgatgc | agccgcccgc | gtca | | 164 |

<210> SEQ ID NO 135
<211> LENGTH: 496
<212> TYPE: DNA
<213> ORGANISM: Hepatitis C virus

<400> SEQUENCE: 135

| | | | | | |
|---|---|---|---|---|---|
| cgcctcccgg | gggaaccatg | tttcccccac | gcactacgtg | ccggagagcg | atgcagccgc | 60 |
| ccgcgtcact | gccatactca | gcagcctcac | tgtaacccag | ctcctgaggc | gactgcatca | 120 |
| gtggataagc | tcggagtgta | ccactccatg | ctccggttcc | tggctaaggg | acatctggga | 180 |
| ctggatatgc | gaggtgctga | gcgactttaa | gacctggctg | aaagccaagc | tcatgccaca | 240 |
| actgcctggg | attcccttg | tgtcctgcca | gcgcgggtat | agggggtct | ggcgaggaga | 300 |
| cggcattatg | cacactcgct | gccactgtgg | agctgagatc | actggacatg | tcaaaaacgg | 360 |
| gacgatgagg | atcgtcggtc | ctaggacctg | caggaacatg | tggagtggga | cgttccccat | 420 |
| taacgcctac | accacgggcc | cctgtactcc | ccttcctgcg | ccgaactata | agttcgcgct | 480 |
| gtggagggtg | tctgca | | | | | 496 |

<210> SEQ ID NO 136
<211> LENGTH: 926
<212> TYPE: DNA
<213> ORGANISM: Hepatitis C virus

<400> SEQUENCE: 136

| | | | | | |
|---|---|---|---|---|---|
| tacgtgccgg | agagcgatgc | agccgcccgc | gtcactgcca | tactcagcag | cctcactgta | 60 |
| acccagctcc | tgaggcgact | gcatcagtgg | ataagctcgg | agtgtaccac | tccatgctcc | 120 |
| ggttcctggc | taagggacat | ctgggactgg | atatgcgagg | tgctgagcga | ctttaagacc | 180 |

| | |
|---|---:|
| tggctgaaag ccaagctcat gccacaactg cctgggattc cctttgtgtc ctgccagcgc | 240 |
| gggtataggg gggtctggcg aggagacggc attatgcaca ctcgctgcca ctgtggagct | 300 |
| gagatcactg gacatgtcaa aacgggacg atgaggatcg tcggtcctag gacctgcagg | 360 |
| aacatgtgga gtgggacgtt ccccattaac gcctacacca cgggcccctg tactcccctt | 420 |
| cctgcgccga actataagtt cgcgctgtgg agggtgtctg cagaggaata cgtggagata | 480 |
| aggcgggtgg gggacttcca ctacgtatcg ggtatgacta ctgacaatct taaatgcccg | 540 |
| tgccagatcc catcgcccga atttttcaca gaattggacg gggtgcgcct acacaggttt | 600 |
| gcgcccccctt gcaagcccctt gctgcgggag gaggtatcat tcagagtagg actccacgag | 660 |
| tacccggtgg ggtcgcaatt accttgcgag cccgaaccgg acgtagccgt gttgacgtcc | 720 |
| atgctcactg atccctccca tataacagca gaggcggccg ggagaaggtt ggcgagaggg | 780 |
| tcacccccctt ctatggccag ctcctcggct agccagctgt ccgctccatc tctcaaggca | 840 |
| acttgcaccg ccaaccatga ctcccctgac gccgagctca tagaggctaa cctcctgtgg | 900 |
| aggcaggaga tgggcggcaa catcac | 926 |

<210> SEQ ID NO 137
<211> LENGTH: 850
<212> TYPE: DNA
<213> ORGANISM: Hepatitis C virus

<400> SEQUENCE: 137

| | |
|---|---:|
| actcagcagc ctcactgtaa cccagctcct gaggcgactg catcagtgga taagctcgga | 60 |
| gtgtaccact ccatgctccg gttcctggct aagggacatc tgggactgga tatgcgaggt | 120 |
| gctgagcgac tttaagacct ggctgaaagc caagctcatg ccacaactgc ctgggattcc | 180 |
| ctttgtgtcc tgccagcgcg gtatagggg ggtctggcga ggagacggca ttatgcacac | 240 |
| tcgctgccac tgtggagctg agatcactgg acatgtcaaa acgggacga tgaggatcgt | 300 |
| cggtcctagg acctgcagga acatgtggag tgggacgttc cccattaacg cctacaccac | 360 |
| gggcccctgt actcccttc ctgcgccgaa ctataagttc gcgctgtgga gggtgtctgc | 420 |
| agaggaatac gtggagataa ggcgggtggg ggacttccac tacgtatcgg gtatgactac | 480 |
| tgacaatctt aaatgcccgt gccagatccc atcgcccgaa ttttcacag aattggacgg | 540 |
| ggtgcgccta cacaggtttg cgcccccttg caagcccttg ctgcgggagg aggtatcatt | 600 |
| cagagtagga ctccacgagt acccggtggg gtcgcaatta ccttgcgagc ccgaaccgga | 660 |
| cgtagccgtg ttgacgtcca tgctcactga tccctcccat ataacagcag aggcggccgg | 720 |
| gagaaggttg gcgagagggt caccccttc tatggccagc tcctcggcta gccagctgtc | 780 |
| cgctccatct ctcaaggcaa cttgcaccgc caaccatgac tcccctgacg ccgagctcat | 840 |
| agaggctaac | 850 |

<210> SEQ ID NO 138
<211> LENGTH: 749
<212> TYPE: DNA
<213> ORGANISM: Hepatitis C virus

<400> SEQUENCE: 138

| | |
|---|---:|
| cagcctcact gtaacccagc tcctgaggcg actgcatcag tggataagct cggagtgtac | 60 |
| cactccatgc tccggttcct ggctaaggga catctgggac tggatatgcg aggtgctgag | 120 |
| cgactttaag acctggctga aagccaagct catgccacaa ctgcctggga ttcccttttgt | 180 |
| gtcctgccag cgcggtata ggggggtctg gcgaggagac ggcattatgc acactcgctg | 240 |

-continued

```
ccactgtgga gctgagatca ctggacatgt caaaaacggg acgatgagga tcgtcggtcc        300
taggacctgc aggaacatgt ggagtgggac gttccccatt aacgcctaca ccacgggccc        360
ctgtactccc cttcctgcgc cgaactataa gttcgcgctg tgagggtgt ctgcagagga         420 atacgtggag ataaggcggg tgggggactt ccactacgta tcgggtatga ctactgacaa       480
tcttaaatgc ccgtgccaga tcccatcgcc cgaattttc acagaattgg acggggtgcg         540
cctacacagg tttgcgcccc cttgcaagcc cttgctgcgg gaggaggtat cattcagagt       600
aggactccac gagtacccgg tggggtcgca attccttgc gagcccgaac cggacgtagc        660
cgtgttgacg tccatgctca ctgatccctc ccatataaca gcagaggcgg ccgggagaag       720
gttggcgaga gggtcacccc cttctatgg                                         749

<210> SEQ ID NO 139
<211> LENGTH: 257
<212> TYPE: DNA
<213> ORGANISM: Hepatitis C virus

<400> SEQUENCE: 139
gacctggctg aaagccaagc tcatgccaca actgcctggg attcccttg tgtcctgcca        60 gcgcgggtat aggggggtct ggcgaggaga cggcattatg cacactcgct gccactgtgg      120
agctgagatc actggacatg tcaaaaacgg acgatgagg atcgtcggtc ctaggacctg       180
caggaacatg tggagtggga cgttccccat taacgcctac accacgggcc ctgtactcc       240 ccttcctgcg ccgaact                                                     257

<210> SEQ ID NO 140
<211> LENGTH: 285
<212> TYPE: DNA
<213> ORGANISM: Hepatitis C virus

<400> SEQUENCE: 140
tgagatcact ggacatgtca aaaacgggac gatgaggatc gtcggtccta ggacctgcag       60
gaacatgtgg agtgggacgt tccccattaa cgcctacacc acgggcccct gtactcccct     120
tcctgcgccg aactataagt tcgcgctgtg agggtgtct gcagaggaat acgtggagat       180
aaggcgggtg ggggacttcc actacgtatc ggtatgact actgacaatc ttaaatgccc       240
gtgccagatc ccatcgcccg aattttttcac agaattggac gggt                      285

<210> SEQ ID NO 141
<211> LENGTH: 228
<212> TYPE: DNA
<213> ORGANISM: Hepatitis C virus

<400> SEQUENCE: 141
catagaggct aacctcctgt ggaggcagga gatgggcggc aacatcacca gggttgagtc       60
agagaacaaa gtggtgattc tggactcctt cgatccgctt gtggcagagg aggatgagcg     120
ggaggtctcc gtacctgcag aaattctgcg gaagtctcgg agattcgccc gggccctgcc     180
cgtctgggcg cggccggact acaacccccc gctagtagag acgtggaa                  228

<210> SEQ ID NO 142
<211> LENGTH: 273
<212> TYPE: DNA
<213> ORGANISM: Hepatitis C virus

<400> SEQUENCE: 142
```

```
ccatggctgc cgctaccac ctccacggtc ccctcctgtg cctccgcctc ggaaaaagcg      60
tacggtggtc ctcaccgaat caaccctatc tactgccttg gccgagcttg ccaccaaaag     120
ttttggcagc tcctcaactt ccggcattac gggcgacaat acgacaacat cctctgagcc     180
cgccccttct ggctgccccc ccgactccga cgttgagtcc tattcttcca tgccccccct     240 ggaggggggag cctggggatc cggatctcag cga                                  273
```

<210> SEQ ID NO 143
<211> LENGTH: 412
<212> TYPE: DNA
<213> ORGANISM: Hepatitis C virus

<400> SEQUENCE: 143

```
ttcctggaca ggcgcactcg tcaccccgtg cgctgcggaa gaacaaaaac tgcccatcaa      60
cgcactgagc aactcgttgc tacgccatca caatctggtg tattccacca cttcacgcag    120
tgcttgccaa aggcagaaga agtcacatt tgacagactg caagttctgg acagccatta    180
ccaggacgtg ctcaaggagg tcaaagcagc ggcgtcaaaa gtgaaggcta acttgctatc    240
cgtagaggaa gcttgcagcc tgacgccccc acattcagcc aaatccaagt ttggctatgg    300
ggcaaaagac gtccgttgcc atgccagaaa ggccgtagcc cacatcaact ccgtgtggaa    360
agaccttctg gaagacagtg taacaccaat agacactacc atcatggcca ag            412
```

<210> SEQ ID NO 144
<211> LENGTH: 903
<212> TYPE: DNA
<213> ORGANISM: Hepatitis C virus

<400> SEQUENCE: 144

```
ggctaacttg ctatccgtag aggaagcttg cagcctgacg cccccacatt cagccaaatc      60
caagtttggc tatggggcaa aagacgtccg ttgccatgcc agaaaggccg tagcccacat    120
caactccgtg tggaaagacc ttctggaaga cagtgtaaca ccaatagaca ctaccatcat    180
ggccaagaac gaggttttct gcgttcagcc tgagaagggg ggtcgtaagc cagctcgtct    240
catcgtgttc cccgacctgg gcgtgcgcgt gtgcgagaag atgggccctgt acgacgtggt    300 tagcaagctc cccctggccg tgatgggaag ctcctacgga ttccaatact caccaggaca    360
gcgggttgaa ttcctcgtgc aagcgtggaa gtccaagaag accccgatgg ggttctcgta    420 tgataccgc tgttttgact ccacagtcac tgagagcgac atccgtacgg aggaggcaat    480
ttaccaatgt tgtgacctgg accccaagcc cgcgtggcc atcaagtccc tcactgagag    540
gctttatgtt gggggccctc ttaccaattc aagggggggaa aactgcggct accgcaggtg    600
ccgcgcgagc ggcgtactga caactagctg tggtaacacc ctcacttgct acatcaaggc    660
ccgggcagcc tgtcgagccg cagggctcca ggactgcacc atgctcgtgt gtggcgacga    720
cttagtcgtt atctgtgaaa gtgcgggggt ccaggaggac gcggcagcc tgagagcctt    780 cacggaggct atgaccaggt actccgcccc ccccgggac ccccacaac cagaatacga    840 cttggagctt ataacatcat gctcctccaa cgtgtcagtc gcccacgacg gcgctggaaa    900
gag                                                                  903
```

<210> SEQ ID NO 145
<211> LENGTH: 600
<212> TYPE: DNA
<213> ORGANISM: Hepatitis C virus

<400> SEQUENCE: 145

```
agaggaagct tgcagcctga cgcccccaca ttcagccaaa tccaagtttg gctatggggc    60
aaaagacgtc cgttgccatg ccagaaaggc cgtagcccac atcaactccg tgtggaaaga   120
ccttctggaa gacagtgtaa caccaataga cactaccatc atggccaaga acgaggtttt   180
ctgcgttcag cctgagaagg ggggtcgtaa gccagctcgt ctcatcgtgt tccccgacct   240
gggcgtgcgc gtgtgcgaga agatggccct gtacgacgtg gttagcaagc tcccctggc    300 cgtgatggga agctcctacg gattccaata ctcaccagga cagcgggttg aattcctcgt   360
gcaagcgtgg aagtccaaga agaccccgat ggggttctcg tatgataccc gctgttttga   420
ctccacagtc actgagagcg acatccgtac ggaggaggca atttaccaat gttgtgacct   480
ggacccccaa gcccgcgtgg ccatcaagtc cctcactgag aggctttatg ttgggggccc   540
tcttaccaat tcaagggggg aaaactgcgg ctaccgcagg tgccgcgcga gcggcgtact   600
```

```
<210> SEQ ID NO 146
<211> LENGTH: 781
<212> TYPE: DNA
<213> ORGANISM: Hepatitis C virus

<400> SEQUENCE: 146
ccttctggaa gacagtgtaa caccaataga cactaccatc atggccaaga acgaggtttt    60
ctgcgttcag cctgagaagg ggggtcgtaa gccagctcgt ctcatcgtgt tccccgacct   120
gggcgtgcgc gtgtgcgaga agatggccct gtacgacgtg gttagcaagc tcccctggc    180 cgtgatggga agctcctacg gattccaata ctcaccagga cagcgggttg aattcctcgt   240
gcaagcgtgg aagtccaaga agaccccgat ggggttctcg tatgataccc gctgttttga   300
ctccacagtc actgagagcg acatccgtac ggaggaggca atttaccaat gttgtgacct   360
ggacccccaa gcccgcgtgg ccatcaagtc cctcactgag aggctttatg ttgggggccc   420
tcttaccaat tcaagggggg aaaactgcgg ctaccgcagg tgccgcgcga gcggcgtact   480
gacaactagc tgtggtaaca ccctcacttg ctacatcaag gcccgggcag cctgtcgagc   540
cgcagggctc caggactgca ccatgctcgt gtgtggcgac gacttagtcg ttatctgtga   600
aagtgcgggg gtccaggagg acgcggcgag cctgagagcc ttcacggagg ctatgaccag   660
gtactccgcc ccccccgggg acccccccaca accagaatac gacttggagc ttataacatc   720
atgctcctcc aacgtgtcag tcgcccacga cggcgctgga agagggtct actaccttac   780 c                                                                    781
```

```
<210> SEQ ID NO 147
<211> LENGTH: 382
<212> TYPE: DNA
<213> ORGANISM: Hepatitis C virus

<400> SEQUENCE: 147
cgttatctgt gaaagtgcgg gggtccagga ggacgcggcg agcctgagag ccttcacgga    60
ggctatgacc aggtactccg cccccccgg ggacccccca caaccagaat acgacttgga   120
gcttataaca tcatgctcct ccaacgtgtc agtcgcccac gacggcgctg gaaagagggt   180
ctactacctt acccgtgacc ctacaacccc cctcgcgaga gccgcgtggg agacagcaag   240
acacactcca gtcaattcct ggctaggcaa cataatcatg tttgccccca cactgtgggc   300
gaggatgata ctgatgaccc atttctttag cgtcctcata gccagggatc agcttgaaca   360
ggctcttaac tgtgagatct ac                                             382
```

<210> SEQ ID NO 148
<211> LENGTH: 268
<212> TYPE: DNA
<213> ORGANISM: Hepatitis C virus

<400> SEQUENCE: 148

| | |
|---|---:|
| cgtgtcagtc gcccacgacg gcgctggaaa gagggtctac taccttaccc gtgaccctac | 60 |
| aaccccctc gcgagagccg cgtgggagac agcaagacac actccagtca attcctggct | 120 |
| aggcaacata atcatgtttg cccccacact gtgggcgagg atgatactga tgacccattt | 180 |
| ctttagcgtc ctcatagcca gggatcagct tgaacaggct cttaactgtg agatctacgg | 240 |
| agcctgctac tccatagaac cactggat | 268 |

<210> SEQ ID NO 149
<211> LENGTH: 222
<212> TYPE: DNA
<213> ORGANISM: Hepatitis C virus

<400> SEQUENCE: 149

| | |
|---|---:|
| actccatggc ctcagcgcat tttcactcca cagttactct ccaggtgaaa tcaataggt | 60 |
| ggccgcatgc ctcagaaaac ttggggtccc gcccttgcga gcttggagac accgggcccg | 120 |
| gagcgtccgc gctaggcttc tgtccagagg aggcagggct gccatatgtg gcaagtacct | 180 |
| cttcaactgg gcagtaagaa caaagctcaa actcactcca at | 222 |

<210> SEQ ID NO 150
<211> LENGTH: 192
<212> TYPE: DNA
<213> ORGANISM: Hepatitis C virus

<400> SEQUENCE: 150

| | |
|---|---:|
| ctctccaggt gaaatcaata gggtggccgc atgcctcaga aaacttgggg tcccgccctt | 60 |
| gcgagcttgg agacaccggg cccggagcgt ccgcgctagg cttctgtcca gaggaggcag | 120 |
| ggctgccata tgtggcaagt acctcttcaa ctgggcagta agaacaaagc tcaaactcac | 180 |
| tccaatagcg gc | 192 |

<210> SEQ ID NO 151
<211> LENGTH: 10
<212> TYPE: DNA
<213> ORGANISM: Artificial Sequence
<220> FEATURE:
<223> OTHER INFORMATION: Description of Artificial Sequence: linker sequence

<400> SEQUENCE: 151

| | |
|---|---:|
| gggccacgaa | 10 |

<210> SEQ ID NO 152
<211> LENGTH: 13
<212> TYPE: DNA
<213> ORGANISM: Artificial Sequence
<220> FEATURE:
<223> OTHER INFORMATION: Description of Artificial Sequence: linker sequence

<400> SEQUENCE: 152

| | |
|---|---:|
| ttcgtggccc ctg | 13 |

<210> SEQ ID NO 153
<211> LENGTH: 138

```
<212> TYPE: DNA
<213> ORGANISM: Artificial Sequence
<220> FEATURE:
<223> OTHER INFORMATION: Description of Artificial Sequence: pP6 vector
      sequence

<400> SEQUENCE: 153
ctagccatgg ccgcaggggc cgcggccgca ctagtgggga tccttaatta aagggccact    60 ggggccccc gtaccggcgt ccccggcgcc ggcgtgatca ccctaggaa ttaatttccc    120 ggtgaccccg ggggagct                                                 138

<210> SEQ ID NO 154
<211> LENGTH: 128
<212> TYPE: DNA
<213> ORGANISM: Artificial Sequence
<220> FEATURE:
<223> OTHER INFORMATION: Description of Artificial Sequence: pB5 vector
      sequence

<400> SEQUENCE: 154
catggccgca ggggccgcgg ccgcactagt ggggatcctt aattaaaggg ccactggggc    60 ccccggcgt ccccggcgcc ggcgtgatca ccctaggaa ttaatttccc ggtgaccccg    120
ggggagct                                                            128

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 155
gcgtttggaa tcactacagg                                               20

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 156
cacgatgcac gttgaagtg                                                19
```

US 6,977,144 B2

SID NUCLEIC ACIDS AND POLYPEPTIDES SELECTED FROM A PATHOGENIC STRAIN OF HEPATITIS C VIRUS AND APPLICATIONS THEREOF

FIELD OF THE INVENTION

The present invention relates to nucleic acids encoding SID® polypeptides which bind selectively to a polypeptide encoded by a pathogenic strain of the hepatitis C virus, as well as to the SID® polypeptides which are encoded by said nucleic acids.

The invention also concerns vectors comprising a nucleic acid encoding a SID® polypeptide as well as host cells transformed with such vectors.

The invention is also directed to two-hybrid methods which make use of the nucleic acids encoding a SID® polypeptide selected from a pathogenic strain of the hepatitis C virus as well as to methods for selecting molecules which inhibit the binding between a SID® polypeptide and a polypeptide which specifically binds thereto.

The invention also pertains to marker compounds containing a SID® polypeptide as well as nucleic acids encoding such marker compounds and methods and kits using the same.

BACKGROUND OF THE INVENTION

The hepatitis C virus (HCV) causes several liver diseases, including liver cancer. The HCV genome is a plus-stranded RNA that encodes the single polyprotein processed into at least 10 mature polypeptides.

The structural proteins are located in the amino terminal quarter of the polyprotein, and the non-structural (NS) polypeptides in the remainder (for a review, see HOUGHTON, 1996). The genome organisation resembles that of flaviviruses and pestiviruses and HCV is now considered to be a member of the flaviviridae family.

The gene products of HCV are, from the N-terminus to the C-terminus: core (p22), E1 (gp35), E2 (gp70), NS2(p21), NS3 (p70), NS4a (p4), NS4b(p27), NS5a (p58), NS5b (p66), as disclosed in FIG. 1. Core, E1and E2 are the structural proteins of the virus processed by the host signal peptidase(s). The core protein and the genomic RNA constitute the internal viral core and E1 and E2 together with lipid membrane constitute the viral envelop (DUBUISSON et al., 1994; GRAKOUI et al., 1993; HIGIKATA et al., 1993.).

The NS proteins are processed by the viral protein NS3 which has two functional domains: one (Cro-1), encompassing the NS2 region and the N-terminal portion of NS3, which cleaves autocatalytically between NS2 and NS3, and the other (Cro-2), located solely in the N-terminal portion of NS3, cleaves the other sites downstream NS3 (BARTENSCHLAGER et al; 1995; HIGIKATA et al;, 1993).

Various HCV protein-protein interactions have already been identified, notably by two hybrid methods. Noticeably, FLAJOLET et al; (2000) have shown interactions between NS3 and NS4A proteins as well as between NS4A and NS2 proteins. These authors have also shown core-core, NS3-E2, NS5A-E1, NS4A-NS3 and NS4A-NS2 interactions. Covalent as well as non-covalent interactions between E1 and E2 have been shown by PATEL et al; (1999). The protein interactions between NS3 and the HCV RNA helicase have also been described (MIN et al; 1999; GALLINARI et al., 1999) as well as interaction between NS3 and NS4A (URBANI et al., 1999; DI MARCO et al., 2000; BUTKIEWICZ et al., 2000).

However, the prior art methods allow the determination of interactions between full length proteins or large domains of proteins encoded by the genome of the hepatitis C virus which may contain more than one region of interaction with one or several HCV proteins. BUTKIEWICZ et al. (2000) discloses the interaction between the NS3 protease and a small peptide derived from NS4A. However, BUTKIEWICZ et al. (2000) discloses exclusively in vitro assays for interactions between the small peptides derived from NS4A and the NS3 protease from HCV which may not be of physiological relevance.

There is a need in the art for polypeptides that contain the minimal aminoacid sequence that is able to bind specifically with a naturally-occurring HCV protein in physiological conditions in order to design new tools for therapeutic and detection purposes related to HCV.

SUMMARY OF THE INVENTION

This invention provides nucleic acids encoding polypeptides, which are termed SID® polypeptides, wherein these polypeptides are the final products of a double selection method involving a first step of selection of HCV-derived polynucleotides through a two-hybrid system and a second selection step involving an alignment between the different polynucleotides selected at the first step.

The invention also pertains to the SID® polypeptides encoded by the SID® nucleic acids.

Another object of the invention are recombinant vectors containing a SID® nucleic acid as defined above as well as host cells transformed with such vectors or nucleic acids.

A further object of the invention consists of two-hybrid methods which make use of these SID® nucleic acids as well as to methods for selecting molecules which inhibit the binding between a SID® polypeptide and a polypeptide that binds specifically thereto, as well as kits for performing these methods.

It is still a further object of the invention to provide for marker compounds which comprise a SID® polypeptide or which are encoded by a polynucleotide containing a SID® nucleic acid as defined above, as well as to methods and kits which make use of these marker compounds.

This invention also relates to pharmaceutical compositions as well as to methods for preventing or curing a HCV viral infection in a human or an animal that use a SID® polypeptide or a SID® nucleic acid as disclosed herein.

Throughout this application, various publications, patents and published patent applications are cited. The disclosures of these publications, patents and published patent specifications, referenced in this application are hereby incorporated by reference into the present disclosure to more fully describe the state of the art to which this invention pertains.

Positions and enzymes responsible for cleavage are indicated above. p7 is a secondary cleavage product of E2 (adapted from HOUGHTON, 1996).

Figure 1:
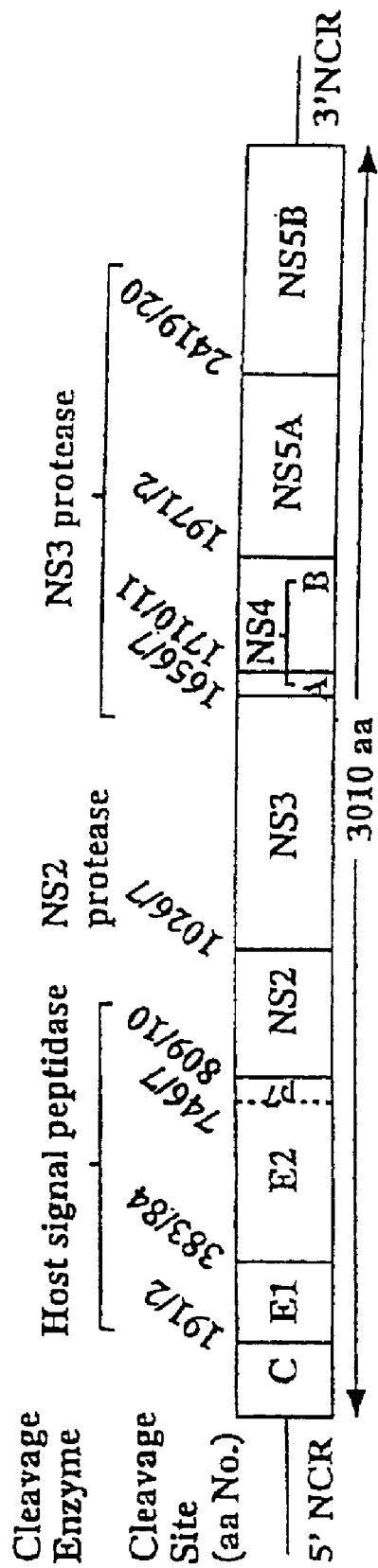
FIG. 1 consists of a general overview of HCV genome and its encoded polyprotein. The RNA coding strand is represented with a line for untranslated regions (NCR) and boxes for coding regions.
Figure 2:
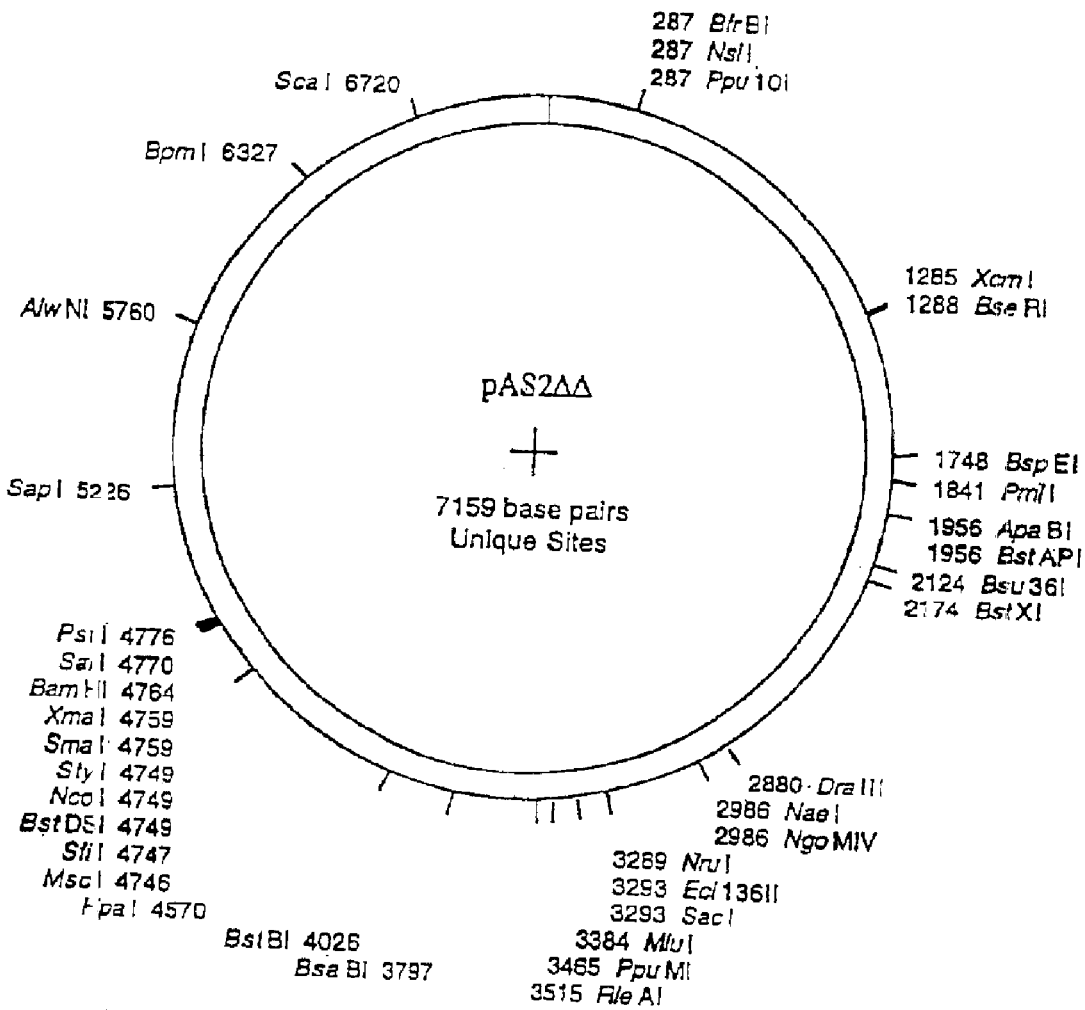

FIG. 2 is a restriction map of the plasmid pAS2ΔΔ which may be used for producing a recombinant "Selected Interacting Domain (SID®)" polypeptide or a recombinant marker compound of the invention.

Figure 3:
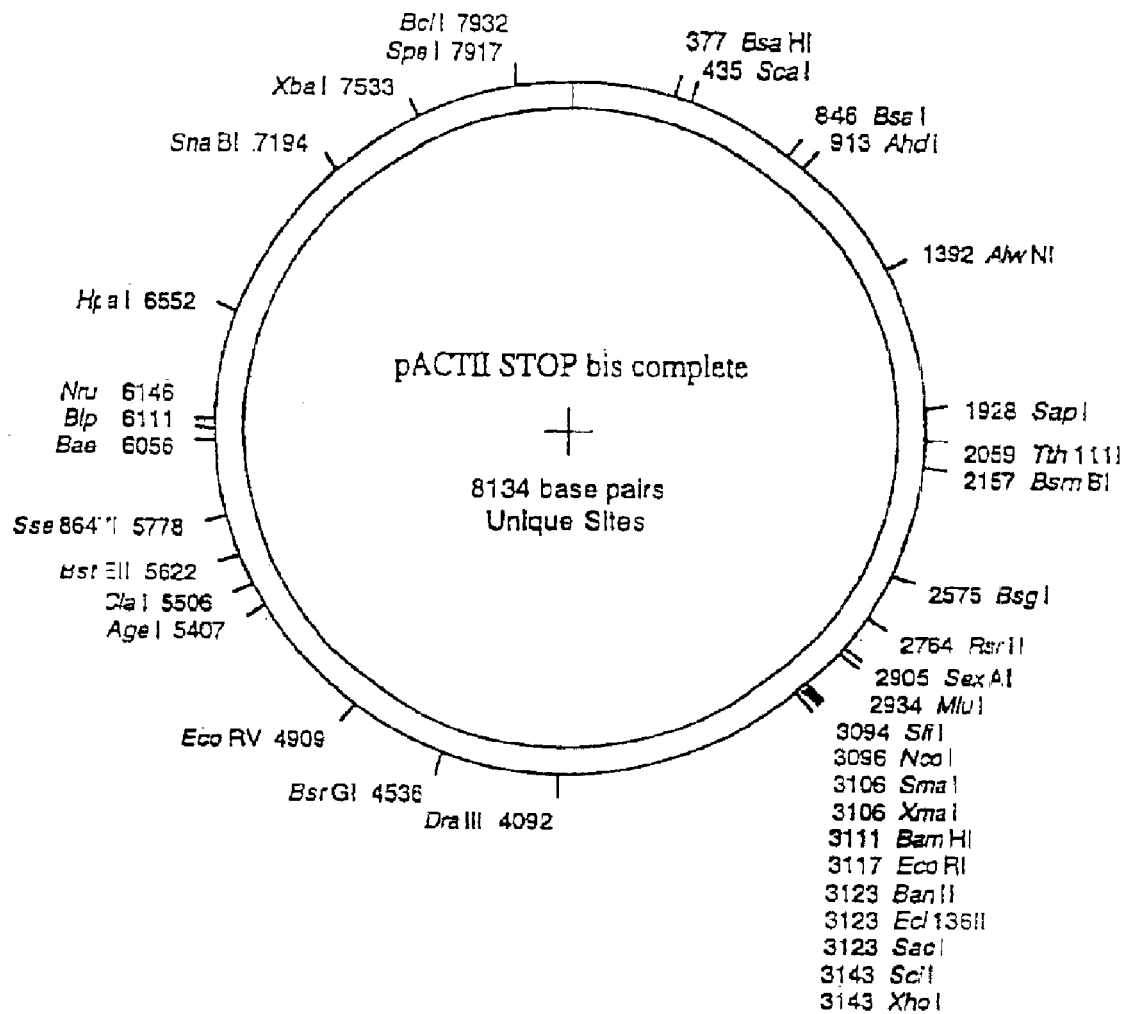

FIG. 3 is a restriction map of the plasmid pACTII which may be used for producing a recombinant "Selected Interacting Domain (SID®)".

FIG. 4 is a restriction map of the plasmid pUT18 which may be used for producing a recombinant "Selected Interacting Domain (SID®)".

FIG. 5 is a restriction map of the plasmid pUT18C which may be used for producing a recombinant "Selected Interacting Domain (SID®)".

Figure 6:
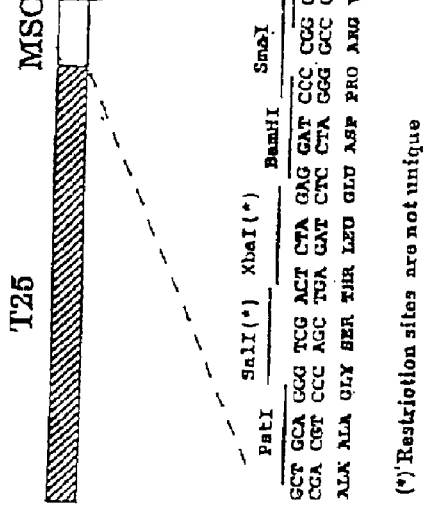

FIG. 6 is a restriction map of the plasmid pT25 which may be used for producing a recombinant "Selected Interacting Domain (SID®)".

Figure 7:
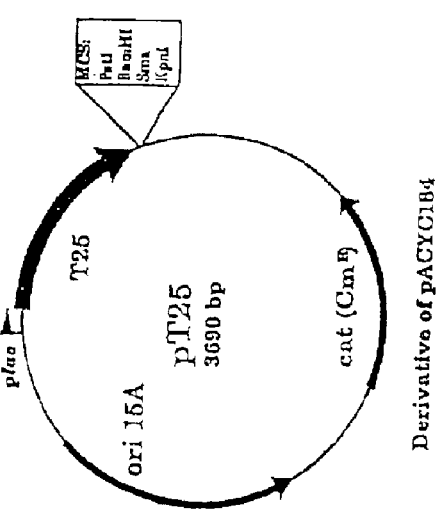
Figure 7:
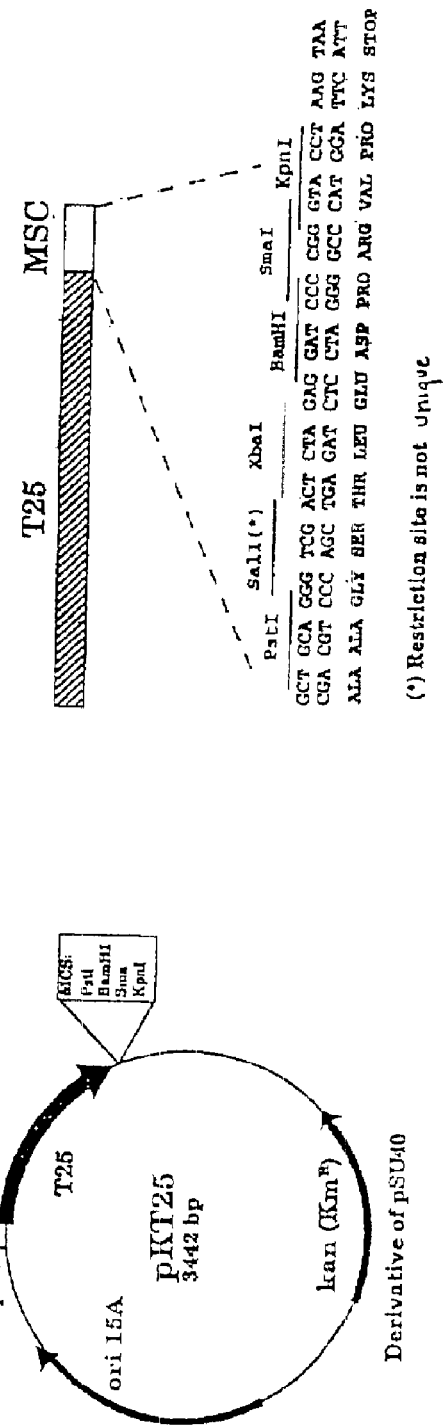

FIG. 7 is a restriction map of the plasmid pKT25 which may be used for producing a recombinant "Selected Interacting Domain (SID®)".

Figure 8:
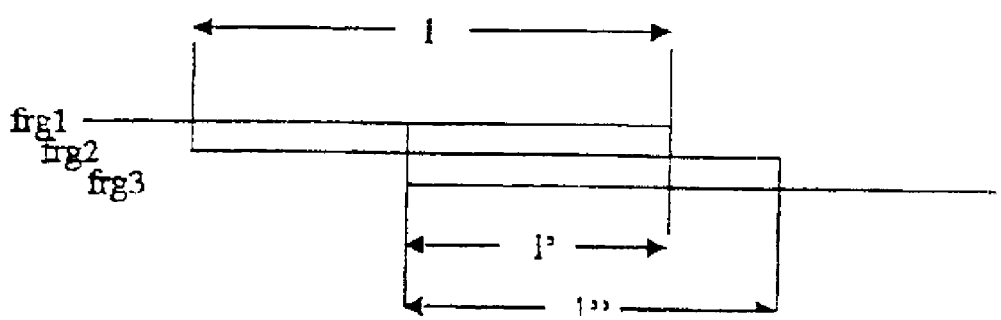

FIG. 8 is an illustration of the first step of selecting a SID® nucleic acid of the invention, wherein it is performed a selection of different sets of overlapping nucleic acids primarily selected through a two-hybrid method, in order to define pre-SID nucleic acids. Three fragments frg1, frg2 and frg3 of lengths l1, l2 and l3 respectively. Fragment l1 and l2 are clustered together if the length of intersection, I, is greater than 30% of l1 and l2. Fragment frg3 is grouped with fragments frg and frg2 if the length of intersection between frg1 and frg3, l', is greater than 30% of l1 and l3 and if the length of intersection between frg 2 and frg 3, l>>, is greater than 30% of l2 and l3.

Figure 9:
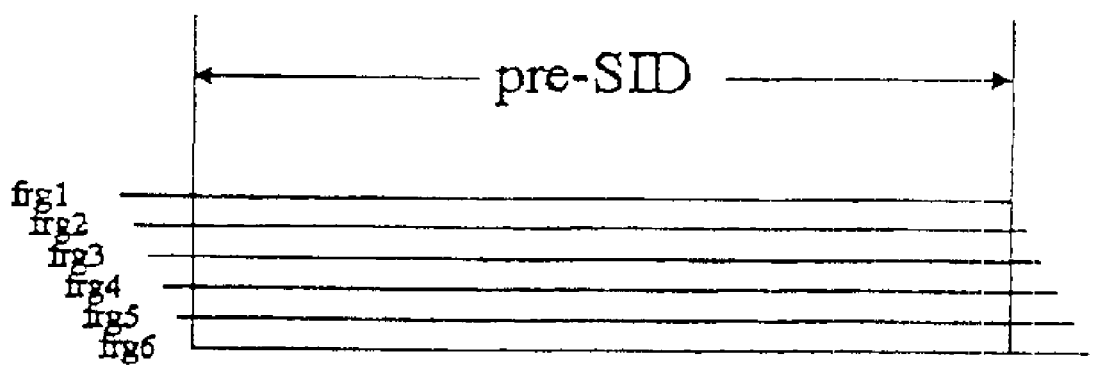

FIG. 9 illustrates the selection of pre-SID® nucleic acid from a particular set of overlapping nucleic acids previously selected through a two-hybrid method. The pre-SID® is defined as the intersection of all the fragments (frg1–6) in a cluster.

Figure 10:
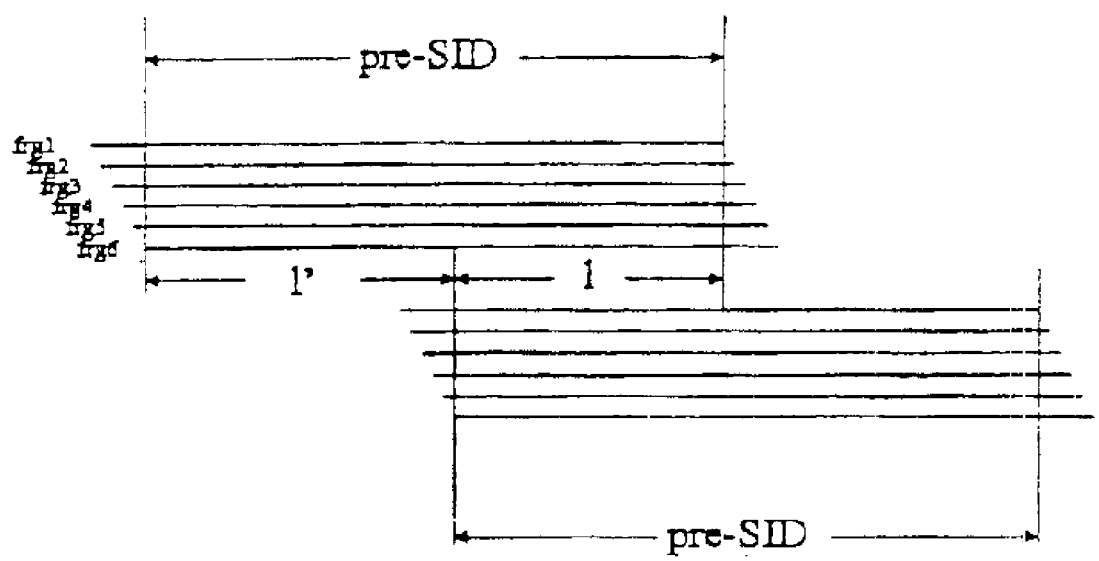

FIG. 10 illustrates the selection of a SID® nucleic acid from the overlapping regions between two pre-SID nucleic acids. A SID® is defined if the length of overlap between two pre-SID®s, l, is greater than 30 bp. Further SID®s are defined by non-overlapping areas if their length (l') represents more than 30% of the length of one of the fragments which contributes to the corresponding pre-SID® (frg1–6).

Figure 11:
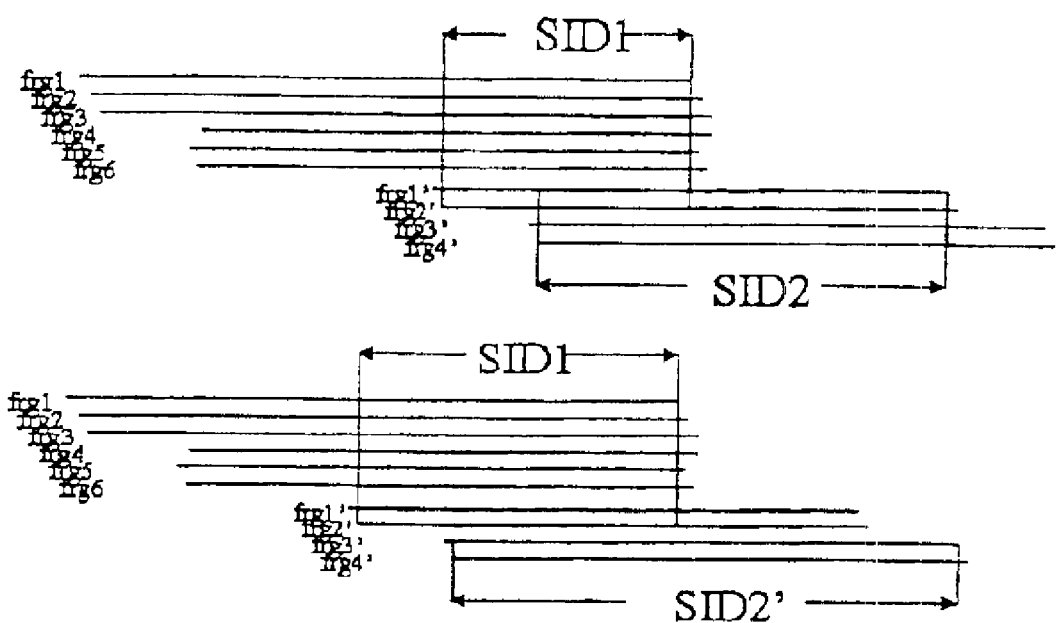

FIG. 11 illustrates a further step of determining SID® nucleic acids after alignment of two overlapping SID nucleic acids identified according to FIG. 10. Fragments frg1' and frg2' contribute to both SID®1 and SID®2 (top panel). For each SID®, the number of fragments are counted and fragments are assigned to the SID® with the most fragments. The remaining fragments are re-analysed and a new SID® is defined as the region of intersection of these fragments (bottom panel, SID®2'—fragment 3' and fragment 4'.

Figure 12:
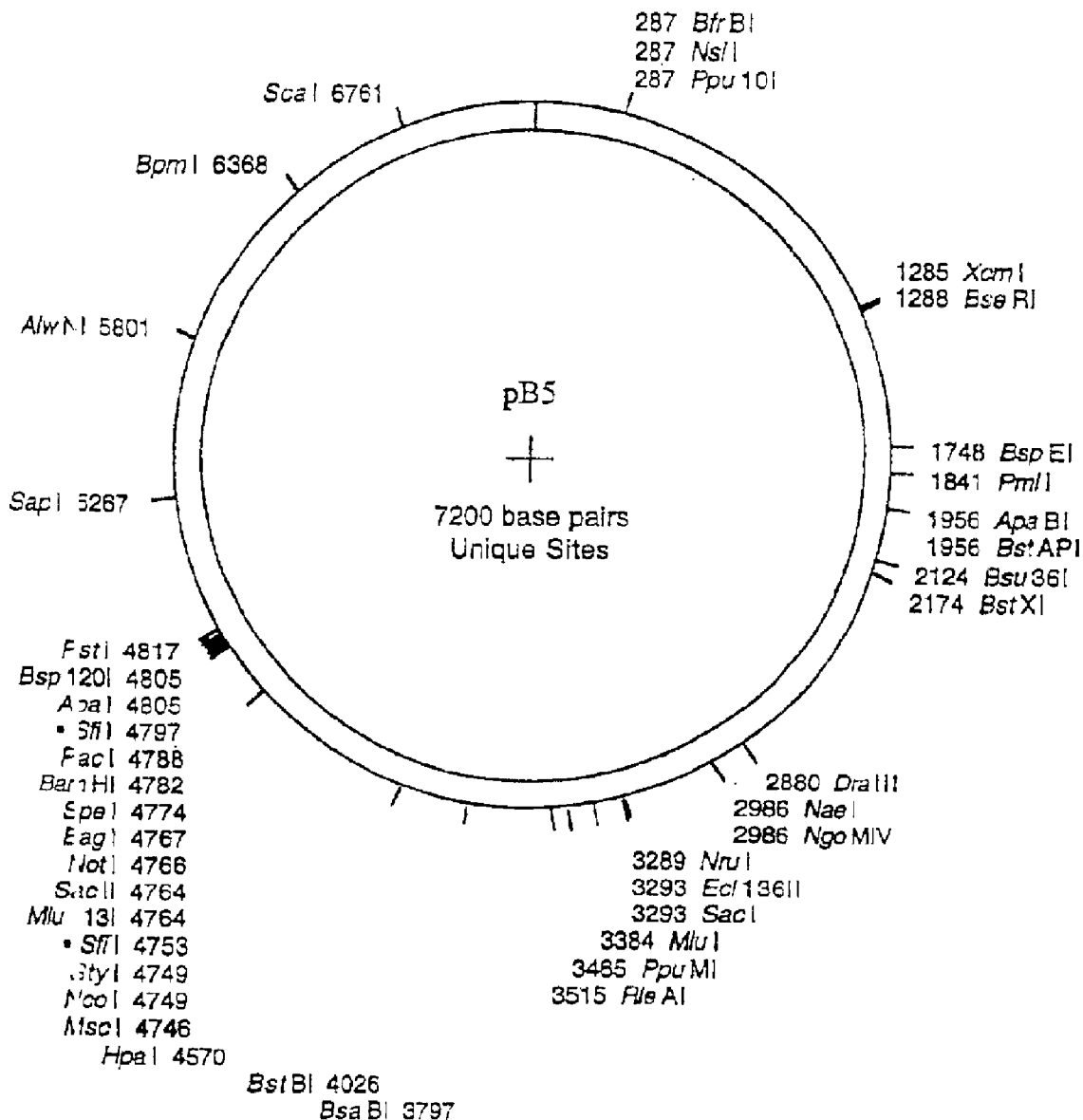

FIG. 12 illustrates a map of the vector pB5 which may be used in example 1.

Figure 13:
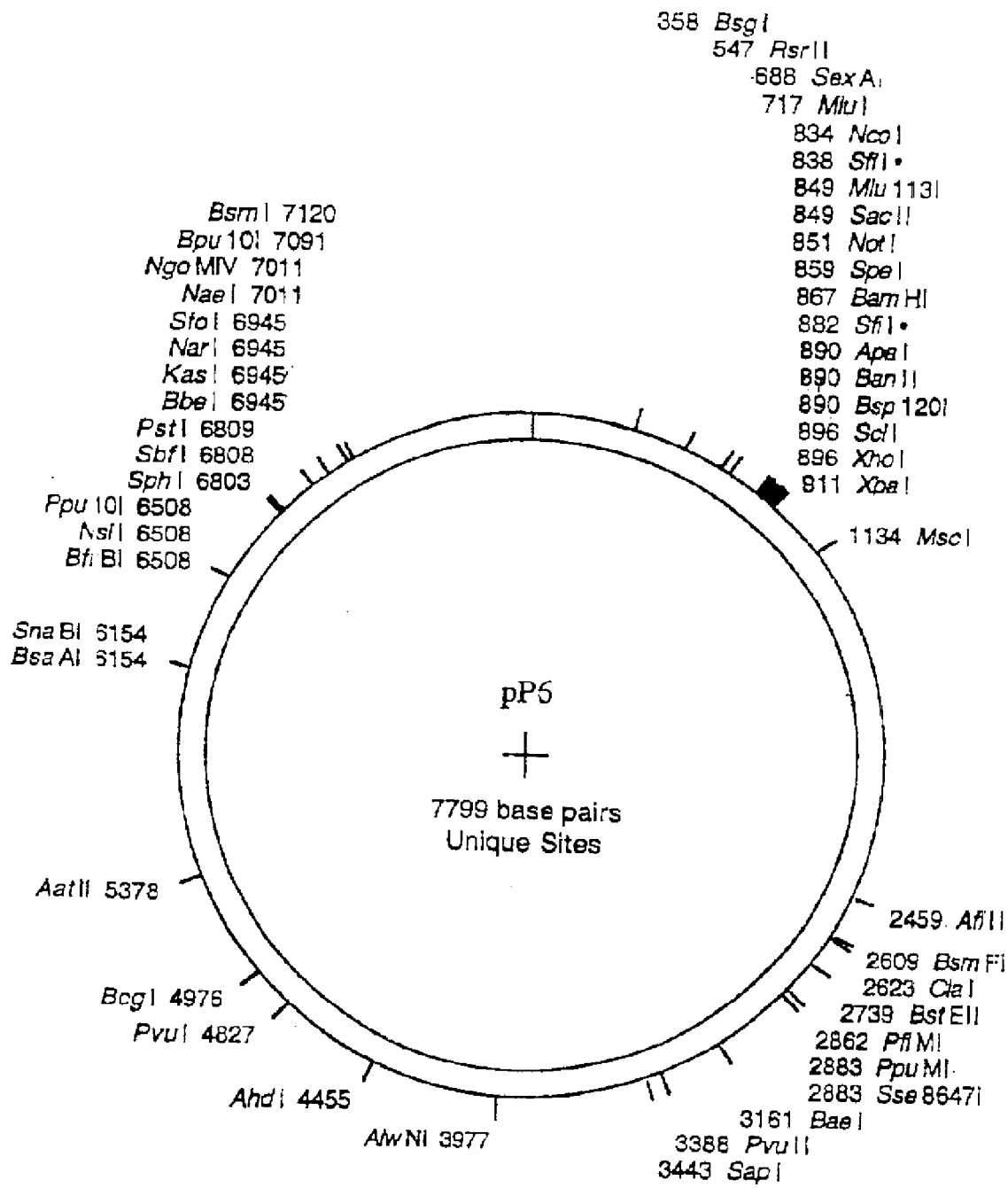

FIG. 13 illustrates a map of the vector pP6 which may be used in example 1.

DETAILED DESCRIPTION OF THE INVENTION

The present invention firstly provides for nucleic acids encoding SID® polypeptides.

As generally used herein, a <<bait>> nucleic acid encodes a <<bait>> polypeptide. A polypeptide is termed a <<bait>> polypeptide when this polypeptide is used to select a formerly unknown <<prey>> nucleic acid encoding a <<prey>> polypeptide which binds selectively with said <<bait>> polypeptide. Indeed, a <<prey>> nucleic acid which has been selected for binding to a given bait polypeptide may be used in another selection method or in another round of the same selection method as a <<bait>> nucleic acid encoding a <<bait>> polypeptide for the purpose of selection of new prey nucleic acids, encoding prey polypeptides which bind selectively with said bait polypeptide, it being understood that the nucleic acid encoding said bait polypeptide was formerly selected from a population of prey nucleic acids.

Selected Interacting Domain (SID®) Polypeptides and Methods for their Preparation A selected interacting domain polypeptide that binds specifically to a polypeptide of interest is the result of a two-step screening procedure, wherein:

1) the first step consists of selecting and characterizing a collection of nucleic acids (prey nucleic acids) encoding polypeptides which bind specifically to a given bait polypeptide of interest; and 2) the second step of the two-step procedure consists of determining the nucleic acid sequences which encode for SID® polypeptides after having generated sets of polynucleotides from the collection of nucleic acids selected at step 1).

As a result of the original two-step screening procedure disclosed hereunder, every nucleic acid finally selected encodes a <<Selected Interacting Domain (SID®)" polypeptide which binds with a high specificity with the bait polypeptide of interest.

Step 1) Selecting Prey Nucleic Acids

The first step of selecting a collection of nucleic acids encoding polypeptides which binds specifically to the bait polypeptide is carried out through a yeast two-hybrid system. The yeast two-hybrid system is designed to study protein-protein interactions in vivo, and relies upon the fusion of a bait protein to the DNA binding domain of the yeast Gal4 protein.

According to the present invention, the first step of the procedure for selecting a Selected Interacting Domain (SID®) polynucleotide encoding a Selected Interacting Domain (SID®) polypeptide consists of the two-hybrid screening system described by Fromont-Racine et al. (1997) or the method described by FLAJOLET et al. (2000). The yeast two-hybrid system utilizes hybrid proteins to detect protein-protein interactions by means of direct activation of a reporter gene expression. In essence, the nucleic acids encoding the two putative protein partners, the bait polypeptide of interest and the prey polypeptide, are genetically fused to the DNA-binding domain of a transcription factor and to a transcriptional activation domain, respectively.

Construction of the Prey HCV Nucleic Acids Library.

Then, a genomic DNA library prepared from the genome of the pathogenic H77 strain of HCV (Yanagi et al., 1997), is constructed in the specially designed vector pP6 shown in FIG. 13 after ligation to suitable linkers, such that every genomic DNA insert is fused to a nucleotide sequence in the vector that encodes the transcription of domain of the Gal4 protein.

The polypeptides encoded by the nucleotide inserts of the genomic DNA library thus prepared are termed "prey" polypeptides in the context of the presently described selection method of prey nucleic acids.

Construction of the Bait Nucleic Acids Library

The DNA fragments obtained after nebulization of the HCV genomic DNA are also inserted in plasmid pB5 shown in FIG. 12 wherein these DNA inserts are fused to a polynucleotide encoding the DNA binding domain of the Gal4 protein and the recombinant vectors are used to transform *E. coli* cells. The transformed *E. coli* cells are grown and plasmid DNA is extracted and sequenced.

These plasmids which code in frame fusion proteins are used as bait plasmids. Bait plasmids thus consist of a collection of recombinant pB5 plasmids each containing inserted therein a DNA fragment from the H77 strain HCV genome encoding a polypeptide consisting of all or part of a HCV protein or alternatively a polypeptide consisting of all or part of two HCV proteins encoded by contiguous nucleic acid sequences of the HCV genome.

The selected HCV bait nucleic acids of the invention are referred to as the nucleotide sequences SEQ ID N°114 to 150.

The selected HCV bait polypeptides encoded by the nucleic sequences SEQ ID N°114 to 150 consist respectively of the aminoacid sequences SEQ ID N°77 to 113.

Detectable marker genes are already present within the chromosomic yeast DNA and consist respectively of the His3 and LacZ genes, such as described by FROMONT-RACINE et al. (1997) or FLAJOLET et al. (2000).

Then, the collection of nucleic acid inserts contained in the collection of *E. Coli* cell clones containing the genomic DNA or HCV DNA library previously prepared are used to transform a first yeast strain, namely the Y187 *Saccharomyces cerevisiae* strain (phenotype:MATα, Gal4Δ, gal80Δ, ade2-101, His3, Leu2-3, -112 Trp1-901, Ura3-52, URA3::UASGAL1-LacZ Met).

The nucleic acid encoding the bait polypeptide of interest is inserted in the appropriate vector, said vector being used to transform a second yeast strain which may be the CG1945 (MATa Gal4-542 Gal180-538, Ade2-101, His3*200, Leu2-3, -112 Trp1-901 Ura3-52, Lys2-801, URA3::GAL4 17Mers (X3)-CyC1TATA-LacZ LYS2::GAL1 UAS-GAL1TATA-His3 CYH$^R$).

Then, the two yeast strains are mated to obtain a collection of mated cells.

The clones derived from the collection of mated cells above which are positive in an X-Gal overlay assay are those for which an interaction between the recombinant bait polypeptide and a polypeptide encoded by a nucleic acid insert originating from the HCV genomic library has occurred.

The clones derived from the collection of mated cells above may also be selected in the presence of histidine, and the positive clones are those for which an interaction between the recombinant bait polypeptide and a polypeptide encoded by a nucleic acid insert originating from the HCV genomic library has occurred.

In a further step, the prey nucleic acid inserts contained in the positively selected clones are amplified and sequenced.
Step 2: Determination of the Nucleic Acid Sequences Encoding a Selected Interacting Domain (SID®) Polypeptide which Binds Specifically to a Bait Polypeptide of Interest.

This is the second step of the two step procedure defined above, which allows the precise selection of nucleic acids encoding the SID® nucleic acids of the present invention which are derived from the H77 strain HCV genome.

The SID® nucleic acid selection procedure, which is disclosed hereunder, has been specifically designed for the HCV genome which encodes for a single polyprotein and which thus comprises contiguous Open Reading Frames, said polyprotein being further processed to produce at least 10 mature structural and non-structural viral proteins.

Thus, the second selection step of the two-step procedure consists of a method for determining a polynucleotide encoding a Selected Interacting Domain (SID®) of a prey polypeptide of interest derived from HCV, which prey polypeptide interacts with a bait polypeptide, wherein said method comprises the steps of:

a) selecting, from the collection of prey polynucleotides obtained at the end of the first step of the two-step procedure described herein, all prey polynucleotides encoding a prey polypeptide capable of interacting with said bait polypeptide and containing a common nucleic acid fragment;

b) aligning the nucleotide sequences of the prey polynucleotides selected at step a) and gathering in one set or in a plurality of sets of sequences those nucleotide sequences which have sequences that overlap for more than 30% of their respective nucleic acid length, wherein each common overlapping nucleotide sequence in one set of sequences defines a sequence encoding a pre-SID® polypeptide (see FIGS. 8 and 9); and c) aligning two sequences encoding two respective pre-SID® polypeptides (see FIG. 10), and:

i) defining an overlapping nucleic acid sequence between the sequences encoding the two respective pre-SID® polypeptides as a sequence encoding a SID® polypeptide, provided that the overlapping sequence is of at least 30 nucleotides in length;

ii) defining a non-overlapping nucleic acid sequence between the sequences encoding the two respective pre-SID® polypeptides as a sequence encoding a SID® polypeptide, provided that (1) said non-overlapping sequence has more than 30 nucleotides in length and (2) said non-overlapping sequence represents at least 30% in length of any one of the polynucleotides contained in the set of prey polynucleotides used for defining the sequence encoding each pre-SID® polypeptide.

This method may further comprise the steps of:

d) counting the number of overlapping prey polynucleotides contained in a first set of polynucleotides defining a sequence encoding a first SID® polypeptide;

e) counting the number of overlapping prey polynucleotides contained in a second set of polynucleotides defining a sequence encoding a second SID® polypeptide which overlaps with the sequence encoding the first SID® polypeptide;

f) determining which sequence among those encoding respectively the first SID® polypeptide and the second SID® polypeptide has been defined with the largest number of prey polynucleotides and selecting this set of prey sequences.

g) adding to the set of prey sequences selected at step f) those sequences that were contained in the set of prey sequences used for defining the sequence encoding the SID® polypeptide with the smallest number of prey sequences and which overlap with the sequence encoding the SID® polypeptide with the largest number of prey sequences;

h) aligning the prey sequences added at step g) with the sequences already contained in the set of prey sequences which defined the sequence encoding the SID® polypeptide with the largest number of prey sequences;

i) defining an overlapping sequence between the whole sequences which were aligned in step h), wherein said overlapping sequence consists of a sequence encoding a SID® polypeptide. (See FIG. 11).

The method for selecting a SID® nucleic acid encoding a SID® polypeptide is an object of the present invention, as well as any SID® nucleic acid or any SID® polypeptide which may be obtained by this selection method.

SID® Nucleic Acids of the Invention

The SID® nucleic acids selected as described above starting from the genome of the H77 strain of HCV are the nucleic acid sequences of SEQ ID N°39 to 76 which encode the SID® polypeptides of SEQ ID N°1 to 38.

A first object of the invention consists of a nucleic acid which encodes a polypeptide selected from the group consisting of the aminoacid sequences SEQ ID N°1 to 38 or a variant thereof, and a sequence complementary thereto.

For the purposes of the present invention, a first polynucleotide is considered as being <<complementary>> to a second polynucleotide when each base of the first polynucleotide is paired with the complementary base of the second polynucleotide whose orientation is reversed. The complementary bases are A and T(or A and U), or C and G.

Preferably, any one of the nucleic acid or the polypeptides encompassed by the invention is under a purified or an isolated form.

The term "isolated" for the purposes of the present invention designates a biological material (nucleic acid or protein) which has been removed from its original environment (the environment in which it is naturally present).

For example, a polynucleotide present in the natural state in a plant or an animal is not isolated. The same polynucleotide separated from the adjacent nucleic acids in which it is naturally inserted in the genome of the plant or animal is considered as being "isolated".

Such a polynucleotide may be included in a vector and/or such a polynucleotide may be included in a composition and remains nevertheless in the isolated state because of the fact that the vector or the composition does not constitute its natural environment.

The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

"Isolated polypeptide" or "isolated protein" is a polypeptide or protein which is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilisers, or compounding into a pharmaceutically acceptable preparation.

Variants of a Selected Interacting Domain (SID®) Polypeptide and Nucleic Acids Encoding them.

As intended herein, a variant of a Selected Interacting Domain (SID®) polypeptide may be either a variant polypeptide of the Selected Interacting Domain (SID®) polypeptide or a polypeptide which is encoded by a nucleic acid variant of the polynucleotide encoding said Selected Interacting Domain (SID®) polypeptide.

Polynucleotides which encode a polypeptide variant of a Selected Interacting Domain (SID®) polypeptide, as the term is used herein, are polynucleotides that differ from the reference polynucleotide encoding the parent SID® polypeptide. A variant of a polynucleotide may be a naturally occurring variant such as a naturally occurring allelic variant, or it may be a variant that is not known to occur naturally. Such non-naturally occurring variants of the reference polynucleotide may be generated by mutagenesis techniques, including those applied to polynucleotides, cells or organisms well known to one skilled in the art.

Generally, differences are limited so that the nucleotide sequences of the reference and the variant are closely similar overall and, in many regions, identical.

Variants of polynucleotides according to the invention include, without being limited to, nucleotide sequences which are at least 95% identical after optimal alignment to the reference polynucleotide of SEQ ID N°39 to 76 encoding the reference Selected Interacting Domain (SID®) polypeptide, preferably at least 96%, 97%, 98% and most preferably at least 99% identical to the reference polynucleotide. Similarly, a variant of a SID® polypeptide of the invention consists of a polypeptide having at least 95% aminoacid identity with a polypeptide selected from the aminoacid sequences SEQ ID N°1 to 38, and preferably at least 96%, 97%, 98% and most preferably at least 99% aminoacid identity with one of SEQ ID N°1 to 38.

Identity refers to sequence identity between two peptides or between two nucleic acid molecules. Identity between sequences can be determined by comparing a position in each of the sequences which may be aligned for purposes of comparison. When a position in the compared sequences is occupied by the same base or amino acid, then the sequences are identical at that position. A degree of identity between nucleic acid sequences is a function of the number of identical nucleotides at positions shared by these sequences. A degree of identity between amino acid sequences is a function of the number of identical aminoacids at positions shared by these sequences. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for determining a comparison window may be conducted by the local homology algorithm of Smith and Waterman (1981), by the homology alignment algorithm of Needleman and Wunsch (1972), by the search for similarity method of Pearson and Lipman (1988), by computerized implementations of these algorithms (GAP, BESTFIT, FASTA, and TFASTA in the Wisconsin Genetics Solftware Package Release 7.0, Genetics Computer Group, 575, Science Dr. Madison, W1), or by inspection. The best alignment (i.e., resulting in the highest percentage of identity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g. A, T, C, G, U or I) occurs in both sequences to yield the number of matched positions, dividing the number of matched positions by the total number of positions in the window of comparison (i.e., the window size), and multiplying the result by 100 to yield the percentage of sequence identity.

Most preferably, the percentage of nucleic acid or aminoacid identity between two nucleic acid or aminoacid sequences is calculated using the BLAST software (Version 2.06 of September 1998) with the default parameters.

Nucleotide changes present in a variant polynucleotide may be silent, which means that they do not alter the aminoacid encoded by the reference polynucleotide.

However, nucleotide changes may also result in aminoacid substitutions, additions, deletions, fusions and truncations in the Selected Interacting Domain (SD®) polypeptide encoded by the reference sequence.

The substitutions, deletions or additions may involve one or more nucleotides. Alterations may produce conservative or non-conservative aminoacid substitutions, deletions or additions.

Most preferably, the variant of a Selected Interacting Domain (SID®) polypeptide encoded by a variant polynucleotide possesses at least the same affinity of binding to its protein or polypeptide counterpart, against which it has been initially selected as described above.

The affinity of a given SID® polypeptide of the invention for a polypeptide into which it specifically binds is defined as the affinity constant Ka, wherein $$Ka = \frac{[SID®/polypeptide\ complex]}{[free\ SID®][free\ polypeptide]}$$

with [free SID®], [free polypeptide] and [SID®/polypeptide complex] consist of the concentrations at equilibrium respectively of the free SID® polypeptide, of the free polypeptide onto which the SID® polypeptide specifically binds and of the complex formed between the SID® polypeptide and the polypeptide onto which said SID® polypeptide specifically binds.

Most preferably, the affinity of a SID® polypeptide of the invention or a variant thereof for its polypeptide counterpart (polypeptide partner) is assessed on a Biacore™ apparatus marketed by Amercham Pharmacia Biotech Company such as described by SZABO et al. (1995) and by Edwards and Leartherbarrow (1997).

As used herein, the expression <<at least the same affinity>> with reference to the affinity of binding between a SID® polypeptide of the invention to another polypeptide means that the Ka is identical or is of at least two-fold, preferably at least three-fold and most preferably at least five-fold greater than the Ka value of reference.

In another preferred embodiment, the variant of a Selected Interacting Domain (SID®) polypeptide which is encoded by a variant polynucleotide of the invention possesses a higher specificity of binding to its counterpart polypeptide or protein than the reference Selected Interacting Domain (SID®) polypeptide.

A variant of a Selected Interacting Domain (SID®) polypeptide according to the invention may be (1) one in which one or more, most preferably from one to three, of the aminoacid residues are substituted with a conserved or a non-conserved aminoacid residue and such substituted aminoacid residue may or may not be one encoded by the genetic code, or (2) one in which one or more of the aminoacid residues includes a substituent group.

In the case of an aminoacid substitution in the aminoacid sequence of a Selected Interacting Domain (SID®) polypeptide according to the invention, one or several-consecutive or non-consecutive—aminoacids are replaced by "equivalent" aminoacids. The expression "equivalent" aminoacid is used herein to designate any aminoacid that may be substituted for one of the aminoacids belonging to the native Selected Interacting Domain (SID®) polypeptide structure without decreasing the binding properties of the corresponding peptides to their counterpart polypeptide or protein, as regards the reference Selected Interacting Domain (SID®) polypeptide.

These equivalent aminoacids may be determined either by their structural homology with the initial aminoacids to be replaced, by the similarity of their net charge or of their hydrophobicity.

By an equivalent aminoacid according to the present invention is also meant the replacement of a residue in the L-form by a residue in the D-form or the replacement of a glutamic acid residue by a pyro-glutamic acid compound. The synthesis of peptides containing at least one residue in the D-form is, for example, described by KOCH (1977). A specific embodiment of a variant of a Selected Interacting Domain (SID®) polypeptide according to the invention includes, but is not limited to, a peptide molecule which is resistant to proteolysis, such as a peptide in which the —CONH— peptide bond is modified and replaced by a —CH$_2$NH— ) reduced bond, a (—NHCO—) retroinverso bond, a (—CH$_2$—O—) methylene-oxy bond, a (—CH$_2$—S—) thiomethylene bond, a (—CH$_2$CH$_2$—) carba bond, a (—CO—CH$_2$) hydroxyethylene bond, a (—N—N—) bond or also a —CH═CH bond.

As used herein, a variant of a SID® polypeptide of the invention also encompasses a polypeptide having an aminoacid sequence consisting of at least:

45 consecutive aminoacids of SEQ ID N°1;
30 consecutive aminoacids of SEQ ID N°2;
65 consecutive aminoacids of SEQ ID N°3;
30 consecutive aminoacids of SEQ ID N°4;
130 consecutive aminoacids of SEQ ID N°5;
25 consecutive aminoacids of SEQ ID N°6;
23 consecutive aminoacids of SEQ ID N°7.
48 consecutive aminoacids of SEQ ID N°8;
36 consecutive aminoacids of SEQ ID N°9;
25 consecutive aminoacids of SEQ ID N°10;
24 consecutive aminoacids of SEQ ID N°11;
37 consecutive aminoacids of SEQ ID N°12;
25 consecutive aminoacids of SEQ ID N°13;
30 consecutive aminoacids of SEQ ID N°14;
27 consecutive aminoacids of SEQ ID N°15;
69 consecutive aminoacids of SEQ ID N°16;
130 consecutive aminoacids of SEQ ID N°17;
33 consecutive aminoacids of SEQ ID N°18;
25 consecutive aminoacids of SEQ ID N°19;
40 consecutive aminoacids of SEQ ID N°20;
78 consecutive aminoacids of SEQ ID N°21;
39 consecutive aminoacids of SEQ ID N°22;
57 consecutive aminoacids of SEQ ID N°23;
26 consecutive aminoacids of SEQ ID N°24;
68 consecutive aminoacids of SEQ ID N°25;
34 consecutive aminoacids of SEQ ID N°26;
42 consecutive aminoacids of SEQ ID N°27;
48 consecutive aminoacids of SEQ ID N°28.
102 consecutive aminoacids of SEQ ID N°29:
49 consecutive aminoacids of SEQ ID N°30:
92 consecutive aminoacids of SEQ ID N°31;
49 consecutive aminoacids of SEQ ID N°30;
92 consecutive aminoacids of SEQ ID N°31;
71 consecutive aminoacids of SEQ ID N°32;
55 consecutive aminoacids of SEQ ID N°33;
69 consecutive aminoacids of SEQ ID N°34;

23 consecutive aminoacids of SEQ ID N°35;
33 consecutive aminoacids of SEQ ID N°36;
32 consecutive aminoacids of SEQ ID N°37; and
22 consecutive aminoacids of SEQ ID N°38.

Without wishing to be bound by any particular theory, the inventors believe that polypeptides having an aminoacid length of about 10% lesser than the aminoacid length of anyone of the SID® polypeptides of SEQ ID N°1 to 39 of the invention have a high probability to retain the binding properties to a given (bait) polypeptide of the parent SID® polypeptide.

The invention also pertains to a nucleic acid encoding a SID® polypeptide which is selected from the group consisting of the sequences SEQ ID N°39 to 76, and a sequence complementary thereto.

The invention is also directed to a nucleic acid encoding a variant of SID® polypeptide selected from the group consisting of the sequences SEQ ID N°39 to 76, in reference to the definition of the SID® polypeptide variants above.

For example, a nucleic acid encoding a polypeptide having an aminoacid sequence consisting of at least 45 consecutive aminoacids of SEQ ID N°1 comprise at least 135 (45×3) consecutive nucleotides of the polynucleotide of SEQ ID N°39.

The same definition also apply for nucleic acids encoding variants of the SID® polypeptides of SEQ ID N°2 to 38, which are part of the invention.

The invention further relates to a nucleic acid encoding a polypeptide having an aminoacid sequence comprising from 1 to 3 substitutions, additions or deletions of one aminoacid as regards a polypeptide selected from the group consisting of the aminoacid sequences SEQ ID N°1 to 38 or a sequence complementary thereto.

Another object of the invention consists of a polypeptide selected from the group consisting of the aminoacid sequences SEQ ID N°39 to 76 or a variant thereof.

Are encompassed in the family of variants of a SID® polypeptide of the invention those polypeptides having an aminoacid sequence comprising from 1 to 3 substitutions, additions or deletions of one aminoacid as regards a polypeptide selected from the group consisting of the aminoacid sequences SEQ ID N°1 to 38.

The invention is also directed to an antibody directed against a SID® polypeptide as defined above, or to a variant thereof.

The antibodies directed specifically against the Selected Interacting Domain (SID®) polypeptide or a variant thereof may be indifferently radioactively or non-radioactively labelled.

Monoclonal antibodies directed against a SID® polypeptide may be prepared from hybridomas according to the technique described by Kohler and Milstein in 1975. Polyclonal antibodies may be prepared by immunization of a mammal, especially a mouse or a rabbit, with the SID® polypeptide that is combined with an adjuvant of immunity, and then by purifying the specific antibodies contained in the serum of the immunized animal on a affinity chromatography column on which has previously been immobilized the polypeptide that has been used as the antigen.

Antibodies directed against a SID® polypeptide may also be produced by the trioma technique and by the human B-cell hybridoma technique (Kozbor et al., 1983).

Antibodies directed to a SID® polypeptide include chimeric single chain Fv antibody fragments (U.S. Pat. No. 4,946,778; Martineau et al., 1998), antibody fragments obtained through phage display libraries (Ridder et al., 1995) and humanized antibodies (Reinmann et al., 1997; Leger et al., 1997). Also, transgenic mice, or other organisms such as other mammals, may be used to express antibodies, including for example, humanized antibodies directed against a SID® polypeptide of the invention, or a variant thereof.

Vectors of the Invention

The nucleic acids coding for a Selected Interacting Domain (SID®) polypeptide or a variant thereof, which are defined in the section above, can be inserted into an appropriate expression vector, i.e., a vector which contains the necessary elements for the transcription and translation of the inserted protein-coding sequence. Such transcription elements include a regulatory region and a promoter as defined previously. Thus, the nucleic acid encoding a marker compound of the invention is operably linked with a promoter in a expression vector, wherein said expression vector may include a replication origin.

The necessary transcriptional and translation of signals is most preferably provided by the recombinant expression vector.

Structure of the Vectors Encompassed by the Invention

A wide variety of host/expression vector combinations may be employed in expressing the nucleic acids of this invention. Useful expression vectors, for example, may consist of segments of chromosomal, non-chromosomal and synthetic DNA sequences. Suitable vectors include derivatives of SV40 and known bacterial plasmids, e.g., *Escherichia coli* plasmids col EI, pCR1, pBR322, pMaI-C2, pET, pGEX (Smith et al., 1988), pMB9 and their derivatives, plasmids such as RP4; phage DNAs, e.g., the numerous derivatives of phage I, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression system, both non-fusion transfer vectors, such as but not limited to pVL941 (BamHI cloning site; Summers), pVL1393 (BamHI, SmaI, XbaI, EcoRI, NotI, XmaIII, BglII, and PstI cloning site; Invitrogen), pVL1392 (BglII, PstI, NotI, XmaIII, EcoRI, XbaI, SmaI, and BamHI cloning site; Summers and Invitrogen), and pBlueBacIII (BamHI, BglII, PstI, NcoI, and HindIII cloning site, with blue/white recombinant screening possible; Invitrogen), and fusion transfer vectors, such as but not limited to pAc700(BamHI and KpnI cloning site, in which the BamH1 recognition site begins with the initiation codon; Summers), pAc701and pAc702(same as pAc700, with different reading frames), pAc360 (BamHI cloning site 36 base pairs downstream of a polyhedrin initiation codon; Invitrogen(195)), and pBlueBacHisA, B, C (three different reading frames, with BamHI, BglII, PstI, NcoI, and HindIII cloning site, an N-terminal peptide for ProBond purification, and blue/white recombinant screening of plaques; Invitrogen (220) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; Kaufman, 1991). Alternatively, a glutamine synthetase/ methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible methallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and b-gal selection), pMJ601 (SalI, SmaI, AflI, NarI, BspMII, BamHI, ApaI, NheI, SacII, KpnI, and HindIII cloning site; TK- and b-gal selection), and pTKgptF1S (EcoRI, PstI, SalI, AccI, HindII, SbaI, BamHI, and Hpa cloning site, TK or XPRT selection).

Yeast expression systems can also be used according to the invention to express a Selected Interacting Domain (SID®) polypeptide or a variant thereof and also a marker compound as defined herein. For example, the non-fusion pYES2 vector (XbaI, SphI, ShoI, NotI, GstXI, EcorI, BstXI, BamHI, SacI, KpnI, and HindIII cloning sit; Invitrogen) or the fusion pYESHisA, B, C (XbaI, SphI, ShoI, NotI, BstXI, EcoRI, BamHI, SacI, KpnI, and HindIII cloning site, N-terminal peptide purified with ProBond resin and cleaved with enterokinase; Invitrogen), to mention just two, can be employed according to the invention.

Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992; Wu and Wu, 1988; Canadian Patent Application No. 2,012,311, filed Mar. 15, 1990).

A cell has been "transfected" by exogenous or heterologous DNA when such DNA has been introduced inside the cell. A cell has been "transformed" by exogenous or heterologous DNA when the transfected DNA effects a phenotypic change.

For introducing a vector in a cell host, explicit reference is made to research carried out by the group of E. Wagner, relating to gene delivery by means of plasmid-polylysine complexes (Curiel et al., 1991; and Curiel et al., 1992). The plasmid-polylysine complex investigated upon exposition to certain cell lines showed at least some expression of the gene. Further, it was found that the expression efficiency increased considerably due to the binding of transferrin to the plasmid-polylysine complex. Transferrin gives rise to close cell-complex contact with cells comprising transferrin receptors; it binds the entire complex to the transferrin receptor of cells. Subsequently, at least part of the entire complex was found to be incorporated in the cells investigated.

Several different approaches have been developed for gene transfer. These include the use of viral based vectors (e.g., retroviruses, adenoviruses, and adeno-associated viruses) (Drumm, M. L. et al., Rosenfeld, M. A. et al., 1992; and Muzyczka, 1992), charge associating the DNA with an asialorosomucoid/poly L-lysine complex (Wilson, J. M. et al. 1992), charge associating the DNA with cationic liposomes (Brigham, K. L. et al., 1993) and the use of cationic liposomes in association with a poly-L-lysine antibody complex (Trubetskoy, V. S. et al., 1993).

Compositions Comprising Vectors of the Invention.

Although non-viral based transfection systems have not exhibited the efficiency of viral vectors, they have received significant attention, in both in vitro and in vivo research, because of their theoretical safety when compared to viral vectors. Synthetic cationic molecules, have been reported which reportedly "coat" the nucleic acid through the interaction of the cationic sites on the transfection agent and the anionic sites on the nucleic acid. The positively charged coating reportedly interacts with the negatively charged cell membrane to facilitate the passage of the nucleic acid through the cell membrane by non-specific endocytosis. (Schofield, 1995) These compounds have, however, exhibited considerable sensitivity to natural serum inhibition, which has probably limited their efficiency in vivo as gene transfection agents. (Behr 1994)

A number of attempts have been made to improve the efficiency of lipid-like cationic transfection agents, some involving the use of polycationic molecules. For example, several transfection agents have been developed that contain the polycationic compound spermine covalently attached to a lipid carrier. (Behr, 1994), discloses a lipopolyamine and shows it to be more efficient at transfecting cells than single charge molecules (albeit still less efficient than viral vectors). The agent reported by Behr was, however, toxic, and caused cell death.

A few such lipid delivery systems for transporting DNA, proteins, and other chemical materials across membrane boundaries have been synthesized by research groups and business entities. Most of the synthesis schemes are relatively complex and generate lipid based delivery systems having only limited transfection abilities. A need exists in the field of gene therapy for cationic lipid species that have a high biopolymer transport efficiency. It has been known for some time that a very limited number of certain quaternary ammonium derivatized (cationic) liposomes spontaneously associate with DNA, fuse with cell membranes, and deliver the DNA into the cytoplasm (as noted above, these species have been termed "cytofectins"). LIPOFECTIN ™. represents a first generation of cationic liposome formulation development. LIPOFECTIN ™ is composed of a 1:1 formulation of the quaternary ammonium containing compound DOTMA and dioleoylphosphatidylethanolamine sonicated into small unilamellar vesicles in water. Problems associated with LIPOCFECTIN ™ include nonmetabolizable ether bonds, inhibition of protein kinase C activity, and direct cytotoxicity. In response to these problems, a number of other related compounds have been developed. The monoammonium compounds of the subject invention improve upon the capabilities of existing cationic liposomes and serve as a very efficient delivery system for biologically active chemicals.

Most Preferred Vectors of the Invention.

Most preferred recombinant vectors according to the invention include pASΔΔ(FIG. 2), pACTIIst (FIG. 3), pT18 (FIG. 4), pUT18C (FIG. 5), pT25 (FIG. 6), pKT25 (FIG. 7), pB5 (FIG. 12) and pP6 (FIG. 13) containing inserted therein a nucleic acid encoding a Selected Interacting Domain (SID®) polypeptide or a variant thereof as defined above.

The present invention is also directed to a vector usable in a two-hybrid method which consists of the vector pP6 which is shown in FIG. 13. As disclosed in example 1, the vector pP6 has been successfully used for preparing a collection of recombinant plasmids consisting of a genomic DNA library from the pathogenic strain H77 of the hepatitis C virus.

The invention also pertains to a vector usable in two-hybrid method which consists of the vector pB5. As disclosed in example 1, the vector pB5 has been successfully used in a yeast two hybrid method as a bait plasmid.

Recombinant Cell Hosts

In one embodiment, a Selected Interacting Domain (SID®) polypeptide of the invention or a variant thereof is recombinantly produced in a desired host cell which has been transfected or transformed with a nucleic acid encoding said Selected Interacting Domain (SID®) polypeptide or with a recombinant vector as defined above within which a nucleic acid encoding a Selected Interacting Domain (SID®) polypeptide of the invention is inserted.

Recombinant cell hosts are another aspect of the present invention.

Such cell hosts generally comprise at least one copy of a nucleic acid encoding a Selected Interacting Domain (SID®) polypeptide of the invention or a variant thereof Preferred cells for expression purposes will be selected in function of the objective which is sought. For example, in the embodiment wherein the production of a Selected Interacting Domain (SID®) polypeptide according to the invention in large quantities is sought, the nature of the host cell used for its production is relatively indifferent, provided that large amounts of Selected Interacting Domain (SID®) polypeptides of the invention are produced and that optional further purification steps may be carried out easily.

However, in the embodiment wherein the Selected Interacting Domain (SID®) polypeptide is recombinantly produced within a host organism for the purpose of interfering with a specific protein-protein interaction, then the host organism is selected among the host organisms which are suspected to produce naturally said polypeptide of interest.

Consequently, mammalian and typically human cells, as well as bacterial, yeast, fungal, insect, nematode and plant cells are cell hosts encompassed by the invention and which may be transfected either by a nucleic acid or a recombinant vector as defined above.

Examples of suitable recombinant host cells include VERO cells, HELA cells (e.g. ATCC N°CCL2), CHO cell-lines (e.g. ATCC N°CCL61) COS cells (e.g. COS-7 cells; COS cell referred to ATCC N°CRL1650), W138, BHK, HepG2, 3T3 (e.g. ATCC N°CRL6361), A549, PC12, K562 cells, 293 cells, Sf9 cells (e.g. ATCC N°CRL1711) and Cv1 cells (e.g. ATCC N°CCL70).

Other suitable host cells are usable according to the invention include prokaryotic host cells strains of *Escherichia coli* (e.g. strain DH5-α), of *Bacillus subtilis*, of *Salmonella typhimurium*, or strains of genera such as *Pseudomonas, Streptomyces* and *Staphylococcus*.

Further suitable host cells usable according to the invention include yeast cells such as those of *Saccharomyces*, typically *Saccharomyces cerevisiae*.

The invention also relates to a method for producing a SID® polypeptide as defined above, wherein said method comprises the steps of:

a) cultivating a cell host which has been transformed with a SID® nucleic acid of the invention or with a vector containing a SID® nucleic acid in an appropriate culture medium;

b) recovering the SID® recombinant polypeptide from the culture supernatant or from the cell lysate.

The SID® polypeptides or variant thereof thus recombinantly obtained may be purified, for example by high performance liquid chromatography, such as reverse phase and/or cationic exchange HPLC, as described by ROUGEOT et al. (1994). The reason to prefer this kind of peptide or protein purification is the lack of by-products found in the elution samples which renders the resultant purified protein more suitable for a therapeutic use.

Two-hybrid Methods of the Invention a) Yeast Two-hybrid Methods

The invention also pertains to a yeast two-hybrid method for selecting a recombinant cell clone containing a vector comprising a nucleic acid insert encoding a prey polypeptide which binds with a SID® polypeptide of SEQ ID N°1 to 38 or a variant thereof, wherein said method comprises the steps of:

a) mating at least one first recombinant yeast cell clone of a collection of recombinant yeast cell clones transformed with a plasmid containing the prey polynucleotide to be assayed with a second aploïd recombinant *Saccharomyces cerevisiae* cell clone transformed with a plasmid containing a bait polynucleotide encoding a SID® polypeptide of the invention or a variant thereof;

b) cultivating diploid cells obtained in step a) on a selective medium; and c) selecting recombinant cell clones which grow on said selective medium.

The yeast two-hybrid method above may further comprise the step of:

d) characterizing the prey polynucleotide contained in each recombinant cell clone selected in step c).

Most preferably, such a yeast two-hybrid method may be performed by the one skilled in the art as it is disclosed in example 2 hereafter.

According to the yeast two-hybrid method above, a SID® polypeptide of the invention or a variant thereof is used as a bait polypeptide.

In a preferred embodiment of the yeast two-hybrid method described above, the prey polynucleotide is a DNA fragment from the genome of a pathogenic strain of the hepatitis C virus (HCV) ranging from about 150 to about 600 nucleotides in length and which is inserted in a vector which is contained in one recombinant clone of a collection of recombinant cell clones.

b) Bacterial Two-hybrid Method

A bacterial two-hybrid method of the invention may be performed by the one skilled in the art according to the teachings of KARIMOVA et al. (1998).

The first step of selecting a collection of nucleic acids encoding polypeptides which binds specifically to the bait polypeptide may also be carried out through a bacterial two-hybrid system.

According to such bacterial two-hybrid system, bacterial cell clones, preferably *Escherichia coli* cells, are transformed with a plasmid containing a bait polynucleotide encoding a bait polypeptide.

Then, plasmids containing a DNA insert are provided by rescuing the plasmids obtained from the collection of yeast clones containing the genomic DNA or cDNA library which are described in the previous section entitled "Yeast two-hybrid system". For example, the plasmid rescue may be carried out according to the following steps:

(i) extracting plasmid DNA contained in the collection of yeast clones obtained as disclosed in the previous section, by using a conventional DNA extraction buffer and a phenol:chloroform:isoamyl alcohol (25:24:1) before centrifuging;

(ii) transferring a desired volume of the supernatant obtained at the end of step (i) to a sterile Eppendorf tube and add a precipitation buffer (ethanol/NH$_4$Ac) before centrifuging and resuspending the pellet after washing in ethanol;

(iii) transforming *Escherichia coli* cells (e.g. *Escherichia coli* cells of strain NC 1066) which have been rendered electrocompetent with a desired volume (e.g. 1 µl) of the yeast plasmid DNA extract obtained at step (ii) by electroporation;

(iv) collecting the transformed *Escherichia coli* cells.

Alternatively, a collection of *Escherichia coli* cell clones containing a collection of HCV genomic DNA inserts may be obtained by constructing the DNA library directly in the bacterial cell, such as disclosed in Flajolet et al. (2000).

Then, the bacterial recombinant cells which have been transformed both with a plasmid containing a bait polynucleotide encoding a bait polypeptide and a plasmid containing a prey polynucleotide encoding a prey polynucleotide is cultivated on a selective medium.

Then, recombinant cell clones capable of growing on said selective medium are selected and the DNA inserts of the plasmids containing therein are sequenced.

By bacterial two-hybrid system is generally intended a method that usually makes use of at least one reporter gene, the transcription of which is activated when a prey polypeptide and a bait polypeptide produced by the recombinant cell due to the triggering of the transcription of said at least one reporter gene when both the specific domain contained in one prey polypeptide and the complementary domain contained in the bait polypeptide are binding one to the other.

The invention further pertains to a bacterial two-hybrid method for identifying a recombinant cell clone containing a prey polynucleotide encoding a prey polypeptide which binds with a SID® polypeptide of SEQ ID N°1 to 38 or a variant thereof, wherein said method comprises the steps of:

a) transforming bacterial cell clones with a plasmid containing a SID® polynucleotide encoding a SID® polypeptide of the invention or a variant thereof;

b) rescuing prey plasmids containing prey polynucleotides wherein each prey polynucleotide is a DNA fragment from the genome of a desired organism and wherein each prey plasmid is contained in one recombinant yeast cell clone of a collection of recombinant yeast cell clones;

c) transforming the recombinant bacterial cell clones obtained in step a) with the plasmids rescued in step b);

d) cultivating bacterial recombinant cells obtained in step c) on a selective medium; and e) selecting recombinant cell clones which grow on said selective medium.

The bacterial two-hybrid system described above may further comprise the step of f) characterizing the prey polynucleotide contained in each recombinant cell clone selected at step e).

In one preferred embodiment of the yeast or bacterial two-hybrid methods described above, the prey polypeptide is a human polypeptide expressed by a mammal which is infected by the Hepatitis C virus, like human and monkeys, typically chimpanzees.

Generally, the yeast two-hybrid method or the bacterial two-hybrid method as disclosed herein may be performed with prey polypeptides of any origin, either of viral, fungal, bacterial or mammal origin, i.e. either of prokaryotic or eukaryotic origin.

In a second preferred embodiment of the two-hybrid methods above, the prey polypeptide is an HCV polypeptide.

Most preferably, the prey polypeptide is encoded by a strain of the hepatitis C virus which is pathogenic for human, such as strain H77.

Sets of Nucleic Acids and Sets of Polypeptides of the Invention

In yet another aspect, the present invention relates to a set of two nucleic acids consisting of:

i) a first nucleic acid encoding a SID® polypeptide of SEQ ID N°1 to 39 of the invention or a variant thereof; and ii) a second nucleic acid encoding a prey polypeptide which binds specifically with a SID® polypeptide defined in i).

In still a further aspect, the invention is also directed to a set of two polypeptides consisting of:

i) a first polypeptide consisting of a SID® polypeptide of SEQ ID N°1 to 39 of the invention or a variant thereof; and ii) a second polypeptide which binds specifically with the first polypeptide.

The invention further relates to a complex formed between i) a first polypeptide consisting of a SID® polypeptide of SEQ ID N°1 to N°38 of the invention; and ii) a second polypeptide which binds specifically with the first polypeptide.

The invention also relates to a protein-protein interaction wherein the two interacting proteins consist of a set of two polypeptides as defined above.

In a preferred embodiment, the invention relates to the protein-protein interactions wherein the sets of two polypeptides consist of a SID®polypeptide of SEQ ID N°1 to 38 and an HCV polypeptide.

When several reiterations of the two-hybrid method are performed and thus common SID® polypeptide and prey polypeptides are selected, a map of all the interactions between these polypeptides may be designed, that take into account of the known and/or suspected biological function of each of the interacting polypeptides.

Table 1 illustrates protein-protein interaction between the SID® polypeptides of SEQ ID N°1 to 38 and polypeptides of SEQ ID N°77 to 113 which are encoded by the genome of strain H77 of the hepatitis C virus which is pathogenic for a mammal, like human or chimpanzee.

Thus, the data presented in table 1 disclose particular sets of nucleic acids as well as particular sets of polypeptides which are encompassed by the present invention.

For example, table 1 discloses that the nucleic acid of SEQ ID N°39 encodes the SID® polypeptide of SEQ ID N°1 which contains exclusively (100%) an aminoacid sequence from the Core protein of HCV strain H77.

The nucleic acid of SEQ ID N°39 starts at the nucleotide in position 446 and ends at the nucleotide in position 600 of the HCV genome which is described by YANAGI et al. (1997).

Table 1 also discloses that the SID® polypeptide of SEQ ID N°1 is part of a set of polypeptides of the invention, wherein the second polypeptide of said set of polypeptides consists of the polypeptide of SEQ ID N°77 which is encoded by the nucleic acid sequence of SEQ ID N°114, which nucleic acid sequence has 87% of its sequence which is derived from the region of the H77 strain HCV DNA encoding the Core protein.

Thus, a particular set of polypeptides according to the invention consists of:

i) the polypeptide of SEQ ID N°1; and ii) the polypeptide of SEQ ID N°77.

The same reasoning apply for every set of polypeptides disclosed in table 1, which are expressly part of the present invention.

Similarly, a particular set of nucleic acids according to the invention consists of.

(i) the nucleic acid of SEQ ID N°39; and (ii) the nucleic acid of SEQ ID N°114.

The same reasoning apply for every set of nucleic acids disclosed in table 1, which are expressly part of the present invention.

Thus, particular sets of two polypeptides of the invention are respectively SEQ ID N°77/SEQ ID N°1; SEQ ID N°78/SEQ ID N°2; SEQ ID N°78/SEQ ID N°3; SEQ ID N°79/SEQ ID N°4; SEQ ID N°80/SEQ ID N°5; SEQ ID N°81/SEQ ID N°6; SEQ ID N°82/SEQ ID N°7; SEQ ID N°83/SEQ ID N°8; SEQ ID N°84/SEQ ID N°9; SEQ ID N°85/SEQ ID N°10; SEQ ID N°86/SEQ ID N°11; SEQ ID N°87/SEQ ID N°12; SEQ ID N°88/SEQ ID N°13; SEQ ID N°89/SEQ ID N°14; SEQ ID N°90/SEQ ID N°15; SEQ ID N°91/SEQ ID N°16; SEQ ID N°92/SEQ ID N°17; SEQ ID N°93/SEQ ID N°18; SEQ ID N°94/SEQ ID N°19; SEQ ID N°95/SEQ ID N°20; SEQ ID N°96/SEQ ID N°21; SEQ ID N°97/SEQ ID N°22; SEQ ID N°98/SEQ ID N°23; SEQ ID N°99/SEQ ID N°24; SEQ ID N°100/SEQ ID N°25. SEQ ID N°101/SEQ ID N°26. SEQ ID N°102/SEQ ID N°27; SEQ ID N°103/SEQ ID N°28. SEQ ID N°104/SEQ ID N°29; SEQ ID N°105/SEQ ID N°30; SEQ ID N°106/SEQ ID N°31; SEQ ID N°107/SEQ ID N°32; SEQ ID N°108/SEQ ID N°33; SEQ ID N°109/SEQ ID N°34; SEQ ID N°110/SEQ ID N°35; SEQ ID N°111/SEQ ID N°36; SEQ ID N°112/SEQ ID N°37; and SEQ ID N°113/SEQ ID N°38.

Similarly, particular sets of two nucleic acids according to the invention are respectively: SEQ ID N°114/SEQ ID N°39; SEQ ID N°115/SEQ ID N°40; SEQ ID N°115/SEQ ID N°41; SEQ ID N°116/SEQ ID N°42; SEQ ID N°117/SEQ ID N°43; SEQ ID N°118/SEQ ID N°44; SEQ ID N°119/SEQ ID N°45; SEQ ID N°120/SEQ ID N°46; SEQ ID N°121/SEQ ID N°47; SEQ ID N°122/SEQ ID N°48; SEQ ID N°123/SEQ ID N°49; SEQ ID N°124/SEQ ID N°50; SEQ ID N°125/SEQ ID N°51; SEQ ID N°126/SEQ ID N°52; SEQ ID N°127/SEQ ID N°53; SEQ ID N°128/SEQ ID N°54; SEQ ID N°129/SEQ ID N°55; SEQ ID N°130/SEQ ID N°56; SEQ ID N°131/SEQ ID N°57; SEQ ID N°132/SEQ ID N°58; SEQ ID N°133/SEQ ID N°59; SEQ ID N°134/SEQ ID N°60; SEQ ID N°135/SEQ ID N°61; SEQ ID N°136/SEQ ID N°62; SEQ ID N°137/SEQ ID N°63; SEQ ID N°138/SEQ ID N°64; SEQ ID N°139/SEQ ID N°65; SEQ ID N°140/SEQ ID N°66; SEQ ID N°141/SEQ ID N°67; SEQ ID N°142/SEQ ID N°68; SEQ ID N°143/SEQ ID N°69; SEQ ID N°144/SEQ ID N°70. SEQ ID N°145/SEQ ID N°71; SEQ ID N°146/SEQ ID N°72. SEQ ID N°147/SEQ ID N°73; SEQ ID N°148/SEQ ID N°74; SEQ ID N°149/SEQ ID N°75 and SEQ ID N°150/SEQ ID N°76.

The protein-protein interactions disclosed in table 1 allows the design of a map of interactions between various polypeptides encoded by the genome of the H77 strain of HCV.

In such a Protein Interaction Map (PIM®) wherein each SID® polypeptide is linked to the bait polypeptide onto which it specifically binds, for example by an arrow.

Such a Protein Interaction Map (PIM®) may help the one skilled in the art to decipher a whole metabolical and/or physiological pathway that is functionally active within a pathogenic strain of HCV. Protein Interaction Map and computable version of PIM® are part of the present invention.

Therefore, in still another aspect, the present invention is directed to a computable readable medium (such as floppy disk, CD-ROM and all electronic or magnetic format which can be read by a computer) having stored thereon protein-protein interactions according to the invention, preferably stored in a form of a Protein Interaction MAP, as shown, for example, in FROMONT-RACINE et al. (1997).

In a preferred embodiment, the invention comprises a computable readable medium as defined above, wherein the protein-protein interactions stored thereon are linked to annotated data base, for example through Internet.

In another preferred embodiment, the invention comprises a data bank containing the protein-protein interactions stored thereon, said data bank being available on a world-wide web site.

Methods for Selecting Inhibitors of Protein-Protein Interactions of the Invention The transformed host cells as described above can also be used as models so as to study the interactions between a SID® polypeptide of the invention and its binding partner polypeptide, or between a SID® polypeptide of the invention and chemical or protein compounds which inhibit the binding between said SID® polypeptide and its binding partner polypeptide.

Example of a SID® polypeptide and its binding partner polypeptides are typically the sets of polypeptides of the invention which are described above.

In particular, the transformed host cells of the invention may be used for the selection of molecules which interact with a SID® polypeptide as described herein, as cofactor or as inhibitor, in particular a competitive inhibitor, or alternatively having an agonist or antagonist activity on the protein-protein interaction wherein said SID® polypeptide is involved. Preferably, the said transformed host cells will be used as a model allowing, in particular, the selection of products which make it possible to prevent and/or to treat pathologies induced by the hepatitis C virus.

Consequently, the invention also consists of a method for selecting a molecule which inhibits the protein-protein interaction of a set of two polypeptides as defined above, wherein said method comprises the steps of:

a) cultivating a recombinant host cell containing a reporter gene the expression of which is toxic for said recombinant host cell, said host cell being transformed with two vectors wherein:

i) the first vector contains a nucleic acid comprising a polynucleotide encoding a first hybrid polypeptide containing one of said two-polypeptides and a DNA binding domain;

ii) the second vector contains a nucleic acid comprising a polynucleotide encoding a second hybrid polypeptide containing the second of said two polypeptides and an activating domain capable of activating said toxic reporter gene when the first and the second hybrid polypeptides are interacting;

on a selective medium containing the molecule to be ested and allowing the growth of said recombinant host cell when the toxic reporter gene is not activated; and b) selecting the molecule which inhibits the growth of the recombinant host cell defined in step a).

The invention is also directed to a method for selecting a molecule which inhibits the protein-protein interaction of a set of two polypeptides as defined above, wherein said method comprises the steps of:

a) cultivating a recombinant host cell containing a reporter gene the expression of which is toxic for said recombinant host cell, said host cell being transformed with two vectors wherein:

i) the first vector contains a nucleic acid comprising a polynucleotide encoding a first hybrid polypeptide containing one of said two polypeptides and the first domain of an enzyme;

ii) the second vector contains a nucleic acid comprising a polynucleotide encoding a second hybrid polypeptide containing the second of said two polypeptides and the second part of said enzyme capable of activating said toxic reporter gene when the first and the second hybrid polypeptides are interacting, said interaction recovering the catalytic activity of the enzyme;

on a selective medium containing the molecule to be tested and allowing the growth of said recombinant host cell when the toxic gene is not activated; and b) selecting the molecule which inhibits the growth of the recombinant host cell defined in step a).

In a preferred embodiment, said toxic reporter gene that can be used for negative selection is URA3, CYH1 or CYH2 gene.

For example, a method for the screening of a molecule which inhibits the interaction between a SID® polypeptide of the invention with its binding protein counterpart may comprise the following steps:

transform a permeabilized yeast cell with two vectors, respectively a first vector containing a SID® nucleic acid of the invention and a second vector containing a prey nucleic acid as defined in the present specification;

plate on top agar the transformed permeabilized yeast cells above on square boxes;

apply by spotting the candidate inhibitor molecules to test on top agar as soon as it is solidified;

incubates, for example, overnight at 30° C., and select the inhibitor compounds that allow the growth of the transformed yeast cells.

The invention also provides for a kit for the screening of a molecule which inhibits the protein-protein interaction of a set of two polypeptides as defined above, wherein said kit comprises a recombinant host cell containing a reporter gene the expression of which is toxic for said recombinant host cell, said host cell being transformed with two vectors wherein:

i) the first vector contains a nucleic acid comprising a polynucleotide encoding a first hybrid polypeptide containing one of said two polypeptides and a DNA binding domain;

ii) the second vector contains a nucleic acid comprising a polynucleotide encoding a second hybrid polypeptide containing the second of said two polypeptides and an activating domain capable of activating said toxic reporter gene when the first and the second hybrid polypeptides are interacting.

Another object of the invention consists of a kit for the screening of a molecule which inhibits the protein-protein interaction of a set of two polypeptides as defined above, wherein said kit comprises a recombinant host cell containing a reporter gene the expression of which is toxic for said recombinant host cell, said host cell being transformed with two plasmids wherein:

i) the first vector contains a nucleic acid comprising a polynucleotide encoding a first hybrid polypeptide containing one of said two polypeptides and the first domain of a protein;

ii) the second vector contains a nucleic acid comprising a polynucleotide encoding a second hybrid polypeptide containing the second of said two polypeptides and the second part of said protein capable of activating said toxic reporter gene when the first and the second hybrid polypeptides are interacting, said interaction recovering the activity of the protein. In the selection methods above, the transcription or activating domain and the DNA-binding domain may be derived from Gal4 and LexA respectively.

In the embodiment wherein the first domain is a first part of an enzyme and a complementary domain is a second part of the same enzyme, and wherein the proximity of the two parts of the enzyme restores the enzyme activity and activates a reporter gene, the two parts of the enzymes are most preferably the T25 and T18 polypeptides that form the catalytic domain of the *Bordetella pertussis* adenylate cyclase.

As an illustrative embodiment, the reporter gene is chosen among the group consisting of a nutritional gene or also a gene the expression of which is visualised by colorimetry such as His3, LacZ or both LacZ and His3.

Market Compounds of the Invention

The Selected Interacting Domain (SID®) polypeptides of SEQ ID N°1 to 38 of the invention and variants thereof defined in the present specification, and which bind specifically to a polypeptide of interest (e.g. a bait polypeptide), are useful as reagents for detecting, labelling, targeting or purifying specifically a polypeptide of interest, typically a polypeptide encoded by HCV, within a sample, since the SID® polypeptides possess properties that have never been reached using conventional detection compounds, such as those of an antibody or an antibody fragment.

Firstly, the SID® polypeptides of the invention possess a high specificity of binding to the polypeptide of interest, since a SID® polypeptide consists of a portion of a larger polypeptide which binds in a highly specific manner to the polypeptide of interest in the natural environment within the eukaryotic cell infected by the Hepatitis C virus.

Secondly, the SID® polypeptide generally has a low molecular weight, generally from 3 kDa, and are thus easy to produce, on the one hand, and, on the other hand, can be easily introduced within a cell when the detection of the localisation or of the expression of the polypeptide of interest is sought. Moreover, the small size of a SID® polypeptide allows its passage through inner cell barriers such as the nucleus membrane, or the membranes surrounding the different cell organites.

Thus, a first object of the invention consists of a marker compound wherein said compound comprises:

a) a Selected Interacting Domain (SID®) polypeptide of the invention or a variant thereof that binds specifically to the polypeptide of interest; and b) a detectable molecule bound thereto.

Such a marker compound is primarily useful for detecting, labelling or targeting a polypeptide of interest, for example a polypeptide of interest contained in a sample.

A detectable molecule according to the invention comprises, or alternatively consists of, any molecule which produces or can be induced to produce a signal. The detectable molecule can be a member of the signal producing system that includes the signal producing means.

The detectable molecule may be isotopic or non-isotopic. By way of example and not limitation, the detectable molecule can be part of a catalytic reaction system such as enzymes, enzyme fragments, enzyme substrates, enzyme inhibitors, co-enzymes, or catalysts. Part of a chromogen system such as fluorophores, dyes, chemiluminescers, luminescers, or sensitizers. A dispersible particle that can be non-magnetic or magnetic, a solid support, a liposome, a ligand, a receptor, a hapten radioactive isotope, and soforth.

It must be generally understood that the whole embodiments disclosed in the present specification involving a Selected Interacting Domain (SID®) polypeptide is straightfully applied also to any variant thereof.

Fluorescent Detectable Molecules

In one aspect of the marker compound according to the invention, the detectable molecule consists of a fluorescent molecule. Fluorescent moieties which are frequently used as labels are for example those described by Ichinose et al. (1991). Other fluorescent detectable molecules are fluorescing isothiocyanate (FITC) such as described by Shattil et al. (1987) or by Goding et al. (1986). The fluorescent detectable molecule may also comprise a phycoerythrin as taught by Goding et al. (1986), and Shattil et al. (1985). Other examples of fluorescent detectable molecules suitable for use as labels of a marker compound according to the invention are rhodamine isothiocyanate, dansyl chloride and XRITC.

Another fluorescent detectable molecule consists of the green fluorescent protein (GFP) of the jelly fish *Aequorea victoria*, and their numerous fluorescent protein derivatives.

The one skilled in the art may advantageously refer to the articles of CHALFIE et al. (1994) and of HEIM et al. (1994) which discloses the uses of GFP for the study of gene expression and protein localisation. The one skilled in the art may also refer to the article of Rizzuto et al. (1995), which discusses the use of wild-type GFP as a tool for visualising subcellular organelles in cells, to the article of KAETHER and GERDES (1995), which reports the visualisation of protein transport along the secretary passway using wild-type GFP, the article of HU and CHENG (1995), which relates to the expression of GFP in plant cells and also to the article of Davis et al. (1995) which discloses the GFP expression in *drosophilia* embryos. For the use of several fluorescent variants of GFP, the one skilled in the art may refer to the article of Delagrave et al. (1995), as well as to the article of Heim et al. (1995). DNA encoding GFP is available commercially, for example from Clontech in Palo Alto, Calif., USA. The one skilled in the art may use also humanized GFP genes such as those described in the U.S. Pat. No. 6,020,192 and also the GFP protein disclosed in the U.S. Pat. No. 5,941,084.

Another fluorescent protein that may be used in a marker compound according to the invention consists of the yellow fluorescent protein (YFP).

A further suitable luminescent protein consists of the luciferase protein.

Detectable Molecules Exhibiting a Catalytic Activity

In another embodiment of a detectable molecule included in a marker compound according to the invention, said detectable molecule is endowed with a catalytic activity and may thus consists of enzymes and catalytically active enzyme fragments. Some enzymatic labels are described in U.S. Pat. No. 3,654,090. Such enzymes may be for example horse radish peroxydase (HRP), alkaline phosphatase or glutathione peroxydase which are well known from the one skilled in the art.

Enzymes, enzyme fragments, enzyme inhibitors, enzyme substrates, and other components of enzyme reaction systems can be used as detectable molecules. Where any of these components is used as a detectable molecule, a chemical reaction involving one of the components is part of the signal producing system.

Coupled catalysts can also involve an enzyme with a non-enzymatic catalyst. The enzyme can produce a reactant, which undergoes a reaction catalysed by the non-enzymatic catalyst or the non-enzymatic catalyst may produce a substrate (including co-enzymes) for the enzyme. The one skilled in the art may advantageously refer to the U.S. Pat. No. 4,160,645 which disclose a white variety of non enzymatic catalysts, which may be employed, the appropriate portions of which are incorporated therein by reference.

The enzyme or co-enzyme employed provides the desired amplification by producing a product, which absorbs light, e.g., a tye, or emits lights upon irradiation, e.g., a fluorescer. Alternatively, the catalytic reaction can lead to direct light emission, e.g., chemiluminescence. A large number of enzymes and co-enzymes for providing such products are described in the U.S. Pat. No. 4,275,149, columns 19 to 23 and U.S. Pat. No. 4,318,980, columns 10 to 14 which disclosures are incorporated herein by reference.

A number of enzyme combinations are set forth in U.S. Pat. No. 4,275,149, columns 23 to 28 which disclosures are incorporated herein by reference.

When a single enzyme is used as the detectable molecule, or alternatively as comprised in the detectable molecule, such enzymes may find use are hydrolases, transferases, lyases, isomerases, ligases or synthetases and oxydoreductases.

Alternatively, luciferases may be used such as firefly luciferase and bacterial luciferase.

Primarily, the enzymes of choice, based on the I.U.B. classification are: (i) class 1. Oxydoreductases and (ii) class 3. Hydrolases. Most preferred oxydoreductases are (i) dehydrogenases of class 1.1, more particularly 1.1.1, 1.1.3. and 1.1.99 and (ii) peroxydases in class 1.11. of the hydrolases, particularly class 3.1., more particularly 3.1.3 and class 3.2, more particularly 3.2.1. are preferred.

Illustrative dehydrogenases include malate dehydrogenase, glucose-6-phosphate dehydrogenase and lactate dehydrogenase. Of the oxydases, glucose oxydases is exemplary. Of the peroxydases, horse radish peroxydase is illustrative. Of the hydrolases, alkaline phosphatases, β-glucosydase and lysozyme are illustrative.

Chemiluminescent Detectable Molecules

The detectable molecule comprised within the marker compound according to the invention may also consist in a chemiluminescent moiety. The chemiluminescent source involves a compound, which becomes electronically excited by a chemical reaction and may emit light which serves at as the detectable signal or donates energy to a fluorescent acceptor.

A diverse number of families of compounds have been found to provide chemiluminescent under a variety of conditions. When family of compounds is 2,3-dihydro-1,4-phtalazinedinone. The most utilised compound is luminol, which is the 5-amino analogue of the compound above. Other members of the family include the 5-amino-6,7,8-trimethoxy and the dimethylamine-[ca]benzo analogue. These compounds can be made to luminance with alkaline hydrogen peroxyde or calcium hypochlorite and base.

Another family of compounds is the 2,4,5-triphenylimidazoles, with lophine as the common name for the parent product. Chemiluminescent analogues include para-dimethylamino- and para-methoxy-substituents. Chemiluminescents may also be obtained with geridinium esters, dioxetanes and oxalates, usually oxalyl active esters, e.g., p-nitrophenyl and a peroxide, e.g., hydrogen peroxide, under basic conditions. Alternatively, luciferins may be used in conjunction with luciferase or lucigenins.

Radioactive Detectable Molecules

In a further embodiment of a detectable molecule comprised in a marker compound according to the invention, said detectable molecule is radio-actively labelled such as with [$^3$H], [$^{32}$P], and [$^{125}$I].

Colloïdal Metal Detectable Molecules

In still a further embodiment, the detectable molecule comprised in a marker compound according to the invention may include a colloïdal metal particle. Colloïdal metals have been employed in immuno assays previously. Mostly, they consisted of either colloïdal iron or gold. The one skilled in the art may advantageously refer to the articles of Horisberger (1981) and Martin et al. (1990). In other case, the metals are chosen for their colour, i.e., their presence is determined by their colour or electron density under an electron microscope. Both the colour and electron density are directly proportional to the mass of the metal colloïd.

Structure of the Marker Compounds of the Invention

In a first preferred embodiment of a marker compound of the invention, the detectable molecule is covalently bound to the Selected Interacting Domain (SID®) polypeptide of SEQ ID N°1 to SEQ ID N°38 or a variant thereof.

According to this specific embodiment, detectable molecules comprising fluorescent proteins such as GFP and YFP, enzymes or enzyme fragments such as alkaline phosphatase, glutathione peroxydase and horse radish peroxydase, chemiluminescent molecules, radioactive labels or colloidal metal particles will be preferred.

General methods that may be used by the one skilled in the art for covalently binding the detectable molecules to the Selected Interacting Domain (SID®) polypeptide are described in the numerous bibliographic references related to the preparation of the antibody conjugates used for carrying out immunoassays.

In a second preferred embodiment of a marker compound according to the invention, the detectable molecule is non-covalently bound to the Selected Interacting Domain (SID®) polypeptide or a variant thereof.

In a first preferred aspect of this second preferred embodiment, the detectable molecule consists of an antibody directed specifically against the Selected Interacting Domain (SID®) polypeptide or a variant thereof.

The antibodies directed specifically against the Selected Interacting Domain (SID®) polypeptide or a variant thereof may be indifferently radioactivity or non radioactivity labelled.

Nucleic Acids Encoding a Marker Compounds of the Invention

The present invention also relates to a nucleic acid encoding a marker compound as defined above.

Most preferred nucleic acids encompassed by the invention include polynucleotides that encode a marker compound wherein the Selected Interacting Domain (SID®) polypeptide of SEQ ID N°1 to 38 or a variant thereof is covalently bound to the detectable molecule and wherein the detectable molecule consists itself of a polypeptide.

Most preferred nucleic acids are those of SEQ ID N°39 to 76.

In a first preferred embodiment of a nucleic acid according to the invention, said nucleic acid encodes for a Selected Interacting Domain (SID®) polypeptide which is fused to a fluorescent protein, such as GFP and YFP.

In a second preferred embodiment of a nucleic acid according to the invention, said nucleic acid encodes for a Selected Interacting Domain (SID®) polypeptide which is fused to a polypeptide endowed with a catalytic activity, such as an enzyme or an enzymatically active enzyme fragment, like alkaline phosphatase, glutathione peroxydase and horse radish peroxydase.

In a preferred embodiment, a nucleic acid encoding a marker compound of the invention comprises a DNA coding sequence which is transcribed and translated into said marker compound in a cell in vitro or in vivo when placed under the control of appropriate regulatory sequences. The boundaries of the coding sequence are determined by a start codon and a translation stop codon. A coding sequence can include, but is not limited to:

prokaryotic sequences, for example when the Selected Interacting Domain (SID®) nucleic acid and the nucleic acid fused thereto which encodes the detectable molecule are of prokaryotic origin;

prokaryotic and eukaryotic sequences, for example the nucleic acid encoding the detectable molecule originates from an eukaryotic host organism.

If the coding sequence is intended for expression in an eukaryotic cell, a polyadenylation signal and transcription termination sequence will usually be located 3' to the coding sequence.

In a most preferred embodiment of a nucleic acid sequence according to the invention, said nucleic acid sequence include a regulatory region which is functional in the host organism within which the expression of said nucleic acid sequence is sought, wherein said regulatory region comprises a promoter sequence.

"Regulatory region" means a nucleic acid sequence which regulates the expression of a nucleic acid. A regulatory region may include sequences which are naturally responsible for expressing a particular nucleic acid (a homologous region), or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretary pathways of the target cell, and promoters.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

Most Preferred Vectors for the Expression of a Marker Compound of the Invention.

Most preferred recombinant vectors for expressing a marker compound of the invention include PASΔΔ (FIG. 2), pACTIIst (FIG. 3), pT18 (FIG. 4), pUT18C (FIG. 5), pT25 (FIG. 6), pKT25 (FIG. 7), pB5 (FIG. 12) and pP6 (FIG. 13) containing inserted therein a nucleic acid encoding a Selected Interacting Domain (SID®) polypeptide as defined above or a variant thereof.

The invention also pertains to recombinant host cells transformed with a vector expressing a marker compound as defined above, more particularly a vector comprising inserted therein a nucleic acid encoding said marker compound, which is operably linked to suitable regulation signals which are functional in the host cell wherein its expression is sought.

Preferred cells for expression purposes will be selected in function of the objective which is sought. For example, in the embodiment wherein the production of a marker compound according to the invention in large quantities is sought, the nature of the cell host used for its production is relatively indifferent, provided that large amounts of Selected Interacting Domain (SID®) polypeptides or marker compounds of the invention are produced and that optional further purification steps may be carried out easily.

However, in the embodiment wherein the marker compound is recombinantly produced within a host organism for the purpose of qualitative or quantitative analysis of the polypeptide of interest onto which said marker compound specifically binds, then the host organism is selected among the host organisms which are suspected to produce naturally said polypeptide of interest.

Consequently, mammalian and human cells, as well as bacterial, yeast, fungal, insect, nematode and plant cells are cell host encompassed by the invention and which may be transfected either by a nucleic acid or a recombinant vector as defined above.

Detection Methods of the Invention

The present invention further relates to the use of a Selected Interacting (SID®) polypeptide of SEQ ID N°1 to 38 or a variant thereof as well as a nucleic acid encoding it for detection purposes such as nucleic acids of SEQ ID N°39 to 76. It is herein reminded that a Selected Interacting Domain (SID®) polypeptide is determined according to the ability of such a (SID®) polypeptide to bind in a highly specific manner to a given (e.g. bait) polypeptide of interest, since the aminoacid sequence of a SID® polypeptide is encoded by a nucleic acid, the nucleotide sequence of which consists of the polynucleotide sequence which is common to a collection of nucleic acid sequences encoding prey polypeptides that have been selected for their specific binding properties to a (bait) polypeptide of interest, such as explained above in the section entitled "SELECTED INTERACTING DOMAIN (SID®) POLYPEPTIDES".

The specific properties of a Selected Interacting Domain (SID®) polypeptide for binding to a given polypeptide of interest, either a viral, yeast, fungal, bacterial, insect, plant or mammal polypeptide, including a polypeptide of human origin, allow its use as a specific ligand for said polypeptide of interest of which the detection is sought.

Therefore, the use of a Selected Interacting Domain (SID®) in any detection method known in the art and which makes use of the ability of a detection ligand to bind specifically to a molecule of interest, most preferably a polypeptide of interest, fall under the scope of the present invention.

Detection methods that make use of the recognition of a molecule of interest, most preferably a polypeptide of interest, by a detection ligand are well known in the art and are primarily illustrated by the abundant literature that relate to immunoassays, which is incorporated herein by reference in its entirety.

The one skilled in the art may particularly refer to the book of Maggio (1980) (Heterogeneous assays), the U.S. Pat. No. 3,817,837 (homogeneous Immunoassays), U.S. Pat. No. 3,993,345 (Immunofluorescense methods), U.S. Pat. No. 4,233,402 (enzyme channelling techniques), U.S. Pat. No. 3,817,837 (Enzyme multiplied immunoassay technique), U.S. Pat. No. 4,366,241 and European Patent Application N°EP-A 0 143 574 (Migration type assays), U.S. Pat. No. 5,202,006, U.S. Pat. No. 5,120,413 and U.S. Pat. No. 5,145,567 (Immunofixation electrophoresis, mmunoelectrophoresis), the article of Aguzzi et al. (1977), the article of White et al. (1986), the article of Merlini et al. (1983), the U.S. Pat. No. 5,228,960 (Immunosubstraction electrophoresis), the articles of Chen et al. (1991), Nielsen et al. (1991) and the U.S. Pat. No. 5,120,413 (Capillary electrophoresis).

Acellular Detection Method of the Invention

A first detection method of the invention consists of a method for detecting a polypeptide of interest within a sample, wherein said method comprises the steps of:

a) contacting a marker compound or a plurality of marker compounds according to the invention with the sample which is suspected to contain the polypeptide of interest the detection of which is sought;

b) detecting the complexes formed between said marker compound or said plurality of marker compounds and said polypeptide of interest.

The sample which is assayed for the presence of the polypeptide of interest the detection of which is sought may be of any nature , including every sample that may be used for carrying out an immunoassay.

In a first aspect, the sample may be any biological fluid, such as blood or blood separation products (e.g. serum, plasma, buffy coat), urine, saliva, tears.

In a second aspect, the sample may be any isolated biological tissue sample, including tissue sections previously fixed for purposes of histological studies.

In a third aspect, the sample may be a culture supernatant of a cell culture and a cell lysate of cultured cells.

In a first preferred embodiment of the first detection method of the invention described above, the detection step b) consists of the measure of the fluorescence signal intrinsically emitted by the detectable molecule. It may for example be taken the advantage of SID® polypeptides or variants thereof having in their aminoacid sequence one or several tryptophan aminoacid residues.

In a second preferred embodiment of the first detection method of the invention detailed above, the detection step b) consists of submitting the detectable molecule to a source of energy at the excitation wavelength of said detectable molecule, and measuring the light emitted at the emission wavelength of said detectable molecule.

An illustrative example of this second embodiment above is when the marker compound used consists of a Selected Interacting Domain (SID®) which is bound to a fluorescent molecule, such as the fluorescent proteins GFP or YFP.

For example, in the embodiment wherein the detectable molecule of the marker compound of the invention which is used according to the first detection method above comprises, or alternatively consists of, a GFP protein, the detection step c) includes illuminating the sample tested at an emission wavelength substantially equal to 490 nm, and measuring the light emitted by the marker compound which is bound to the polypeptide of interest within the sample at an emission wavelength substantially equal to 510 nm.

Preferably, the marker compounds which are not bound to the polypeptide of interest the detection of which is sought within the sample are removed before carrying out the detection step.

In a third preferred embodiment, the detection step c) of the first detection method of the invention consists of measuring the catalytic activity of the detectable molecule. In this specific embodiment, the marker compound used in the detection method comprises a detectable molecule which comprises, or alternatively which consists of, an enzyme or a catalytically active enzyme fragment, such as already detailed in the section entitled "Marker compounds of the invention".

In a fourth preferred embodiment, the detection step b) consists of measuring the radioactivity emitted by the detectable molecule.

The present invention further relates to a kit for detecting a polypeptide of interest within a sample, wherein said kit comprises a marker compound according to the invention.

Optionally, said detection kit further comprises the reagents necessary for carrying out the detection step b), such as a suitable substrate for the particular enzyme or a catalytically active enzyme fragment used, as well as suitable buffer solutions, which may be identical to those conventionally used for performing immunoassays.

Cellular Detection Assay Using a Recombinantly Produced Marker Compound of the Invention.

As already described above, any marker compound according to the invention may be produced according to genetic engineering techniques. Particularly, nucleic acid encoding a particular marker compound which binds specifically to a polypeptide of interest the detection of which is sought may be inserted in a vector, wherein said vector may be used to transfect or transform a host organism, either a prokaryotic or an eukaryotic cell host such as defined above.

In this specific embodiment, the production of a recombinant marker compound of the invention is allowed within such a transfected or transformed host cell. Once the host cell of interest is transfected or transformed with such a recombinant vector and once the recombinant marker compound is produced within the cell host of interest, then the Selected Interacting Domain (SID®) polypeptide portion of said marker compound will be able to bind specifically to its specific target polypeptide within the cell host. In this situation, the recombinantly produced marker compound of the invention will predominantly be localised at cell sites wherein the targeted polypeptide of interest is present.

This is the purpose of the second detection method of the invention which is detailed below.

A further object of the invention consists of a method for detecting a polypeptide of interest within a prokaryotic or an eukaryotic cell host, wherein said method comprises the steps of:

a) providing a cell host to be assayed;

b) transfecting said cell host with a nucleic acid encoding a marker compound of the invention, or with a recombinant vector encoding a marker compound of the invention;

c) detecting the complexes formed between the marker compound expressed by the transfected cell host and the polypeptide of interest.

Because the Selected Interacting Domain (SID®) polypeptide which is part of a marker compound of the invention specifically binds to a polypeptide which is suspected to be naturally produced by the targeted cell host, the second detection method of the invention defined above allows a qualitative as well as a quantitative detection of this targeted polypeptide which is suspected to be naturally produced by the transfected target cell host under assay.

For example, in the embodiment within which the procedure for selecting the Selected Interacting Domain (SID®) polypeptide which is part of a marker compound of the invention includes a first step wherein a collection of clones containing nucleic acid inserts derived from a H77 strain HCV genomic DNA library is prepared, the transfection of a mammalian cell, preferably a human cell, with a vector encoding such a marker compound of the invention will allow to detect the expression of a human polypeptide naturally expressed within said mammalian host cell and which naturally interacts with the HCV viral protein from which is derived the Selected Interacting Domain (SID®) polypeptide.

The second detection method of the invention defined above firstly allows the qualitative detection of the targeted polypeptide of interest which binds specifically with the recombinantly produced marker compound of the invention, and thus permits to know in which environmental conditions or at which differentiation stage the targeted polypeptide of interest is naturally produced within the cell host transfected with a vector expressing a marker compound of the invention.

Secondly, this second detection method of the invention allows the localisation of the targeted polypeptide of interest within the interior of the cell, including localisation in the plasma membrane, cytosol, nucleus and any organelle such as ribosomes, Golgi apparatus, lysosomes, phagosomes, endoplasmic reticulum and chloroplasts.

The localisation of a targeted polypeptide of interest which is expressed within the cell host under assay according to the second detection method of the invention may be carried out by any means well known in the art, including using a confocal microscope.

Thirdly, the second detection method of the invention allows also a quantitative analysis of the expression of the targeted polypeptide of interest within the cell host under assay, since the level of the detection signal produced by the detectable molecule which is part of the marker compound will be proportional to the number of complexes formed between the cell host under assay between the targeted polypeptide of interest and the recombinantly produced marker compound of the invention.

Essentially, the one skilled in the art may refer to the section entitled "Acellular detection method of the invention" above to find the teachings necessary for performing the detection step c) of the second detection method described herein.

In a first embodiment of said second detection method of the invention, the detection step c) consists of the measure of the fluorescence signal intrinsically emitted by the detectable molecule comprised in the recombinantly expressed marker compound of the invention.

In a second preferred embodiment of the second detection method above, the detection step c) consists of submitting the detectable molecule to a source of energy at the excitation wavelength of said detectable molecule and measuring the light emitted at the emission wavelength of said detectable molecule.

In still a further embodiment of the second detection method of the invention, the detection step c) consists of measuring the catalytic activity of the detectable molecule.

In another embodiment, the detection step c) consists of measuring the radioactivity emitted by the detectable molecule.

In yet a further embodiment of the second detection method of the invention, the detection step c) allows the location of the complexes formed between the recombinantly produced marker compound and the targeted polypeptide of interest within the transfected cell host.

A further object of the invention consists of a kit for detecting a polypeptide of interest within a prokaryotic or an eukaryotic cell host, wherein said kit comprises a nucleic acid encoding a marker compound as defined herein, or a recombinant vector containing inserted therein a nucleic acid encoding a marker compound of the invention.

Optionally, the detection kit above may further comprise the reagents necessary to carry out the detection step c).

Cellular Detection Method of the Invention Using a Marker Compound which is Introduced within a Cell Host There is a third detection method according to the invention wherein the marker compound comprising a Selected Interacting Domain (SID®) polypeptide OF SEQ ID N°1 to 38 or a variant thereof is previously produced by any means and subsequently introduced into a target cell host for the purpose of detecting a targeted polypeptide of interest which binds specifically with said Selected Interacting Domain (SID®) polypeptide.

Thus, the invention further relates to a method for detecting a polypeptide of interest within a prokaryotic or an eukaryotic cell host, wherein said method comprises the step of:

a) providing a cell host to be assayed;

b) introducing a marker compound as defined herein within said cell host; and c) detecting the complexes formed between the marker compound and the polypeptide of interest within the cell host.

Taking into account the low molecular weight of the Selected Interacting Domain (SID®) polypeptide selected from SEQ ID N°1 to 38 which is part of a marker compound of the invention, when compared with conventional specific detection molecules such as antibodies or antibody fragments, it results that the introduction of a marker compound of the invention into the interior of a target cell host will be much more easier to perform, as compared with the introduction within a cell host of a conventional marker like a labelled antibody or a labelled antibody fragment.

According to the third detection method of the invention defined above, step b) of introducing the marker compound within the target cell host may be performed by any technique well known in the art, including electroporation, and the use of molecules that will facilitate the passage of the marker compound of the invention through the cell membranes, and typically the plasma membrane.

Such molecules that facilitate the passage of a marker compound of the invention through cell membranes include, but are not limited to, penetratin, like penetratin 1.RTM (Encor, Gaithersburg, Md.), Antenna Pediae protein, cationic lipids and cationic polyacrylates.

Permeation enhancers which may be employed include bile salts such as sodium glycocholate and other molecules such as β-cyclodextrin. Bile salts are known to increase the absorption of macromolecules across membranes (Pontiroli et al., 1987).

As already detailed for the second detection method of the invention described in the previous section, the third detection method of the invention allows also the localisation of the targeted polypeptide of interest which is expressed by the cell host under assay, as well as the qualitative and quantitative analysis of the expression of said target polypeptide of interest.

The detection step c) according to the third detection method of the invention described above may be carried out in the same way than the detection step c) of anyone of the first detection method and the second detection method detailed in the previous sections herein.

In a first embodiment of the third detection method above, the detection step c) consists of the measure of the fluorescence signal intrinsically emitted by the detectable molecule.

In a second embodiment, the detection step c) consists of submitting the detectable molecule to a source of energy at the excitation wavelength of said detectable molecule and measuring the light emitted at the emission wavelength of said detectable molecule.

In a third embodiment, the detection step c) consists of measuring the catalytic activity of the detectable molecule.

In a fourth embodiment, the detection step c) consists of measuring the radioactivity emitted by the detectable molecule.

In a fifth embodiment of the third detection method of the invention, the detection step c) allows the location of the complexes formed between the marker compound and the polypeptide of interest within the target cell host under assay.

A further object of the invention consists of a kit for detecting a polypeptide of interest within a prokaryotic or an eukaryotic cell host, wherein said kit comprises a marker compound as defined herein.

The detection kit above may further comprise the reagents necessary to carry out the detection step c).

The detection kit above may also further comprise the reagents necessary to facilitate the introduction of the marker compound within the target cell host under assay.

Solid Phase Detection Method Using a Selected Interacting Domain (SID®) Polypeptide In a further aspect of the invention, the use of a Selected Interacting Domain (SID®) polypeptide of SEQ ID N°1 to 38or a variant thereof for detection purpose include a step wherein said Selected Interacting Domain (SID®) polypeptide is immobilised on a suitable substrate before bringing a sample to be assayed in contact with the substrate onto which said Selected Interacting Domain (SID®) polypeptide has been previously immobilised.

A subsequent step will consist in detecting the complexes formed between the Selected Interacting Domain (SID®) polypeptide immobilised on the substrate and the targeted polypeptide of interest the presence of which is suspected in the sample assayed.

Thus, the invention also pertains to a fourth detection method which consists of a method for detecting a polypeptide or a plurality of polypeptides of interest within a sample, wherein said method comprises the steps of:

a) providing a substrate onto which a Selected Interacting Domain (SID®) polypeptide or a plurality of Selected Interacting Domain (SID®D) polypeptides is (are) immobilised;

b) bringing into contact the substrate defined in a) with the sample to be assayed;

c) detecting the complexes formed between the Selected Interacting Domain (SID®) polypeptide or the plurality of Selected Interacting Domain (SID®) polypeptides and the target polypeptide or the plurality of target polypeptides contained in the sample.

Substrates, supports or surfaces for immobilising protein molecules are well known in the art, and a lot of them have been described for performing solid phase immunoassays.

Preferably, a plurality of Selected Interacting Domain (SID®) polypeptides of different aminoacid sequences choosen among the sequences SEQ ID N°1 to 38 are immobilised on the substrate used according to the fourth detection method of the invention.

For example, a complete collection of Selected Interacting Domain (SID®) polypeptides which have been determined according to the methods described in the section entitled "Selected Interacting Domain (SID®) polypeptides" above, using nucleic acids derived from the H77 strain HCV genomic DNA as starting material, may be used for being immobilised on a suitable substrate.

According to this embodiment, the collection of Selected Interacting Domain (SID®) polypeptides of SEQ ID N°1 to 38 are immobilised on the substrate in another manner, thus forming an ordered area of SID® polypeptides immobilised at known locations of the surface of said substrate.

The substrate, support or surface may be a porous or a non-porous water insoluble material. The support can be hydrophilic or capable of being rendered hydrophilic and includes inorganic powders such as silica, magnesium sulphate, and alumina; natural polymeric materials, particularly cellulosic materials and materials derived from cellulose, such as fiber containing papers; synthetic or modified naturally occurring polymers, such as nitrocellulose, cellulose acetate, poly(vinyl chloride), polyacrylamide , cross-linked dextran, agarose, polyacrylate, polyethylene, polypropylene, poly(4-methylbutene), polystyrene, polymethacrylate, poly(ethylene terephtalate), nylon, poly(vinyl butyrate), said materials being used by themselves or in conjunction with other materials; glass available as Bioglass, ceramic metals and the like.

An ordered area onto which a plurality of Selected Interacting Domain (SID®) polypeptides are immobilised may be manufactured according to the techniques disclosed in the U.S. Pat. No. 5,143,854 or the PCT Application No. WO 92/10092, incorporated herein by reference for all purposes. The combination of photolithographic and fabrication techniques may, for example, enable each Selected Interacting Domain (SID®) polypeptide to occupy a very small area ("site") on the support. In some embodiments, the site may be as small as few microns or even a single Selected Interacting Domain (SID®) polypeptide.

In a first embodiment of the fourth detection method detailed above, the plurality of Selected Interacting Domain (SID®) polypeptides are immobilized on the substrate in an order manner.

In a second embodiment of Selected interacting Domain (SID®), the Selected Interacting Domain (SID®) polypeptide or the plurality of Selected Interacting Domain (SID®) polypeptides are covalently bound to the substrate.

In a third embodiment of said method, the Selected Interacting Domain (SID®) polypeptide or the plurality of Selected Interacting Domain (SID®) polypeptides are non-covalently bound to the substrate. According to this specific embodiment, the Selected Interacting Domain (SID®) polypeptide or the plurality of Selected Interacting Domain (SID®) polypeptides are covalently bound to a first ligand molecule and the substrate is coated with a second ligand molecule, wherein said second ligand molecule specifically binds to the first ligand molecule. According to such a specific embodiment, the first ligand may be biotin in which case the second ligand is most preferably streptavidin.

In still a further embodiment of the fourth detection method according to the invention, the Selected Interacting Domain (SID®) polypeptide or the plurality of Selected Interacting Domain (SID®) polypeptides are covalently linked to a spacer, which spacer is itself also covalently bound to the substrate in order to immobilise the Selected Interacting Domain (SID®) polypeptide or the plurality of Selected Interacting Domain (SID®) polypeptides onto said substrate. Such a spacer may be a peptide polymer such as a poly-alanine or a poly-lysine peptide of 10 to 15 amino acids in length.

In still a further embodiment of the fourth detection method above, the detection step c) consists of detecting changes in the optical characteristics of the substrate onto which the Selected Interacting Domain (SID®) polypeptide or the plurality of Selected Interacting Domain (SID®) polypeptides are bound.

In yet a further embodiment of the fourth detection method of the invention, the detection step c) consists of bringing into contact the substrate wherein complexes are formed between the targeted polypeptide molecule contained in the sample assayed and the Selected Interacting Domain (SID®) polypeptide or the plurality of Selected Interacting Domain (SID®) polypeptides bound to said support, with a detectable molecule having the ability to bind to such complexes.

A further object of the invention consists of a device or an apparatus for the detection of a polypeptide or a plurality of polypeptides of interest within a sample, wherein said device or apparatus comprises a substrate onto which a Selected Interacting Domain (SID®) polypeptide (or a plurality of Selected Interacting Domain (SID®) polypeptides) is (are) immobilised.

Such a device or apparatus of the invention above may comprise or consist of a suitable substrate onto which the plurality of Selected Interacting Domain (SID®) polypeptides are arranged in an ordered manner, thus forming an area such as described above.

Pharmaceutical Compositions Containing a Selected Interacting Domain (SID®) Polypeptide It results from the method according to which a Selected Interacting Domain (SID®) polypeptide of SEQ ID N°1 to 38 has been selected and characterized that such a Selected Interacting Domain (SID®) polypeptide or a variant thereof is both:

(i) endowed with highly specific binding properties to a (bait) polypeptide of interest; and (ii) devoid ed of the biological activity of the naturally occurring protein from which this Selected Interacting Domain (SID®) polypeptide or a variant thereof is derived.

These original properties of a Selected Interacting Domain (SID®) polypeptide of SEQ ID N°1 to 38 or a variant thereof allow its use for interfering with a naturally occurring interaction between a first protein and a second protein within the cell of an organism by the binding of said Selected Interacting Domain (SID®) polypeptide specifically either to said first polypeptide or said second polypeptide.

The (SID®) polypeptides of the invention or variants thereof are capable of interfering with the in vivo protein-protein interactions between HCV proteins or between a HCV protein and a protein from the organism which has been infected with the Hepatitis C virus.

For example the SID® polypeptide of SEQ ID N°2 interferes with the naturally occurring interaction between the core and the NS3 protein HCV. Similarly, the SID® polypeptide of SEQ ID N°17 interferes with the interaction between the NS4A and the NS4B proteins (see table Thus, another object of the invention consists of a pharmaceutical composition comprising a pharmaceutically effective amount of a Selected Interacting Domain (SID®) polypeptide or a variant thereof.

The invention also relates to a pharmaceutical composition comprising a pharmaceutically effective amount of a nucleic acid comprising a polynucleotide encoding a Selected Interacting Domain (SID®) polypeptide of SEQ ID N°1 to 38 or a variant thereof which polynucleotide is placed under the control of an appropriate regulatory sequence.

Preferred nucleic acids are the nucleotide sequences SEQ ID N°39 to 76.

The invention also pertains to a pharmaceutical composition comprising a pharmaceutically effective amount of a recombinant expression vector comprising a polynucleotide encoding the Selected Interacting Domain (SID®) polypeptide or a variant thereof.

The invention also pertains to a method for preventing or curing a viral infection by a hepatitis C virus in a human or an animal, wherein said method comprises a step of administering to the human or animal body a pharmaceutically effective amount of a Selected Interacting Domain (SID®) polypeptide of SEQ ID N°1 to 38 or a variant thereof which binds to a targeted viral or mammal, typically- human protein.

A pharmaceutical composition as described above, wherein said composition is administered by any route, such as intravenous route, intramuscular route, oral route, or mucosa route with an acceptable physiological carrier and/or adjuvant, also forms part of the invention.

The Selected Interacting Domain (SID®) polypeptide or a variant thereof as a medicament for the prevention and/or treatment of pathologies induced by HCV are the most preferred.

The Selected Interacting Domain (SID®) polypeptides of SEQ ID N°1 to 38 as active ingredients of a pharmaceutical composition will be preferably in a soluble form combined with a pharmaceutically acceptable vehicle.

Such compounds which can be used in a pharmaceutical composition offer a new approach for preventing and/or treating pathologies linked to infection by HCV. Preferably, these compounds will be administered by the systemic route, in particular by the intravenous route, by the intramuscular or intra dermal route or by the oral route.

Their modes of administration, optimum dosages and galvanic forms can be determined according to the criteria generally taken into account in establishing a treatment suited to a patient, such as for example the age or body weight of the patient, the seriousness of his general condition, the tolerance to treatment and the side effects observed, and the like.

The identified compound can be administered to a mammal, including a human patient, alone or in pharmaceutical compositions where they are mixed with suitable carriers or excipients at therapeutically effective doses to treat disorders associated with prokaryotic micro-organism infection. Techniques for formulation and administration of the compounds of the invention may be found in "Remington's Pharmaceutical Sciences" Mack Publication Co., Easton, Pa., latest edition.

For any Selected Interacting Domain (SID®) polypeptide or any variant thereof used according to the invention, the therapeutically effective dose can be estimated initially from cell culture assays. For example, a dose can be formulated in animal models to achieve a circulating concentration range that includes or encompasses a concentration point or range shown the desired effect in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g. for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50 Compounds which exhibit high therapeutic indices are preferred.

The data obtained from these cell culture assays and animal studies can be used in formulating a range of dosage for use in human. The dosage of such compounds lies preferably within a range of circulating concentrations that include the ED50, with little or no toxicity. The dosage may vary within this range depending upon the dosage form employed and the route of administration utilised. The exact formulation, route of administration and dosage can be chosen by the individual physician in view of the patient's condition. (See, e.g. Fingl et al. 1975, in "The Pharmacological Basis of Therapeutics", CH.I).

Dosage amount and interval may be adjusted individually to provide plasma levels of the active compound which are sufficient to maintain the modulating effects. Dosages necessary to achieve the modulating effect will depend on individual characteristics and route of administration.

The amount of composition administered will, of course, be dependent on the subject being treated, on the subject's weight, the severity of the affliction, the manner of administration and the judgement of the prescribing physician.

The invention also pertains to a method for preventing or curing a viral in a human or an animal, wherein said method comprises the step of administering to the human or animal body a pharmaceutically effective amount of a nucleic acid comprising a polynucleotide encoding a Selected Interacting Domain (SD®) polypeptide of SEQ ID N°1 to 38, or a variant thereof, and wherein said polynucleotide is placed under the control of a regulatory sequence which is functional in said human or said animal.

Preferred polynucleotides are the nucleic acids of SEQ ID N°39 to 76.

The invention also relates to a method for preventing or curing a viral or in a human or an animal, wherein said method comprises the step of administering to the human or animal body a pharmaceutically effective amount of a recombinant expression vector comprising a polynucleotide encoding a Selected Interacting Domain (SD®) polypeptide which binds to a viral or bacterial protein.

Other characteristics and advantages of the invention appear in the remainder of the description with the examples below, without linking the invention in any manner.

EXAMPLES

Preparation of a HCV Genomic Collection

1.A. Collection Preparation and Transformation in *Escherichia coli*

1.A.1 Fragmentation of Genomic DNA Preparation.

The genomic DNA of the infectious HCV strain H77 (Yanagi et al., P.N.A.S. 1997, 94, 8738–43) is fragmented in a nebulizer (GATC) for 2 minutes at a pressure of 2 bars, precipitated and resuspended in water.

The obtained nubilized genomic DNA is successively treated with Mung Bean Nuclease (Biolabs) (30 minutes at 30° C.), T4 DNA polymerase (Biolabs) (10 minutes at 37° C.) and Klenow enzyme (Pharmacia) (10 minutes at room temperature and 1 hour at 16° C.).

DNA is then extracted, precipitated and resuspended in water.

1.A.2. Ligation of Linkers to Blunt-ended Genomic DNA

Oligonucleotide HGX931 (5' end phosphorylated) 1 µg/µl and HGX932 1 µg/µl.

Sequence of the oligo HGX931: 5'-GGGCCACGAA-3' (SEQ ID N°151).

Sequence of the oligo HGX932: 5'-TTCGTGGCCCCTG-3' (SEQ ID N°152).

Linkers were preincubated (5 minutes at 95° C., 10 minutes at 68° C., 15 minutes at 42° C.) then cooled down at room temperature and ligated with genomic DNA inserts at 16° C. overnight.

Linkers were further removed on a separation column (Chromaspin TE 400, Clontech), according to the manufacturer's protocol.

1.A.3. Vector Preparation

Plasmid pP6 (see FIG. 13) was prepared by replacing the SpeI/XhoI fragment of pGAD3S2X with the double-stranded oligonucleotide:

5'CTAGCCATGGCCGCAGGGGCCGCGGCCGCACTAGTGGGGATCCTTAAT

TAAAGGGCCACTGGGGCCCCCCGTACCGGCGTCCCCGGCGCCGGCGTGAT

CACCCCTAGGAATTAATTTCCCGGTGACCCCGGGGAGCT 3'

(SEQ ID N° 153).

The pP6 vector is successively digested with Sfi1 and BamHI restriction enzymes (Biolabs) for 1 hour at 37° C., extracted, precipitated and resuspended in water. Digested plasmid vector backbones are purified on a separation column (Chromaspin TE 400, Clontech), according to the manufacturer's protocol.

1.A.4 Ligation Between Vector and Insert of Genomic DNA

The prepared vector is ligated overnight at 15° C. with the genomic blunt-ended DNA described in section 2 using T4 DNA ligase (Biolabs). The DNA is then precipitated and resuspended in water.

1.A.5. Library Transformation in *Escherichia coli*

Transform DNA from section 1.A.4. into Electromax DH10B electrocompetent ells (Gibco BRL) with Cell Porator apparatus (Gibco BRL). Add 1 ml SOC medium and incubate transformed cells at 37° C. for 1 hour. Add 9 ml volume of SOC medium per tube and plate on LB+ampicillin medium. Scrape colonies with liquid LB medium. Aliquot and freeze at −80° C.

The obtained collection of recombinant cell clones is named HGXBHCV1.

1.B. Collection Transformation in *Saccharomyces cerevisiae*

The *Saccharomyces cerevisiae* strain (Y187 (MATα Gal4Δ Ga180Δ ade2-101 His3 Leu2-3, -112 Trp1-901 Ura3-52 URA3::UASGAL1-LacZ Met) transformed with the HGXBHCV1 HCV genomic DNA library.

The plasmid DNA contained in *E. coli* are extracted (Qiagen) from aliquoted *E. coli* frozen cells (1.A.5.).

Grow *Saccharomyces cerevisiae* yeast Y187 in YPGlu.

Yeast transformation is performed according to standard protocol (GIEST et al. Yeast, 11, 355–360, 1995) using yeast carrier DNA (Clontech). This experiment leads to $10^4$ to $5.10^4$ cells/µg DNA. Spread $2.10^4$ cells on DO-Leu medium per plates. Aliquot and freeze at −80° C. The obtained collection of recombinant cell clones is named HGXY-HCV1.

1.C. Construction of Bait Plasmids

Plasmid pB5 (see FIG. 12) is prepared by replacing the NcoI/SalI polylinker fragment with the double-stranded oligonucleotide.

5'CATGGCCGCAGGGGCCGCGGCCGCACTAGTGGGGATCCTTAATTAAA

GGGCCACTGGGGCCCCCCGGCGTCCCCGGCGCCGGCGTGATCACCCCTAG

GAATTAATTTCCCGGTGACCCCGGGGAGCT 3'.

(SEQ ID N° 154).

The linkered genomic DNA described in section 2 is ligated into pB5 that has been digested with Sfi1 restriction enzyme and DNA transformed into competent *E. coli*. Cells are grown and plasmid DNA extracted and sequenced. Those plasmids which code in-frame fusion proteins are used as bait plasmids.

EXAMPLE 2

Screening the Collection with the Two-hybrid in Yeast System

2.A. The Mating Protocol.

We have chosen the mating two-hybrid in yeast system (firstly described by FROMONT-RACINE et al., Nature Genetics, 1997, vol. 16, 277–282, Toward a functional analysis of the yeast genome through exhaustive two-hybrid screens) for its advantages but we could also screen the HCV collection in classical two-hybrid system as described in Fields et al. or in a yeast reverse two-hybrid system.

The mating procedure allows a direct selection on selective plates because the two fusion proteins are already produced in the parental cells. No replica plating is required. This protocol is written for the use of the library transformed into the Y187 strain.

Before mating, transform *S. cerevisiae* (CG 1945 strain (MATa Ga14-542 Gal180-538 ade2-101 His3*200 Leu2-3, -112 Trp1-901 Ura3-52 Lys2-801 URA::GAL4 17 mers (X3)- CyC1TATA-LacZ LYS2::GAL1UAS-GAL1TATA-HIS3 CYH$^R$)) according to step 1.B. and spread on DO-Trp medium.

Day 1, Morning: Preculture

Preculture of Y187 cells carrying the bait plasmid obtained at step 1.C. in 20 ml DO-Trp medium. Grow at 30° C. with vigorous agitation.

Day 1, Late Afternoon: Culture

Measure $OD_{600\ nm}$ of the DO-Trp pre-culture of Y187 cells carrying the bait plasmid preculture. The $OD_{600\ nm}$ must lie between 0.1 and 0.5 in order to correspond to a linear measurement. Inoculate 50 ml DO-Trp at $OD_{600\ nm}$ 0.006/ml, grow overnight at 30° C. with vigorous agitation.

Day 2: Mating

Medium and Plates

1 YPGlu 15 cm plate
50 ml tube with 13 ml DO-Leu-Trp-His
100 ml flask with 5 ml of YPGlu
8 DO-Leu-Trp-His plates
2 DO-Leu plates
2 DO-Trp plates
2 DO-Leu-Trp plates Measure $OD_{600\ nm}$ of the DO-Trp culture. It should be around 1.

For the mating, you must use twice as many bait cells as library cells. To get a good mating efficiency, you must collect the cells at $10^8$ cells per $cm^2$.

Estimate the amount of bait culture (in ml) that makes up 30 $OD_{600\ nm}$ units for the mating with the prey library.

Thaw a vial containing the HGXYHCV1 library slowly on ice. Add the 0.5 ml of the vial to 5 ml YPGlu. Let those cells recover at 30° C., under gentle agitation for 10 minutes.

Mating

Put the 30 $OD_{600\ nm}$ units of bait culture into a 50 ml flacon tube.

Add the HGXYHCV1 library culture to the bait culture. Centrifuge, discard the supernatant and resuspend in 0.8 ml YPGlu medium.

Distribute the cells onto a YPGlu plate with glass beads. Spread cells by shaking the plates.

Incubate the plate cells-up at 30° C. for 4 h 30 min.

Collection of Mated Cells

Wash and rinse the plate with 6 ml and 7 ml consecutively of DO-Leu-Trp-His.

Perform two parallel serial ten-fold dilutions in 500 µl DO-Leu-Trp-His up to 1/10,000. Spread out 50 µl of each 1/10000 dilution onto DO-Leu and DO-trp plates and 50 µl of each 1/1000 dilution onto DO-Leu-Trp plates.

Spread 3.2 ml of collected cells in 400 µl aliquots on DO-Leu-Trp-His+Tet plates.

Day 4

Selection of clones able to grow on DO-Leu-Trp-His+ Tetracyclin: this medium allows us to isolate diploid clones presenting an interaction.

Count the Trp+Leu+ colonies on control plates and the total number of His+ colonies on the DO-Leu-Trp-His+ Tetracyclin plates.

The number of His+ cell clones will define which protocol is to be processed:

Upon $2.10^6$ Trp+Leu+ colonies:

if number of His+ cell clones <95: then process luminometry protocol on all colonies;

if number of His+ cell clones >95 and <5000: then process luminometry protocol on 95 colonies;

if number of His+ cell clones >500: repeat screen using DO-Leu-Trp-His+Tetracyclin plates containing 3-aminotriazol.

2.B The Luminometry Assay

Grow His+ colonies overnight at 30° C. in microtiter plates containing DO-Leu-Trp-His-Tetracyclin medium with shaking. The day after, dilute 15 times overnight culture into a new microtiter plate containing the same medium. Incubate 5 hours at 30° C. with shaking. Dilute samples 5 times and read $OD_{600\ nm}$. Dilute again to obtain between 10 000 and 75 000 yeast cells/well in 100 µl final volume.

Per well, add 76 µl of One Step Yeast Lysis Buffer (Tropix), 20 µl Sapphirell Enhancer (Tropix), 4 µl Galacton Star (Tropix), incubate 40 minutes at 30° C.

Measure the β-Gal read-out (L) using a Luminometer (Trilux, Wallach).

Calculate value of $OD_{600\ nm}$×L and selected interacting preys having highest values.

At this step of the protocol, we have isolated diploid cell clones presenting interaction. The next step is now to identify polypeptides involved in the selected interactions.

EXAMPLE 3

Identification of Positive Clones

3.A. PCR on Yeast Colonies

Introduction

PCR amplification of fragments of plasmid DNA directly on yeast colonies is a quick and efficient procedure to identify sequences cloned into this plasmid. It is directly derived from a published protocol (Wang H. et al., Analytical Biochemistry, 237, 145–146, 1996). However, it is not a standardized protocol: in our hands it varies from strain to strain, and is dependent on experimental conditions (number of cells, Taq polymerase source, etc). This protocol should be optimized to specific local conditions.

Materials

For 1 well, PCR mix composition is:

| | |
|---|---|
| 32.5 µl | water |
| 5 µl | 10X PCR buffer (Pharmacia), |
| 1 µl | dNTP 10 mM, |
| 0.5 µl | Taq polymerase (85 µ/µl -Pharmacia), |
| 0.5 µl | oligonucleotide ABS1 10 pmole/µl:5'-GCGTTTGGAATCACTACAGG-3', |
| 0.5 µl | oligonucleotide ABS2 10 pmole/µl:5'-CACGATGCACGTTGAAGTG-3'. |
| 1N NaOH. | |

Experiment

Grow positive colonies overnight at 30° C. on a 96 well cell culture cluster (Costar), containing 150 µl DO-Leu-Trp-His+Tetracyclin with shaking. Resuspend culture and transfer immediately 100 µl on a Thermowell 96 (Costar).

Centrifuge 5 minutes at 4000 rpm at room temperature.

Remove supernatant. Dispense 5 µl NaOH in each well, shake 1 minute.

Place the Thermowell in the thermocycler (GeneAmp 9700, Perkin Elmer) 5 minutes at 99.9° C. and then 10 minutes at 4° C.

In each well, add PCR mix, shake well.

Set up the PCR program as followed:

| | | |
|---|---|---|
| 94° C. | 3 minutes | |
| 94° C. | 30 seconds | |
| 53° C. | 1 minute 30 seconds | x35 cycles |
| 72° C. | 3 minutes | |
| 72° C. | 5 minutes | |
| 15° C. | ∞ | |

Check the quality, the quantity and the length of the PCR fragment on agarose gel.

The length of the cloned fragment is the estimated length of the PCR fragment minus 300 base pairs that correspond to the amplified flanking plasmid sequences.

3.B Plasmids Rescue from Yeast by Electroporation

Introduction

The previous protocol of PCR on yeast cell may not be successful, in such a case, we rescue plasmids from yeast by electroporation. This experiment allows the recovery of prey plasmids from yeast cells by transformation of E.coli with a yeast cellular extract.

We can then amplify the prey plasmid and sequence the cloned fragment.

Material

Plasmid Rescue

Glass beads 425–600 µm (Sigma)

Phenol/chloroform (1/1) premixed with isoamyl alcohol (Amresco)

Extraction buffer: 2% Triton ×100, 1% SDS, 100 mM NaCl, 10 mM TrisHCl pH 8.0, 1 mM EDTA pH 8.0.

Mix ethanol/NH$_4$Ac: 6 volumes ethanol with 7.5 M NH$_4$ Acetate, 70% Ethanol and yeast cells in patches on plates.

Electroporation

SOC medium

M9 medium

Selective plates: M9-Leu+Ampicillin 2 mm electroporation cuvettes (Eurogentec)

Experiment

Plasmid Rescue

Prepare cell patch on DO-Leu-Trp-His with cell culture of section 2.C.

Scrape the cell of each patch in Eppendorf tube, add 300 µl of glass beads in each tube, then add 200 µl extraction buffer and add 200 µl phenol:chloroform:isoamyl alcohol (25:24:1).

Centrifuge tubes 10 minutes at 15000 rpm.

Transfer 180 µl supernatant to a sterile Eppendorf tube and add to each 500 µl ethanol/NH$_4$Ac, vortex.

Centrifuge tubes 15 minutes, 15000 rmp at 4° C.

Wash pellet with 200 µl 70% ethanol, remove ethanol and dry pellet,

Resuspend pellet in 10 µl water. Store extracts at −20° C.

Electroporation

Material: Electrocompetent MC1066 cells prepared according to standard protocols (Maniatis).

Add 1 µl of yeast plasmid DNA-extract to pre-chilled Eppendorf tube, and keep on ice.

Mix 1 µl plasmid yeast DNA-extract sample, add 20 µl electrocompetent cells and transfer in a cold electroporation cuvette.

Set the Biorad electroporator on 200 ohms resistance, 25 µF capacity; 2.5 kV. Place cuvette in the cuvette holder and electroporate.

Add 1 ml SOC into the cuvette and transfer the cell-mix into sterile Eppendorf tube.

Let cells recover for 30 minutes at 37° C., spin the cells down 1 minute, 4000×g and pour off supernatant. Keep about 100 µl medium and use it to resuspend the cells and spread them on selective plates (e.g. M9-Leu plates).

Incubate plates for 36 hours at 37° C.

Grow one colony and extract plasmids. Check presence and size of insert through enzymatic digestion and agarose gel. Sequence insert.

EXAMPLE 4

Protein-Protein Interaction

For each bait, the previously protocol leads to the identification of prey polynucleotide sequences. Using a suitable software program (eg Blastwun, available on the Internel site of the University of Washington: http:/bioweb.pasteur.fr/seqanal/interfaces/blastwu.html) the region of the HCV genome is encoded by the prey fragment may be determined and whether the fusion proteins encoded are in the same open reading frame of translation as the HCV polyprotein or not.

EXAMPLE 5

Identification of SID®

The presence of contiguous polypeptides in the HCV genome and the high complexity of the prey library used prevents the determination of SID®s by previous means since prey fragments can overlap multiple polypeptides. The high complexity of the prey library used relative to the small genome size also prevented such a simple analysis since prey fragments can overlap multiple interacting domains. It was also necessary to overcome the problems caused by protein preys encoded by out-of-frame fusions of regions of the HCV genome.

In order to determine the SID®s for a particular bait protein, it was therefore necessary to devise a suitable algorithm which would take into account all these problems:

5.1. The prey fragments are initially sorted according to which reading frame of the polypeptide sequence they correspond to. This enables the separation of physiologically relevant prey protein from out-of-frame fusions which bind in the two-hybrid assay.

5.2. Each prey fragment is compared pairwise with other prey fragments and two fragments are clustered together if they overlap by more than 30% of their lengths (see FIG. 8). Further fragments are assigned to the cluster if, and only if, overlap all the fragments in the cluster by more than 30% of their length.

5.3 For each cluster of fragments thus produced, a pre-SID is defined as the intersection of all the fragments present in the cluster defined in 5.2 (FIG. 9).

5.4. The pre-SIDs defined in 5.3 are then analysed pair-wise and if the region of intersection between two pre-SIDs is greater than 30 bp then a SID® is defined as this region of intersection. If the non-intersecting region of a pre-SID is of more than 30 bp in length and this non-intersecting region represents more than 30% of the length of one of the fragments that comprises this region, then this non-intersecting region is also defined as a SID®s (FIG. 10).

5.5 The number of fragments contributing to each SID defined in 5.4 is counted. In the case of overlapping SIDs®, the SID® which contains the most fragments is identified, and all the fragments which contribute to this SID® are removed from overlapping SIDs®. The inspection of the fragments which remain in these overlapping SIDs® determines the final sequence of the SID® (FIG. 11).

TABLE 1

Summary of the protein-protein interactions between the SID polypeptides of the invention and H77 strain HCV polypeptides

| Bait | SED ID NO (1) | begin (2) | end (2) | SEQ ID NO (3) | SID | SEQ ID NO (4) | begin (2) | end (2) | SEQ ID NO (5) |
|---|---|---|---|---|---|---|---|---|---|
| Core (87%) | 114 | 302 | 614 | 77 | Core (100%) | 39 | 446 | 600 | 1 |
| Core (100%) | 115 | 342 | 683 | 78 | NS3 (100%) | 40 | 4814 | 4922 | 2 |
| Core (100%) | 115 | 342 | 683 | 78 | Core (100%) | 41 | 380 | 616 | 3 |
| E1 (100%) | 116 | 995 | 1342 | 79 | E2 (100%) | 42 | 1871 | 1987 | 4 |
| E1 (4%)/E2 (95%) | 117 | 1478 | 1756 | 80 | NS3 (100%) | 43 | 4787 | 5242 | 5 |
| E2 (100%) | 118 | 1745 | 2278 | 81 | E2 (100%) | 44 | 1871 | 1958 | 6 |
| E2 (100%) | 119 | 1799 | 2090 | 82 | E2 (100%) | 45 | 1808 | 1890 | 7 |
| NS2 (12%)/NS3 (87%) | 120 | 3312 | 4150 | 83 | NS4A (59%)/NS4B (40%) | 46 | 5375 | 5542 | 8 |
| NS3 (100%) | 121 | 3767 | 4244 | 84 | NS3 (100%) | 47 | 4676 | 4801 | 9 |
| NS3 (100%) | 122 | 3779 | 4571 | 85 | NS3 (100%) | 48 | 4856 | 4945 | 10 |
| NS3 (100%) | 123 | 3974 | 4559 | 86 | NS3 (100%) | 49 | 4817 | 4903 | 11 |
| NS3 (100%) | 124 | 4238 | 4857 | 87 | NS5B (100%) | 50 | 7979 | 8109 | 12 |
| NS3 (100%) | 125 | 4298 | 4859 | 88 | NS3 (100%) | 51 | 4031 | 4118 | 13 |
| NS3 (100%) | 126 | 4691 | 5168 | 89 | E2 (100%) | 52 | 1784 | 1888 | 14 |
| NS3 (100%) | 127 | 4838 | 5230 | 90 | E2 (100%) | 53 | 1871 | 1968 | 15 |
| NS3 (1%)/NS4A (98%) | 128 | 5310 | 5467 | 91 | NS4B (100%) | 54 | 5918 | 6154 | 16 |
| NS4A (100%) | 129 | 5342 | 5400 | 92 | NS3 (100%) | 55 | 3512 | 3956 | 17 |
| NS4B (86%)/NS5A (13%) | 130 | 5717 | 6344 | 93 | NS4B (53%)/NS5A (46%) | 56 | 6197 | 6310 | 18 |
| NS4B (70%)/NS5A (29%) | 131 | 5819 | 6444 | 94 | E2 (100%) | 57 | 1844 | 1933 | 19 |
| NS4B (55%)/NS5A (44%) | 132 | 5882 | 6562 | 95 | NS5B (100%) | 58 | 9083 | 9222 | 20 |
| NS4B (82%)/NS5A(17%) | 133 | 5897 | 6335 | 96 | NS4B (100%) | 59 | 5819 | 6080 | 21 |
| NS4B (100%) | 134 | 6011 | 6177 | 97 | E2 (100%) | 60 | 1823 | 1955 | 22 |
| NS4B (30%)/NS5A (69%) | 135 | 6107 | 6605 | 98 | NS4B (100%) | 61 | 5879 | 6072 | 23 |
| NS4B (12%)/NS5A (87%) | 136 | 6141 | 7069 | 99 | E2 (100%) | 62 | 1784 | 1875 | 24 |
| NS4B (8%)/NS5A (91%) | 137 | 6182 | 7034 | 100 | E1 (100%) | 63 | 1226 | 1458 | 25 |
| NS4B (9%)/NS5A (90%) | 138 | 6188 | 6939 | 101 | NS4B (70%)/NS5A (28%) | 64 | 6176 | 6291 | 26 |
| NS5A (100%) | 139 | 6317 | 6576 | 102 | NS3 (100%) | 65 | 4784 | 4928 | 27 |
| NS5A (100%) | 140 | 6440 | 6727 | 103 | NS5A (100%) | 66 | 6557 | 6721 | 28 |
| NS5A (100%) | 141 | 7019 | 7249 | 104 | NS3 (100%) | 67 | 4451 | 4790 | 29 |
| NS5A (100%) | 142 | 7274 | 7549 | 105 | NS4B (100%) | 68 | 6029 | 6194 | 30 |
| NS5B (100%) | 143 | 7613 | 8027 | 106 | NS5B (100%) | 69 | 8354 | 8665 | 31 |
| NS5B (100%) | 144 | 7838 | 8743 | 107 | NS5B (100%) | 70 | 7769 | 8011 | 32 |
| NS5B (100%) | 145 | 7856 | 8458 | 108 | NS3 (100%) | 71 | 4715 | 4901 | 33 |
| NS5B (100%) | 146 | 7976 | 8759 | 109 | NS5B (100%) | 72 | 7775 | 8011 | 34 |
| NS5B (100%) | 147 | 8564 | 8948 | 110 | E2 (100%) | 73 | 1805 | 1887 | 35 |
| NS5B (100%) | 148 | 8708 | 8978 | 111 | E2 (100%) | 74 | 1751 | 1865 | 36 |
| NS5B (100%) | 149 | 8996 | 9220 | 112 | NS4B (57%)/NS5A(41%) | 75 | 6194 | 6303 | 37 |
| NS5B (100%) | 150 | 9032 | 9226 | 113 | NS4B(63%)/NS5A(35%) | 76 | 6206 | 6286 | 38 |

(1) Nucleic acid sequence encoding the polypeptide from the H77 strain of HCV, which binds to the SID polypeptide (4) described in the same line.
(2) 5'-end and 3'-end nucleotide positions of the sequence SEQ ID (1) in reference to the nomenclature disclosed by Yanagi et al. (1997)
(3) Amino acid sequence of the polypeptide from the H77 strain of HCV, which binds to the SID polypeptide (4) described in the same line.
(4) Nucleic acid sequence encoding the SID polypeptide, which binds to the polypeptide of the amino acid sequence (3) described in the same line.
(5) Amino acid sequence of the SID polypeptide, which binds to the polypeptide of the amino acid sequence (3) described in the same line.

References

Aguzzi F et al., Estratto Dal. Boll. 1 st Sieroter; Milanese, 1977, vol. 56: 212–216.
Brigham K L et al., 1993, Am. J. Respir Cell Mol. Biol. 8(2):209–213.
BARTENSCHLAGER R. et al., 1995, J. Virol., 69 (12): 7519–7528.
Curiel et al. Gene Transfer to Respiratory Epithelial Cells via the Receptor Mediated Endocytosis Pathway, Am. J. Respir. Cell Mol. Biol. 6 (1992) 247–252.
Curiel et al. Adenovirus Enhancement of Transferrin-Polylysine-Mediated Gene Delivery, Proc. Natl. Acad. Sci. 88 (1991) 8850–8854.
Chalfie et al., (1994), Science, vol. 263: 802–805.
Chen F-T. A. et al., 1991, Clin. Chem., vol. 77: 14–19.
Davis et al., (1995), Development Biology, vol. 170: 726–729.
Delagrave et al., (1995), Biotechnology, vol. 13: 151–154.
DI MARCO et al., 2000, The Journal of Biological Chemistry, vol. 275 (10):7152–7157.
DUBUISSON J., 1994, J. Viral. vol. 68:6147–6160.
Drumm, M. L. et al., Cell 62:1227–1233 (1990).
Fromont-Racine M et al. (1997), Nature Genetics, vol. 16 (3):277–282.
FLAJOLET M. et al., 2000 Gene, vol. 242:369–379.
EDWARDS and LEARTHERBARROW, 1997, Analytical Biochemistry, 246:1–6.
Goding et al. J. W., (1986), In: Monoclonal antibodies: Principles and practice-production and application of monoclonal antibodies in cell biology, biochemistry and immunology, Acad. Press, London, pages 255–280.
GALLINARY P et al., 1999, Biochemistry, vol. 38:5620–5632.
GRAKOUI A., 1993, J. Viral., vol. 67:1385–1395.
HOUGHTON, M (1996), Hepatitis C virus, fields editors.
HIGIKATA M., 1993, J. Viral., vol. 67:4665–4675.
Heim et al., (1994), Proc. Natl. Acad. Sci., volume 91: 12501–12.504.
Hu and Cheng, (1995), Febs. Letters, vol. 369: 331–334.
Ichinose N et al;, (1991), In: Fluorometric analysis in biomedical chemistry, vol. 10, page 110, Chemical analysis, Winefordner J D et al. Eds., John Wiley and Sons, New York.
KARIMOVA et al., 1998, Proc. Natl. Acad. Sci., USA, 95:5752–5756.
Keegan et al. (1986), Science, vol. 231 (4739): 699–704.
KOCH Y, 1977, Biochem. Biophys. Res. Commun, vol. 74:488–491.
Kohler and Milstein, 1975, Nature, 256: 495
Kozbor et al., 1983, Hybridoma, 2(1):7–16.
KEEGAN et al., 1986, Science, Vol. 231:689–407.
Kaether and Gerdes, (1995), Febs. Letters, vol. 369:267–271.
Leger et al., 1997, Hum. Antibodies, 8(1):3–16.
Martineau et al., 1998, J. Mol. Biol., 280(1): 117–127.
Muzyczka, N., Curr. Top. Micro. Immuno. 158:97–129 (1992).
Merlini G et al. , 1983, J. Clin. Chem. Biochem., vol. 21: 841–844.
Maggio ET, "Enzyme-immuno assay", 1980, CRC Press Incorporated, Boca Raton, Fla.
MA and PATSHNE, 1987, Cell, vol. 48: 847–853.
MIN et al., 1999, virus genes, vol. 19 (1):33–43.
Nielsen et al., 1991, J. Chromatogr., vol. 539: 177.
PATEL J. et al. 1999, Journal of General Virology, vol. 80:1681–1690.
Pontiroli et al., 1987, Diabet. Metab., vol. 13:441–443.
Ridder et al., 1995, Biotechnology (NY), 13(3):255–260.
Reinmann et al., 1997, AIDS Res. Hum. Retroviruses, 13(11): 933–943.
Rosenfeld, M. A. et al., Cell 68:143–155 (1992).
Rizzuto et al., (1995), Current Biology, vol. 5: 635–142.
ROUGEOT C et al., 1994, Eur. J. Biochem., vol. 219(3) :765–773.
Shattil S J et al., (1987), Blood, vol. 70: 307.
Shattil et al. S J(1985), J. Biol. Chem., vol. 260:11.107.
Smith et al., 1988, Gene 67:31–40.
Schofield, Brit. Microencapsulated. Bull., 51(1):56–71 (1995) Behr, Bioconjugate Chem., 5, 382–389 (1994).
SZABO A. et al., 1995, Curr. Opin. Struct. Biol., 5(5): 699–705.
Trubetskoy, V. S. et al., Biochem. Biophys. Acta 1131:311–313 (1993)).
UTKIEWICZ N J et al., 2000, vol. 267: 278–282.
URBANI A et al., 1999, Biochemistry, vol. 38:5206–5215.
Wu et al., 1992, J. Biol. Chem. 267:963–967.
Wu and Wu, 1988, J. Biol. Chem. 263:14621–14624.
Wilson, J. M. et al., 1992, Endocrinology, 130(5) :2947–2954.
White Wa et al., 1986, Biochem. Clin. vol. 10:571–574.
Yanagi et al., Proc. Nat. Acad. Sci USA, 1997, 94:8738–8743.

What is claimed is:

1. A nucleic acid which encodes a polypeptide consisting essentially of the amino acid sequence of SEQ ID NO: 20.

2. A nucleic acid sequence, which encodes a polypeptide having at least 95% amino acid identity with a polypeptide having the amino acid sequence of SEQ ID NO:20 and retains the same binding affinity te as said polypeptide of SEQ ID NO:20.

3. A nucleic acid according to claim 1, wherein said nucleic acid consists essentially of SEQ ID NO:58 or a sequence complementary thereto.

4. A nucleic acid, having at least 95% nucleic acid identity with the nucleic acid of SEQ ID NO:58 or a sequence complementary thereto, and which encodes a polypeptide retaining the same binding affinity as the polypeptide of SEQ ID NO:20.

5. A nucleic acid, encoding a polypeptide having an amino acid sequence consisting essentially of 40 consecutive amino acids of SEQ ID NO:20.

6. A recombinant vector comprising a nucleic acid according to claim 1.

7. A recombinant vector comprising a nucleic acid according to claim 2.

8. A recombinant vector comprising a nucleic acid according to claim 3.

9. A recombinant vector comprising a nucleic acid according to claim 4.

10. A recombinant vector comprising a nucleic acid according to claim 5.

11. An isolated host cell transformed with a vector according to any one of claims 6 to 10.

12. A set of two nucleic acids consisting essentially of:
   (i) a first nucleic acid encoding a Selected Interacting Domain (SID®) polypeptide according to claim 1; and
   (ii) a second nucleic acid encoding a prey polypeptide which binds to the SID® polypeptide defined in i).

13. A composition comprising a set of two nucleic acids, encoding polypeptides, consisting essentially of the set SEQ ID NO:132/SEQ ID NO:58.

14. A method for selecting a molecule which inhibits the binding between a set of two polypeptides wherein said method comprises:
   a) cultivating a recombinant host cell containing a reporter gene the expression of which is toxic for said recombinant host cell, said recombinant host cell further comprising two vectors wherein:
      i) the first vector contains a nucleic acid comprising a polynucleotide encoding a first hybrid polypeptide containing a first polypeptide encoded by a nucleic acid according to any one of claims 1 to 5, and a DNA binding domain;
      ii) the second vector contains a nucleic acid comprising a polynucleotide encoding a second hybrid polypeptide containing a second polypeptide which binds with the first polypeptide, and an activating domain which activates said toxic reporter gene when the first and the second hybrid polypeptides are interacting;
      wherein said cultivating is on a selective medium containing the molecule to be tested and that allows the growth of said recombinant host cell when the toxic reporter gene is not activated; and
   b) selecting the molecule if it inhibits the growth of the recombinant host cell defined in a).

15. A method for selecting a molecule which inhibits the binding between a set of two polypeptides wherein said method comprises:
   a) cultivating a recombinant host cell containing a reporter gene the expression of which is toxic for said recombinant host cell, said recombinant host cell further comprising two vectors wherein:
      i) the first vector contains a nucleic acid comprising a polynucleotide encoding a first hybrid polypeptide containing a first polypeptide encoded by SEQ ID NO: 132, and a DNA binding domain;
      ii) the second vector contains a nucleic acid comprising a polynucleotide encoding a second hybrid polypeptide containing a second polypeptide encoded by SEQ ID NO: 58 and an activating domain which activates said toxic reporter gene when the first and the second hybrid polypeptides are interacting;
      wherein said cultivating is on a selective medium containing the molecule to be tested and that allows the growth of said recombinant host cell when the toxic reporter gene is not activated; and
   b) selecting the molecule if it inhibits the growth of the recombinant host cell defined in a).

16. A method for selecting a molecule which inhibits protein-protein interaction of a set of two polypeptides wherein said method comprises:
   a) cultivating a recombinant host cell containing a reporter gene the expression of which is toxic for said recombinant host cell, said recombinant host cell further comprising two vectors wherein:
      i) the first vector contains a nucleic acid comprising a polynucleotide encoding a first hybrid polypeptide containing a first polypeptide encoded by a nucleic acid according to any one of claims 1 to 5, and a first domain of an enzyme;
      ii.) the second vector contains a nucleic acid comprising a polynucleotide encoding a second hybrid polypeptide containing a second, polypeptide which binds with the first polypeptide and a second part of said enzyme which activates said toxic reporter gene when the first and the second hybrid polypeptides are interacting, said interaction recovering the catalytic activity of the enzyme;
      wherein said cultivating is on a selective medium containing the molecule to be tested and that allows the growth of said recombinant host cell when the toxic reporter gene is not activated; and
   b) selecting the molecule if it inhibits the growth of the recombinant host cell defined in a).

17. A method for selecting a molecule which inhibits protein-protein interaction of a set of two polypeptides wherein said method comprises:
   a) cultivating a recombinant host cell containing a reporter gene the expression of which is toxic for said recombinant host cell, said recombinant host cell further comprising two vectors wherein:
      i) the first vector contains a nucleic acid comprising a polynucleotide encoding a first hybrid polypeptide containing a first polypeptide encoded by SEQ ID NO: 132, and a first domain of an enzyme;
      ii) the second vector contains a nucleic acid comprising a polynucleotide encoding a second hybrid polypeptide containing a second polypeptide encoded by SEQ ID NQ:58, and a second part of said enzyme which activates said toxic reporter gene when the first and the second hybrid polypeptides are interacting, said interaction recovering the catalytic activity of the enzyme;
      wherein said cultivating is on a selective medium containing the molecule to be tested and that allows the growth of said recombinant host cell when the toxic gene is not activated; and
   b) selecting the molecule if it inhibits the growth of the recombinant host cell defined in a).

18. A nucleic acid encoding a two-component marker compound, wherein the first component comprises a Selected Interacting Domain (SID®) polypeptide encoded by a nucleic acid according to any one of claims 1 to 5; and the second component comprises a detectable polypeptide which can non-covalently bind to said SID® polypeptide.

19. A recombinant vector comprising a nucleic acid according to claim 18.

20. An isolated recombinant host cell which has been transformed with said recombinant vector according to claim 19.

21. An isolated recombinant host cell according to claim 20 which is of prokaryotic origin.

22. An isolated recombinant host cell according to claim 20 which is of eukaryotic origin.

23. An isolated recombinant host cell according to claim 22 which is a mammalian host cell.

24. A composition comprising a polynucleotide encoding a Selected Interacting Domain (SID®) polypeptide according to any one of claims 1 to 5, and a carrier.

25. A nucleic acid which encodes a polypeptide variant of SEQ ID NO: 20 having from one to three equivalent amino acid substitutions.

26. A nucleic acid which encodes a polypeptide consisting essentially of 40 consecutive amino acids of a variant of SEQ ID NO: 20, said variant having from one to three equivalent amino acid substitutions.

27. A nucleic acid encoding a marker compound, wherein said marker compound comprises a detectable polypeptide covalently bound to a Selected Interacting Domain (SID®) polypeptide encoded by a nucleic acid according to any one of claims 1 to 5.

28. The nucleic acid of claim 27, wherein the detectable polypeptide is fused to the SID® polypeptide.

29. The nucleic acid of claim 28, wherein said detectable polypeptide is a fluorescent protein.

30. The nucleic acid of claim 29, wherein said fluorescent protein is green fluorescent protein (GFP).

31. The nucleic acid of claim 29, wherein said fluorescent protein is yellow fluorescent protein (YFP).

32. The nucleic acid of claim 28, wherein said detectable polypeptide has catalytic activity.

33. The nucleic acid of claim 32, wherein said detectable polypeptide is an enzyme or enzymatically active enzyme fragment.

34. The nucleic acid of claim 33, wherein said enzyme is alkaline phosphatase.

35. The nucleic acid of claim 33, wherein said enzyme is glutathione peroxydase.

36. The nucleic acid of claim 33, wherein said enzyme is horse radish peroxydase.

* * * * *